United States Patent
Liu et al.

(10) Patent No.: US 8,987,252 B2
(45) Date of Patent: Mar. 24, 2015

(54) ARYLOXY- AND HETEROARYLOXY-SUBSTITUTED TETRAHYDROBENZAZEPINES AND USE THEREOF TO BLOCK REUPTAKE OF NOREPINEPHRINE, DOPAMINE, AND SEROTONIN

(75) Inventors: Shuang Liu, Schenectady, NY (US); Yuh-lin Allen Yang, Slingerlands, NY (US); Aruna Sambandam, Delmar, NY (US); Bruce F. Molino, Slingerlands, NY (US); Richard E. Olson, Orange, CT (US)

(73) Assignees: Albany Molecular Research, Inc., Albany, NY (US); Bristol-Myers Squibb Company, Princeton, NJ (US)

( * ) Notice: Subject to any disclaimer, the term of this patent is extended or adjusted under 35 U.S.C. 154(b) by 505 days.

(21) Appl. No.: 12/598,912

(22) PCT Filed: May 8, 2008

(86) PCT No.: PCT/US2008/063043
§ 371 (c)(1),
(2), (4) Date: Apr. 16, 2010

(87) PCT Pub. No.: WO2008/141082
PCT Pub. Date: Nov. 20, 2008

(65) Prior Publication Data
US 2010/0210624 A1    Aug. 19, 2010

Related U.S. Application Data

(60) Provisional application No. 60/917,200, filed on May 10, 2007.

(51) Int. Cl.
| | | |
|---|---|---|
| A61K 31/55 | (2006.01) | |
| C07D 223/16 | (2006.01) | |
| C07D 471/04 | (2006.01) | |
| C07D 401/04 | (2006.01) | |
| C07D 401/14 | (2006.01) | |
| C07D 403/04 | (2006.01) | |

(52) U.S. Cl.
CPC ............ *C07D 471/04* (2013.01); *C07D 223/16* (2013.01); *C07D 401/04* (2013.01); *C07D 401/14* (2013.01); *C07D 403/04* (2013.01)
USPC ...................... 514/213.01; 540/593

(58) Field of Classification Search
USPC ...................... 514/213.01; 540/593
See application file for complete search history.

(56) References Cited

U.S. PATENT DOCUMENTS

| 5,416,118 | A  | 5/1995  | Clader et al. |
| 6,576,664 | B1 | 6/2003  | Yao et al. |
| 6,602,883 | B1 | 8/2003  | Bhide et al. |
| 7,008,938 | B2 | 3/2006  | Ohmoto et al. |
| 7,279,468 | B2 | 10/2007 | Geneste et al. |
| 7,687,504 | B2 | 3/2010  | Jiaang et al. |
| 2005/0101600 | A1 | 5/2005 | Seko et al. |
| 2006/0069086 | A1 | 3/2006 | Michalow |
| 2006/0079495 | A1 | 4/2006 | Blum |
| 2006/0148790 | A1 | 7/2006 | Burgey et al. |
| 2007/0099938 | A1 | 5/2007 | Ohmoto et al. |

FOREIGN PATENT DOCUMENTS

| EP | 0096838 A1 | 12/1983 |
| EP | 0534344 A1 | 3/1993 |
| JP | 63094239 A2 | 4/1988 |
| WO | 9205173 A1 | 4/1992 |
| WO | 2004037788 A1 | 5/2004 |
| WO | 2007011820 A2 | 1/2007 |
| WO | 2009145357 A1 | 12/2009 |

OTHER PUBLICATIONS

International Search Report for International Patent Application No. PCT/US08/063043 (Aug. 4, 2008).
Written Opinion for International Patent Application No. PCT/US08/063043 (Aug. 4, 2008).
Supplementary European Search Report and Search Opinion and Communication Under Rules 70(2) and 70a(2) EPC for European Application No. 08747852.5 (Dec. 12, 2011).
Written Opinion for Singapore Application No. 200907286-9 (Dec. 30, 2010).
Examination Report for Singapore Application No. 200907286-9 (Sep. 6, 2011).
Examination Report for New Zealand Application No. 580802 (Oct. 15, 2010).
Examination Report for New Zealand Application No. 580802 (Aug. 24, 2011).
Examiners First Report for Australian Application No. 2008251558 dated Nov. 10, 2011.
First Office Action for Chinese Application No. 200880024102.X dated Feb. 15, 2011 (translation).
Official Action for Eurasian Application No. 2009710458 dated May 30, 2011 (translation).

(Continued)

*Primary Examiner* — Brenda Coleman
(74) *Attorney, Agent, or Firm* — LeClairRyan, a Professional Corporation

(57) ABSTRACT

The aryloxy- and heteroaryloxy-substituted tetrahydrobenzazepine derivative compounds of the present invention are represented by formulae (I) (A-E) having the following structure where the carbon atom designated * is in the R or S configuration and the substituents X and $R^1$—$R^9$ are as defined herein.

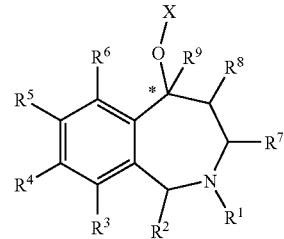

I(A-E)

22 Claims, No Drawings

(56) References Cited

OTHER PUBLICATIONS

Official Action for Mexican Application No. MX/a/2009/011922 dated Sep. 13, 2012 (translation).
Decision on Rejection Chinese Application No. 200880024102.X dated Feb. 23, 2012 (translation).
Official Action for Eurasian Application No. 200971045 dated Jan. 31, 2012 (translation).
Notice of Reasons for Rejection for Japanese Application No. 2010-507655 dated Jun. 5, 2013 (translation).
Translation of Notice of Reexamination for China Patent Application No. 200880024102.X (May 10, 2013).
Office Action for Canada Patent Application No. 2,685,861 (Jan. 31, 2014).
Translation of Decision of Rejection for Japan Patent Application No. 2010-507655 (Dec. 25, 2013).
Examination Report for New Zealand Patent Application No. 580802 (Jun. 13, 2012).
Translation of Examination Report for Israel Patent Application No. 201923 (Aug. 6, 2012)(redacted).
Translation of Notice of Defects for Israel Patent Application No. 201923 (Jan. 26, 2014).
Translation of Office Action for Korean Patent Application No. 10-2009-7025844 (Nov. 18, 2014).

ARYLOXY- AND HETEROARYLOXY-SUBSTITUTED TETRAHYDROBENZAZEPINES AND USE THEREOF TO BLOCK REUPTAKE OF NOREPINEPHRINE, DOPAMINE, AND SEROTONIN

This application claims the benefit of U.S. Provisional Patent Application Ser. No. 60/917,200, filed May 10, 2007, which is hereby incorporated by reference in its entirety.

FIELD OF THE INVENTION

The present invention relates to compounds, compositions, methods for the treatment of various neurological and psychological disorders, and the use of the compounds in combination therapy. In particular, the present invention relates to such compounds, compositions, and methods, where the compounds are novel aryloxy- and heteroaryloxy-substituted tetrahydrobenzazepine derivatives.

BACKGROUND OF THE INVENTION

It is well known that the neurotransmitters, dopamine (DA), norepinephrine (NE), and serotonin (5-HT), regulate a number of biological processes and that decreased levels of DA, NE, and 5-HT are associated with a number of neurological disorders and their physical manifestations. Significant effort has been expended on devising methods for adjusting the levels of these neurotransmitters in order to produce a desired pharmacological effect. Preventing the reuptake of these neurotransmitters in any combination of one, two, or all three of them is likely to be effective in treating these disorders. Targeting the dopamine transporter (DAT), norepinephrine transporter (NET), and the serotonin transporter (SERT) proteins has proven to be an effective way of increasing the levels of the respective monoamines.

Methylphenidate, currently used for the treatment of attention deficit-hyperactivity disorder, is known to be selective for inhibition of the DAT. Also, U.S. Pat. No. 5,444,070 discloses selective inhibitors of the dopamine reuptake as treatments for Parkinson's disease, drug addiction or abuse including cocaine and amphetamines.

Selective norepinephrine reuptake inhibitors (NARI) have also been disclosed. U.S. Pat. No. 6,352,986 describes methods of treating attention deficit-hyperactivity disorder (ADHD), addictive disorders, and psychoactive substance use disorders with Reboxetine. Also, Atomoxetine (STRATTERA®) is currently marketed as a selective NET reuptake inhibitor for ADHD.

The use of selective serotonin reuptake inhibitors (SSRI) has been shown to be effective in treating depressive disorders. Sertraline, Citalopram, and Paroxetine are well known examples of SSRIs used to treat disorders, such as depression, obsessive compulsive disorder, and panic attacks. There are several known difficulties with the SSRI class of therapeutics, including the slow onset of action, unwanted side effects, and the existence of a significant subset of the population that is not responsive to SSRI therapy.

Selective inhibitors of DAT, NET, and SERT reuptake may also be co-administered with each other or with other drugs. U.S. Pat. No. 5,532,244 discloses the use of serotonin reuptake inhibitors in combination with a serotonin 1A antagonist for the treatment of obsessive-compulsive disorder, depression, and obesity. The use of a serotonin or norepinephrine reuptake inhibitor in combination with a neurokinin-1 receptor antagonist has been disclosed in U.S. Pat. No. 6,121,261 for the treatment of ADHD. U.S. Pat. No. 4,843,071 discloses the use of a norepinephrine reuptake inhibitor in combination with a norepinephrine precursor in the treatment of obesity, drug abuse, or narcolepsy. U.S. Pat. No. 6,596,741 discloses the use of a NE, DA, or 5-HT inhibitor with either a neurokinin-1 receptor antagonist or a serotonin-1D antagonist for the treatment of a wide variety of conditions.

Also advantageous is the use of compounds that inhibit one or more of the neurotransmitters at the same time. The anti-depressant qualities of the dual NET and SERT reuptake inhibitor duloxetine is disclosed in European Patent No. EP 273658. Venlafaxine is disclosed in U.S. Pat. No. 4,535,186 as a reuptake inhibitor of both NE and 5-HT for the treatment of depressive disorders. U.S. Pat. No. 6,635,675 discloses the use of the dual NE and 5-HT reuptake inhibitor milnacipran for the treatment of chronic fatigue syndrome and fibromyalgia syndrome. In addition, dual NE and 5-HT reuptake inhibitors are also disclosed in U.S. Pat. No. 6,136,083 for the treatment of depression. It is also recognized that compounds which inhibit the reuptake of NE, DA, and 5-HT in varying ratios not specifically mentioned here would also be advantageous.

Treating illnesses by inhibiting the reuptake of all three of the monoamines either through combination therapy or "triple inhibitors" may have clinical benefit as well. Rationale for inclusion of a dopamine enhancing component in anti-depressant therapy includes observed deficits in dopaminergic function, the success of combination therapy with dopamine agonists and traditional anti-depressants, and an increased sensitivity in dopamine receptors due to chronic anti-depressant administration (Skolnick et al., *Life Sciences*, 73:3175-3179 (2003). Combination therapy with an SSRI and a noradrenaline and dopamine reuptake inhibitor was shown to be more efficacious in patients with treatment-resistant depression (Lam et al, *J. Clin. Psychiatry*, 65(3):337-340 (2004)). Another study using a combination of a serotonin and norepinephrine reuptake inhibitor with a norepinephrine and dopamine reuptake inhibitor reported a significant decrease in depressive symptoms in patients with refractory major depressive disorder who had failed to respond previously to either agent alone (Papkostas, G. I., *Depression and Anxiety*, 23:178-181 (2006)). In addition, the combination of bupropion-SR with either SSRIs or norepinephrine and dopamine reuptake inhibitors was found to induce less sexual dysfunction than monotherapy (Kennedy et al, *J. Clin. Psychiatry*, 63(3):181-186 (2002)). As such, inhibitory activity against DA reuptake, in addition to NE and 5-HT reuptake, is expected to provide a more rapid onset of anti-depressant effect than other mixed inhibitors which are selective for NET and SERT over DAT. PCT International Publication Nos. WO 03/101453 and WO 97/30997 disclose a class of compounds which are active against all three monoamine transporters. Also, PCT International Patent Publication No. WO 03/049736 discloses a series of 4-substituted piperidines, each of which displays similar activity against DA, NE, and 5-HT transporters. Bicyclo[2.2.1]heptanes (Axford et al., *Bioorg. Med. Chem. Lett.*, 13:3277-3280 (2003)) and azabicyclo[3.1.0]hexanes (Skolnick et al., *Eur. J. Pharm.*, 461:99-104 (2003)) are also described as triple inhibitors of the three monoamine transporters. 1-(3,4-Dichlorophenyl)-3-azabicyclo[3.1.0]hexane has been shown to be efficacious in treating depression in clinical trials (Beer et al, *J. Clin. Pharmacol.*, 44:1360-1367 (2004)). Current widely used anti-obesity drug sibutrimine is believed to work through the inhibition of all three transporters DAT, SERT, and SERT (Ryan, *Pharmacotherapy of Obesity*, 245-266 (2004)).

There is still a large need for compounds that block the reuptake of norepinephine, dopamine, and serotonin and treat various neurological and psychological disorders.

The present invention is directed achieving this objective.

SUMMARY OF THE INVENTION

The present invention relates to compounds represented by formulae I(A-E) having the following structure:

I(A-E)

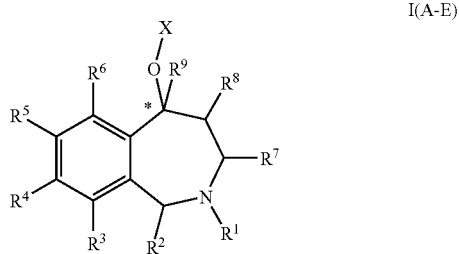

where:
the carbon atom designated * is in the R or S configuration; and

X represents a 5- or 6-membered aromatic or nonaromatic monocyclic carbocycle or heterocycle selected from the group consisting of phenyl, pyridyl, 2-oxo-pyridin-1(2H)-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$; or X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-c]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$;

$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$; or $R^2$ is gem-dimethyl;

$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^3$, $R^5$, and $R^6$ are each independently a 5- or 6-membered monocyclic carbocycle or heterocycle, optionally substituted from 1 to 4 times with substituents as defined below in $R^{14}$;

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —$C(O)R^{13}$, and —$S(O)_nR^{13}$; or $R^4$ is phenyl, pyridyl, 2-oxo-pyridin-1(2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, 2-oxooxazolidin-3-yl, or other 5- or 6-membered aromatic or non-aromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

provided that for compounds of formula IA, X is substituted phenyl and $R^4$ is substituted monocyclic or bicyclic aryl or heteroaryl;

provided that for compounds of formula IB, X is substituted bicyclic aryl or heteroaryl and $R^4$ is substituted monocyclic or bicyclic aryl or heteroaryl;

provided that for compounds of formula IC, X is substituted phenyl and $R^4$ is H, $-OR^{12}$, $-S(O)_nR^{13}$, $C(O)R^{13}$, $-NR^{10}R^{11}$, $-CN$, halogen, or $C_1$-$C_6$ alkyl, where each of the $C_1$-$C_6$ alkyl is optionally substituted from 1 to 3 times with substituents as defined below in $R^{15}$;

provided that for compounds of formula ID, X is substituted bicyclic aryl or heteroaryl and $R^4$ is H, $-OR^{12}$, $-S(O)_nR^{13}$, $C(O)R^{13}$, $-NR^{10}R^{11}$, $-CN$, halogen, or $C_1$-$C_6$ alkyl, where each of the $C_1$-$C_6$ alkyl is optionally substituted from 1 to 3 times with substituents as defined below in $R^{15}$; and provided that for compounds of formula IE, X is substituted monocyclic heteroaryl and $R^4$ is substituted monocyclic or bicyclic aryl or heteroaryl;

$R^7$ is selected from the group consisting of H, $-S(O)_nR^{13}$, $-C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^8$ is selected from the group consisting of H, halogen, $-OR^{12}$, $-S(O)_nR^{13}$, $-CN$, $-C(O)R^{13}$, $-NR^{10}R^{11}$, $C_1$-$C_6$alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^7$ and $R^8$ are gem-dimethyl, with the proviso that only one of $R^7$ and $R^8$ is gem-dimethyl;

$R^9$ is H, halogen, $-OR^{12}$, $-SR^{10}$, $C_1$-$C_6$ alkyl, $-CN$, or $-NR^{10}R^{11}$, where each of $C_1$-$C_6$ alkyl is optionally substituted from 1 to 3 times with substituents as defined below in $R^{15}$;

$R^{10}$ and $R^{11}$ are each independently selected from the group consisting of H, $-C(O)R^{13}$, $C_1$-$C_6$ alkyl, $C_3$-$C_6$ cycloalkyl, and $C_4$-$C_7$ cycloalkylalkyl, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$;

$R^{10}$ and $R^{11}$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, and is optionally substituted from 1 to 3 times with a substituent selected independently at each occurrence thereof from the group consisting of halogen, cyano, $-OR^{12}$, $-NR^{12}R^{13}$, $-S(O)_nR^{13}$, $-C(O)R^{13}$, and $C_1$-$C_4$ alkyl, where each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on a ring carbon with from 1 to 3 times with a substituent selected independently at each occurrence thereof from the group consisting of halogen, cyano, $-OR^{12}$, $-NR^{12}R^{13}$, $-S(O)_nR^{13}$, $-C(O)R^{13}$, and $C_1$-$C_4$ alkyl, or on the additional nitrogen atom from 1 to 3 times with a substituent selected independently at each occurrence thereof from the group consisting of $S(O)_nR^{13}$, $-C(O)R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{14}$; or when $R^4$ is $-NR^{10}R^{11}$ or $-C(O)NR^{10}R^{11}$, either $R^{10}$ or $R^{11}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, $-C(O)R^{13}$, and $-S(O)_nR^{13}$, or either $R^{10}$ or $R^{11}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, $-C(O)R^{13}$, and $-S(O)_nR^{13}$;

$R^{12}$ is selected from the group consisting of H, $C_1$-$C_4$ alkyl, $C_3$-$C_6$ cycloalkyl, $C_4$-$C_7$ cycloalkylalkyl, and $-C(O)R^{13}$, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$;

$R^{13}$ is selected from the group consisting of H, $-NR^{10}R^{11}$, $C_1$-$C_4$ alkyl, $C_3$-$C_6$ cycloalkyl, and $C_4$-$C_7$ cycloalkylalkyl, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$; or $R^{12}$ and $R^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or $R^{12}$ and $R^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —$OR^{10}$, —$S(O)_nR^{10}$, —$C(O)R^{10}$, —$C(O)NR^{10}R^{11}$ and $C_1$-$C_4$ alkyl, where each of $C_1$-$C_4$ alkyl is optionally substituted from 1 to 3 times with substituents as defined below in $R^{15}$;

n is 0, 1, or 2;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_n R^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of —CN, halogen, $C(O)R^{13}$, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$;

or an oxide thereof, or a pharmaceutically acceptable salt thereof.

Results of recent clinical investigations with drugs, such as duloxetine, venlafaxine, atomoxetine, and others that work mechanistically through transporter reuptake inhibition, provide evidence that potency and selectivity are important factors in leading to drugs with an improved efficacy, improved therapeutic index, and utility for treatment of new clinical indications. Duloxetine, a dual action transporter reuptake inhibitor, is a selective inhibitor for serotonin transporter protein and norepinephrine transporter protein reuptake (Sorbera et al., *Drugs of the Future,* 25(9):907-916 (2000), which is hereby incorporated by reference in its entirety) and has been marketed for the treatment of depression and diabetic peripheral neuropathic pain. In clinical studies, researchers attribute the effect of the medication on a broad spectrum of depression symptoms, which include emotional and painful physical symptoms as well as anxiety, to its dual reuptake inhibition of both serotonin and norepinephrine. Venlafaxine, which is also reported to be a selective serotonin and norepinephrine reuptake inhibitor (SNRI class), has been reported to exhibit a more rapid onset of action. The late onset of action has been a drawback with the first generation antidepressants, i.e., the single action serotonin selective reuptake inhibitors (SSRI class). For example, PROZAC®, the prototype drug in this class, can take four weeks or longer for full anti-depressive activity to take effect.

Atomoxetine (STRATTERA®), a norepinephrine selective transporter reuptake inhibitor, has been marketed for the treatment of ADHD. Unlike RITALIN®, one of the most frequently used drugs for treatment of ADHD, atomoxetine has little or no activity at the dopamine transporter. As a result, atomoxetine has the advantage that it is not scheduled as a controlled substance because it has minimal potential for substance abuse.

In a manner similar to the newer clinical agents like atomoxetine, duloxetine, and venlafaxine, the compounds of the present invention may exhibit improved efficacy towards broader symptoms of depression. The compounds of the present invention may also exhibit more rapid onset of action in the treatment of central nervous system (CNS) diseases, such as depression. In addition to providing improved efficacy, the compounds of the present invention may also exhibit fewer undesirable side effects. Finally, because the compounds of the present invention possess a diverse transporter reuptake inhibition profile, they are expected to be useful for a wider variety of CNS disorders.

DETAILED DESCRIPTION OF THE INVENTION

The present invention relates to compounds represented by formulae I(A-E) having the following structure:

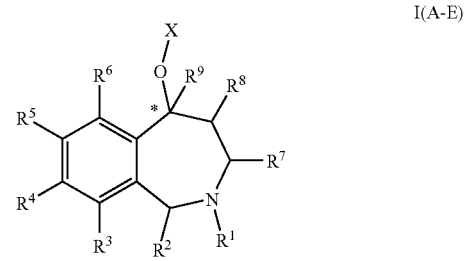

where:

the carbon atom designated * is in the R or S configuration; and

X represents a 5- or 6-membered aromatic or nonaromatic monocyclic carbocycle or heterocycle selected from the group consisting of phenyl, pyridyl, 2-oxo-pyridin-1(2H)-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$; or X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3- dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$;

$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$; or $R^2$ is gem-dimethyl;

$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^3$, $R^5$, and $R^6$ are each independently a 5- or 6-membered monocyclic carbocycle or heterocycle, optionally substituted from 1 to 4 times with substituents as defined below in $R^{14}$;

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_nR^{13}$; or $R^4$ is phenyl, pyridyl, 2-oxo-pyridin-1(2H)-yl, pyrimidinyl, pyridazinyl, pyrazinyl, 6-oxopyridazin-1(6H)-yl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, 2-oxooxazolidin-3-yl, or other 5- or 6-membered aromatic or non-aromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

provided that for compounds of formula IA, X is substituted phenyl and $R^4$ is substituted monocyclic or bicyclic aryl or heteroaryl;

provided that for compounds of formula IB, X is substituted bicyclic aryl or heteroaryl and $R^4$ is substituted monocyclic or bicyclic aryl or heteroaryl;

provided that for compounds of formula IC, X is substituted phenyl and $R^4$ is H, —$OR^{12}$, —$S(O)_nR^{13}$, $C(O)R^{13}$, —$NR^{10}R^{11}$, —CN, halogen, or $C_1$-$C_6$ alkyl, where each of the $C_1$-$C_6$ alkyl is optionally substituted from 1 to 3 times with substituents as defined below in $R^{15}$;

provided that for compounds of formula ID, X is substituted bicyclic aryl or heteroaryl and $R^4$ is H, —$OR^{12}$, —$S(O)_nR^{13}$, $C(O)R^{13}$, —$NR^{10}R^{11}$, —CN, halogen, or $C_1$-$C_6$ alkyl, where each of the $C_1$-$C_6$ alkyl is optionally substituted from 1 to 3 times with substituents as defined below in $R^{15}$; and provided that for compounds of formula IE, X is substituted monocyclic heteroaryl and $R^4$ is substituted monocyclic or bicyclic aryl or heteroaryl;

$R^7$ is selected from the group consisting of H, —$S(O)_nR^{13}$, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^8$ is selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^7$ and $R^8$ are gem-dimethyl, with the proviso that only one of $R^7$ and $R^8$ is gem-dimethyl;

$R^9$ is H, halogen, —$OR^{12}$, —$SR^{10}$, $C_1$-$C_6$ alkyl, —CN, or —$NR^{10}R^{11}$, where each of $C_1$-$C_6$ alkyl is optionally substituted from 1 to 3 times with substituents as defined below in $R^{15}$;

$R^{10}$ and $R^{11}$ are each independently selected from the group consisting of H, —$C(O)R^{13}$, $C_1$-$C_6$ alkyl, $C_3$-$C_6$ cycloalkyl, and $C_4$-$C_7$ cycloalkylalkyl, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$;

$R^{10}$ and $R^{11}$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, and is optionally substituted from 1 to 3 times with a substituent selected independently at each occurrence thereof from the group consisting of halogen, cyano, —$OR^{12}$, —$NR^{12}R^{13}$, —$S(O)_nR^{13}$, —$C(O)R^{13}$, and $C_1$-$C_4$ alkyl, where each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on a ring carbon with from 1 to 3 times with a substituent selected independently at each occurrence thereof from the group consisting of halogen, cyano, —$OR^{12}$, —$NR^{12}R^{13}$, —$S(O)_nR^{13}$, —$C(O)R^{13}$, and $C_1$-$C_4$ alkyl, or on the additional nitrogen atom from 1 to 3 times with a substituent selected independently at each occurrence thereof from the group consisting of $S(O)_nR^{13}$, —$C(O)R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{14}$; or when $R^4$ is —$NR^{10}R^{11}$ or —$C(O)NR^{10}R^{11}$, either $R^{10}$ or $R^{11}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_nR^{13}$, or either $R^{10}$ or $R^{11}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —$C(O)R^{13}$, and —$S(O)_nR^{13}$;

$R^{12}$ is selected from the group consisting of H, $C_1$-$C_4$ alkyl, $C_3$-$C_6$ cycloalkyl, $C_4$-$C_7$ cycloalkylalkyl, and —$C(O)R^{13}$, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$;

$R^{13}$ is selected from the group consisting of H, —$NR^{10}R^{11}$, $C_1$-$C_4$ alkyl, $C_3$-$C_6$ cycloalkyl, and $C_4$-$C_7$ cycloalkylalkyl, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$; or $R^{12}$ and $R^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or $R^{12}$ and $R^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —$OR^{10}$, —$S(O)_nR^{10}$, —$C(O)R^{10}$, —$C(O)NR^{10}R^{11}$ and $C_1$-$C_4$ alkyl, where each of $C_1$-$C_4$ alkyl is optionally substituted from 1 to 3 times with substituents as defined below in $R^{15}$;

n is 0, 1, or 2;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of —CN, halogen, $C(O)R^{13}$, $C_1$-$C_3$ alkyl, —$OR^{12}$, $NR^{10}R^{11}$, —$S(O)_nR^{13}$, aryl, and heteroaryl, where each of the aryl or heteroaryl groups is optionally substituted from 1 to 4 times with substituents as defined above in $R^{14}$;

or an oxide thereof, or a pharmaceutically acceptable salt thereof.

As used above, and throughout the description of the invention, the following terms, unless otherwise indicated, shall be understood to have the following meanings The term "monocyclic carbocycle" means a monocyclic ring system of 5 to about 8 ring carbon atoms, preferably 5 or 6. The ring is nonaromatic, but may contain one or more carbon-carbon double bonds. Representative monocyclic carbocycles include cyclopentyl, cyclohexyl, cyclopentenyl, cyclohexenyl, and the like.

The term "monocyclic heterocycle" means a monocyclic ring system consisting of about 5 to 8 ring atoms, preferably 5 or 6, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. The ring is nonaromatic, but may be fused to an aromatic ring. Representative monocyclic heterocycles include pyrrolidine, piperidine, piperazine, and the like.

The term "aromatic monocyclic carbocycle" means a monocyclic ring system of 5 to about 8 ring carbon atoms, preferably 6. The ring is aromatic. Representative monocyclic carbocycles include phenyl, and the like.

The term "aromatic monocyclic heterocycle" means a monocyclic ring system consisting of about 5 to 8 ring atoms, preferably 5 or 6, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. The ring is aromatic. Representative aromatic monocyclic heterocycles include pyrrole, pyridine, oxazole, thiazole, and the like. For lactam analogues of "aromatic monocyclic heterocycles" such as pyridin-2(1H)-one, pyridazin-3(2H)-one, and the like, when these lactam analogues are structurally connected through the nitrogen atom adjacent to the lactam carbonyl, these lactam analogues of aromatic monocyclic heterocycle are considered as "aromatic monocyclic heterocycle" in accordance with this invention.

The term "fused bicyclic carbocycle" means a bicyclic ring system consisting of about 8 to 11 ring carbon atoms, preferably 9 or 10. One or both of the rings is/are aromatic. Representative fused bicyclic carbocycles include indenyl, indanyl, naphthyl, dihydronaphthyl, tetrahydronaphthyl, benzocycloheptenyl, dihydrobenzocycloheptenyl, tetrahydrobenzocycloheptenyl, and the like.

The term "fused bicyclic heterocycle" means a bicyclic ring system consisting of about 8 to 13 ring atoms, preferably 9 or 10, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. Representative fused bicyclic heterocycles include benzofuranyl, benzothiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, 5,6,7,8-tetrahydro-[1,2,4]triazolo[4,3-a]pyrazinyl, [1,2,4]triazolo[4,3-a]pyrazinyl, thieno[2,3-b]pyridinyl, thieno[3,2-b]pyridinyl, 1H-pyrrolo[2,3-b]pyridinyl, chromenyl, dihydrobenzothiophenyl, dihydrobenzofuranyl, indolinyl, quinolinyl, isoquinolinyl, 4H-quinolizinyl, 9aH-quinolizinyl, quinazolinyl, cinnolinyl, quinoxalinyl, benzo[1,2,3]triazinyl, benzo[1,2,4]triazinyl, and the like. For lactam analogues of "fused bicyclic heterocycles" such as [1,2,4]triazolo[4,3-a]pyridin-3(2H)-one, and the like, when these lactams analogues are structurally connected through the nitrogen atom adjacent to the lactam carbonyl, these lactam analogues of aromatic monocyclic heterocycle are considered as "fused bicyclic heterocycle" in accordance with this invention.

The term "bridged bicyclic ring" means a bridged bicyclic ring containing 6-12 carbon atoms and optionally containing one or more heteroatoms selected from the group consisting of oxygen, nitrogen, and sulfur. Representative bridged bicyclic rings include quinuclidine, 9-azabicyclo[3.3.1]nonane, 7-azabicyclo[2.2.1]heptane, 2,5-diazabicyclo[2.2.2]octane, and the like.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Representative alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having 2 to about 6 carbon atoms in the chain. Preferred alkenyl groups have 2 to about 4 carbon atoms in the chain. Branched means that one or more lower alkyl groups such as methyl, ethyl or propyl are attached to a linear alkenyl chain. Representative alkenyl groups include ethenyl, propenyl, n-butenyl, and i-butenyl.

The term "alkynyl" means an aliphatic hydrocarbon group containing a carbon-carbon triple bond and which may be straight or branched having 2 to about 6 carbon atoms in the chain. Preferred alkynyl groups have 2 to about 4 carbon atoms in the chain. Branched means that one or more lower alkyl groups such as methyl, ethyl or propyl are attached to a linear alkynyl chain. Representative alkynyl groups include ethynyl, propynyl, n-butynyl, 2-butynyl, 3-methylbutynyl, and n-pentynyl.

The term "cycloalkyl" means a non-aromatic mono- or multicyclic ring system of about 3 to about 7 carbon atoms, preferably of about 5 to about 7 carbon atoms. Representative monocyclic cycloalkyl include cyclopentyl, cyclohexyl, cycloheptyl, and the like.

The term "cycloalkylalkyl" means a cycloalkyl-alkyl-group in which the cycloalkyl and alkyl are as defined herein. Representative cycloalkylalkyl groups include cyclopropylmethyl and cyclopentylmethyl.

The term "aryl" means an aromatic monocyclic or multicyclic ring system of 6 to about 14 carbon atoms, preferably of 6 to about 10 carbon atoms. Representative aryl groups include phenyl and naphthyl.

The term "heteroaryl" means an aromatic monocyclic or multicyclic ring system of 6 to about 14 ring atoms, preferably of 6 to about 10 ring atoms, in which one or more of the atoms in the ring system is/are element(s) other than carbon, for example, nitrogen, oxygen or sulfur. Representative heteroaryl groups include pyridinyl, pyridazinyl and quinolinyl.

The term "alkoxy" means an alkyl-O-group where the alkyl group is as herein described. Representative alkoxy groups include methoxy, ethoxy, n-propoxy, i-propoxy, n-butoxy and heptoxy.

The term "halo" or "halogen" means fluoro, chloro, bromo, or iodo.

The term "haloalkyl" means both branched and straight-chain alkyl substituted with 1 or more halogen, where the alkyl group is as herein described.

The term "haloalkoxy" means a $C_{1-4}$ alkoxy group substituted by at least one halogen atom, where the alkoxy group is as herein described.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "compounds of the invention", and equivalent expressions, are meant to embrace compounds of general formulae I(A-E) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are some-times indicated in the text, but these instances are purely illustrative and it is not intended to exclude other instances when the context so permits.

The term "pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Representative acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like. (See, for example Berge et al., *J Pharm Sci*, 66:1-sup. 19 (1977) and *Remington's Pharmaceutical Sciences*, 17th ed, p. 1418, Mack Publishing Company, Easton, Pa. (1985), which are hereby incorporated by reference in their entirety.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide. Suitable amine base addition salts are prepared from amines which have sufficient basicity to form a stable salt, and preferably include the following amines which are frequently used in medicinal chemistry because of their low toxicity and acceptability for medical use: ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Bundgaard, ed., *Design of Prodrugs*, Elsevier (1985); Widder et al., *Methods in Enzymology*, ed., Academic Press, 42:309-396 (1985); "Design and Applications of Prodrugs," Krogsgaard-Larsen, ed., *A Textbook of Drug Design and Development*, Chapter 5:113-191 (1991); Bundgaard, "*Advanced Drug Delivery Reviews,*" 8:1-38 (1992); Bundgaard et al., *Journal of Pharmaceutical Sciences*, 77:285 (1988); Nakeya et al., *Chem Pharm Bull*, 32:692 (1984); Higuchi, "Pro-drugs as Novel Delivery Systems" Roche, ed., A.C.S. Symposium Series, Vol. 14, and "Bioreversible Carriers in Drug Design" American Pharmaceutical Association and Pergamon Press (1987), which are hereby incorporated by reference in their entirety. Examples of prodrugs include, but are not limited to, acetate, formate and benzoate derivatives of alcohol and amine functional groups in the compounds of the invention.

The term "therapeutically effective amounts" is meant to describe an amount of compound of the present invention effective in increasing the levels of serotonin, norepinephrine or dopamine at the synapse and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition and medical history, the particular compound used, as well as the carrier in which it is formulated and the route of administration selected for it; and, the nature and severity of the condition being treated.

The term "pharmaceutical composition" means a composition comprising compounds of formulae I(A-E) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, 17th ed, Easton, Pa., Mack Publishing Company (1985), which is hereby incorporated by reference in its entirety.

One embodiment of the present invention relates to the compound of formula (IA), where X is substituted phenyl and $R^4$ is substituted monocyclic or bicyclic aryl or heteroaryl.

Another embodiment of the present invention relates to the compound of formula (IB), where X is substituted bicyclic aryl or heteroaryl and $R^4$ is substituted monocyclic or bicyclic aryl or heteroaryl.

Another embodiment of the present invention relates to the compound of formula (IC), where X is substituted phenyl and $R^4$ is H, $-OR^{12}$, $-S(O)_nR^{13}$, $C(O)R^{13}$, $-NR^{10}R^{11}$, $-CN$, halogen, and $C_1$-$C_6$ alkyl, where each of the $C_1$-$C_6$ alkyl is optionally substituted from 1 to 3 times with substituents as defined below in $R^{15}$.

Another embodiment of the present invention relates to the compound of formula (ID), where X is substituted bicyclic aryl or heteroaryl and $R^4$ is H, $-OR^{12}$, $-S(O)_nR^{13}$, $C(O)R^{13}$, $-NR^{10}R^{11}$, $-CN$, halogen, or $C_1$-$C_6$ alkyl, where each of the $C_1$-$C_6$ alkyl is optionally substituted from 1 to 3 times with substituents as defined below in $R^{15}$.

Another embodiment of the present invention relates to the compound of formula (IE), where X is substituted monocyclic heteroaryl and $R^4$ is substituted monocyclic or bicyclic aryl or heteroaryl.

Another embodiment of the present invention relates to the compound of formulae I(A-E) where:

X is phenyl, optionally substituted from 1 to 4 times with substituents as defined below in $R^{14}$;
$R^1$ is H, methyl, ethyl, or isopropyl;
$R^2$ is H, methyl, or gem-dimethyl;
$R^3$ is H, methyl, hydroxyl, methoxy, fluoro, chloro, cyano, trifluoromethyl, difluoromethoxy or trifluoromethoxy;
$R^4$ is H, halogen, $-OR^{12}$, $-S(O)_nR^{13}$, $-CN$, $-C(O)R^{13}$, $-NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or
$R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, $-C(O)R^{13}$, and $-S(O)_nR^{13}$;

$R^5$ is H, fluoro, chloro, methyl, trifluoromethyl, difluoromethoxy, trifluoromethoxy, cyano, hydroxyl or methoxy;
$R^6$ is H, fluoro, chloro, methyl, trifluoromethyl, difluoromethoxy, trifluoromethoxy, cyano, hydroxyl or methoxy;
$R^7$ is H, gem-dimethyl, or $C_1$-$C_4$ alkyl, where each of the $C_1$-$C_4$ alkyl is optionally substituted from 1 to 3 times with substituents as defined below in $R^{15}$;
$R^8$ is H, hydroxyl, fluoro, chloro, methyl, $C_1$-$C_3$ alkyl optionally substituted with hydroxyl or amino, or amino optionally substituted with $C_1$-$C_3$ alkyl;
$R^9$ is H, fluoro, chloro, methyl, hydroxyl, or cyano;
$R^{14}$ is independently selected at each occurrence from a substituent in the group consisting of halogen, $-NO_2$, $-OR^{12}$, $-NR^{10}R^{11}$, $-NR^{12}C(O)_2R^{13}$, $-NR^{12}C(O)NR^{12}R^{13}$, $-S(O)_nR^{13}$, $-CN$, $-C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and
$R^{15}$ is independently selected at each occurrence from a substituent in the group consisting of halogen, $-C(O)R^{13}$, $-CN$, $C_1$-$C_3$ alkyl, $-OR^{12}$, $-NR^{10}R^{11}$, $-S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae I(A-E) where:
X is phenyl, optionally substituted from 1 to 4 times with substituents as defined below in $R^{14}$;
$R^1$ is H, methyl, ethyl, or isopropyl;
$R^2$ is H, methyl, or gem-dimethyl;
$R^3$ is H, methyl, hydroxyl, methoxy, fluoro, chloro, cyano, trifluoromethyl, or trifluoromethoxy;
$R^4$ is phenyl, pyridyl, 2-oxo-pyridin-1(2H)-yl, pyrimidinyl, pyridazinyl, pyrazinyl, 6-oxopyridazin-1(6H)-yl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, oxooxazolidin-3-yl, or other 5- or 6-membered aromatic or non-aromatic monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxyl, fluoro, chloro, methyl, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl, or cyano;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, —$C(O)R^{13}$, —CN, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae I(A-E) where:

X represents a 5- or 6-membered monocyclic heterocycle selected from the group consisting of pyridyl, 2-oxo-pyridin-1(2H)-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$; or X, in compounds represented by formula (I), is an alkene or alkyne, optionally substituted from 1 to 4 times with substitutents as defined below in $R^{15}$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, or trifluoromethoxy;

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_nR^{13}$;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxyl, fluoro, chloro, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl, or cyano;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, —$C(O)R^{13}$, —CN, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae I(A-E) where:

X represents a 5- or 6-membered monocyclic heterocycle selected from the group consisting of pyridyl, 2-oxo-pyridin-1(2H)-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, difluoromethoxy, or trifluoromethoxy;

$R^4$ is phenyl, pyridyl, 2-oxo-pyridin-1(2H)-yl, pyrimidinyl, pyridazinyl, pyrazinyl, 6-oxopyridazin-1(6H)-yl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]

oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, oxooxazolidin-3-yl, or other 5- or 6-membered aromatic or non-aromatic monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^5$ is H, fluoro, chloro, methyl, trifluoromethyl, difluoromethoxy, trifluoromethoxy, cyano, hydroxyl, or methoxy;

$R^6$ is H, fluoro, chloro, methyl, trifluoromethyl, difluoromethoxy, trifluoromethoxy, cyano, hydroxyl, or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxyl, fluoro, chloro, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl or cyano;

$R^{14}$ is independently selected at each occurrence from a substituent in the group consisting of halogen, $-NO_2$, $-OR^{12}$, $-NR^{10}R^{11}$, $-NR^{12}C(O)_2R^{13}$, $-NR^{12}C(O)NR^{12}R^{13}$, $-S(O)_nR^{13}$, $-CN$, $-C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, $-C(O)R^{13}$, $-CN$, $C_1$-$C_3$ alkyl, $-OR^{12}$, $-NR^{10}R^{11}$, $-S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae I(A-E) where:

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, difluoromethoxy or trifluoromethoxy;

$R^4$ is H, halogen, $-OR^{12}$, $-S(O)_nR^{13}$, $-CN$, $-C(O)R^{13}$, $-NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, $-C(O)R^{13}$, and $-S(O)_nR^{13}$;

$R^5$ is H, fluoro, chloro, methyl, trifluoromethyl, difluoromethoxy, trifluoromethoxy, cyano, hydroxyl, or methoxy;

$R^6$ is H, fluoro, chloro, methyl, difluoromethoxy, trifluoromethyl, trifluoromethoxy, cyano, hydroxyl, or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxyl, fluoro, chloro, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl, or cyano;

$R^{14}$ is independently selected at each occurrence from a substituent in the group consisting of halogen, $-NO_2$, $-OR^{12}$, $-NR^{10}R^{11}$, $-NR^{12}C(O)_2R^{13}$, $-NR^{12}C(O)NR^{12}R^{13}$, $-S(O)_nR^{13}$, $-CN$, $-C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, $-C(O)R^{13}$, $-CN$, $C_1$-$C_3$ alkyl, $-OR^{12}$, $-NR^{10}R^{11}$, $-S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae I(A-E) where:

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[c/]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, difluoromethoxy, or trifluoromethoxy;

$R^4$ is phenyl, pyridyl, 2-oxo-pyridin-(2H)-yl, pyrimidinyl, pyridazinyl, pyrazinyl, 6-oxopyridazin-1(6H)-yl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-c/]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, oxooxazolidin-3-yl, or other 5- or 6-membered aromatic or non-aromatic monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^5$ is H, fluoro, chloro, methyl, trifluoromethyl, difluoromethoxy, trifluoromethoxy, cyano, hydroxyl, or methoxy;

$R^6$ is H, fluoro, chloro, methyl, trifluoromethyl, difluoromethoxy, trifluoromethoxy, cyano, hydroxyl, or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxyl, fluoro, chloro, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl, or cyano;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, —$C(O)R^{13}$, —CN, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae I(A-E) where:

X is thiophenyl, thiazolyl, pyridinyl, phenyl, naphthyl, benzo[b]thiophenyl, benzofuranyl, benzo[d][1,3]dioxolyl, 2,3-dihydrobenzo[b][1,4]dioxinyl, 3,4-dihydro-2H-benzo[b][1,4]oxazinyl, or 4-methyl-3,4-dihydro-2H-benzo[b][1,4]oxazinyl, optionally substituted with from 1 to 3 substituents selected independently from the group consisting of halogen, methoxy, cyano, trifluoromethyl, trifluoromethoxy, difluoromethoxy, substituted $C_1$-$C_3$ alkyl, methanesulfonyl, carbamoyl, $C_1$-$C_3$ alkyl-substituted carbamoyl, and acetamido;

$R^1$ is H, methyl, ethyl, isopropyl, 2-hydroxyethyl, 2,2,2-trifluoroethyl, 2-fluoroethyl, or benzyl;

$R^2$ is H or gem-dimethyl;

$R^3$ is H, chloro, or fluoro;

$R^4$ is H, methoxy, hydroxyl, methyl, fluoro, bromo, cyano, difluoromethyl, trifluoromethyl, difluoromethoxy, trifluoromethoxy, acetyl, aminomethyl, 1-aminocyclopropyl, morpholinomethyl, 2-hydroxypropan-2-yl, morpholine-4-carbonyl, 2-morpholinoethoxy, 2-(dimethylamino)ethyl(methyl)amino, 2-hydroxyethylamino, piperidin-1-yl, piperidin-2-yl, pyrrolidin-1-yl, piperidin-4-ol, morpholino, piperazin-1-yl, 4-methylpiperazin-1-yl, 4-(ethylsulfonyl)piperazin-1-yl, 4-(2-(isopropylamino)-2-oxoethyl)piperazin-1-yl, 4-(pyridin-2-yl)piperazin-1-yl, 4-(pyrimidin-2-yl)piperazin-1-yl, 2-oxopyrrolidin-1-yl, 2-oxopiperidin-1-yl, 6-methylpyridazin-3-yloxy, 6-aminopyridazin-3-yloxy, pyridazin-3-yloxy, pyrazin-2-yloxy, 3-aminopyrazin-2-yloxy, 5-aminopyrazin-2-yloxy, 6-aminopyrazin-2-yloxy, 1,2,4-oxadiazol-3-yl, 3,5-dimethylisoxazol-4-yl, 1H-pyrazol-4-yl, 2-cyanophenyl, 3-cyanophenyl, 4-cyanophenyl, (methanesulfonyl)phenyl, carbamoylphenyl, pyridinyl, aminopyridinyl, pyridazin-3-yl, 6-methylpyridazin-3-yl, 6-(trifluoromethyl)pyridazin-3-yl, 6-(difluoromethyl)pyridazin-3-yl, 6-((difluoromethoxy)methyl)pyridazin-3-yl, 6-aminopyridazin-3-yl, 6-(methylamino)pyridazin-3-yl, 6-(dimethylamino)pyridazin-3-yl, 6-morpholinopyridazin-3-yl, 6-(4-hydroxypiperidin-1-yl)pyridazin-3-yl, 6-(4-methylpiperazin-1-yl)pyridazin-3-yl, (6-(hydroxymethyl)pyridazin-3-yl, 6-(methoxycarbonyl)pyridazin-3-yl, pyrimidin-2-yl, pyrimidin-4-yl, pyrimidin-5-yl, pyrazin-2-yl, 3-aminopyrazin-2-yl, 5-aminopyrazin-2-yl, 6-aminopyrazin-2-yl, 2-oxopyridin-1(2H)-yl, 2-oxopyrrolidin- 1-yl, 6-oxo-1,6-dihydropyridazin-3-yl, 6-oxopyridazin-1 (6H)-yl, imidazo[1,2-a]pyridin-6-yl, imidazo[1,2-a]pyrazin-3-yl, 3-oxo-[1,2,4]triazolo[4,3-a]pyridin-2(3H)-yl, 5,6-dihydroimidazo[1,2-a]pyrazin-7(8H)-yl, 3-(trifluoromethyl)-5,6-dihydro-[1,2,4]triazolo[4,3-a] pyrazin-7(8H)-yl, [1,2,4]triazolo[1,5-a]pyridin-6-yl, [1,2,4]triazolo[4,3-a]pyridin-6-yl, 3,3-dimethyl-2-oxoindolin-5-yl, 5,6-dihydroimidazo[1,2-a]pyrazin-7(8H)-yl, 3-methyl-[1,2,4]triazolo[4,3-b]-pyridazinyl, [1,2,4]triazolo[4,3-b]-pyridazinyl, or oxooxazolidin-3-yl;

$R^5$ is H, chloro, or fluoro;
$R^6$ is H, chloro, or fluoro;
$R^7$ is H;
$R^8$ is H, fluoro, methyl, or hydroxyl;
$R^9$ is H or hydroxyl;
$R^{14}$ is independently selected at each occurrence from a substituent in the group consisting of halogen, $-NO_2$, $-OR^{12}$, $-NR^{10}R^{11}$, $-NR^{12}C(O)_2R^{13}$, $-NR^{12}C(O)NR^{12}R^{13}$, $-S(O)_nR^{13}$, $-CN$, $-C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and
$R^{15}$ is independently selected at each occurrence from a substituent in the group consisting of halogen, $-C(O)R^{13}$, $-CN$, $C_1$-$C_3$ alkyl, $-OR^{12}$, $-NR^{10}R^{11}$, $-S(O)_nR^{13}$, aryl, and heteroaryl, where each of the aryl or heteroaryl groups is optionally substituted from 1 to 4 times with substituents as defined above in $R^{14}$.

Specific compounds of formulae I(A-E) of the present invention are the following tetrahydrobenzazepine compounds:

8-bromo-2-methyl-5-phenoxy-2,3,4,5-tetrahydro-1H-benzo[c]azepine;
8-methoxy-2-methyl-5-phenoxy-2,3,4,5-tetrahydro-1H-benzo[c]azepine;
2-methyl-5-phenoxy-8-(pyridazin-3-yl)-2,3,4,5-tetrahydro-1H-benzo[c]azepine;
2-methyl-5-phenoxy-8-(1H-pyrazol-4-yl)-2,3,4,5-tetrahydro-1H-benzo[c]azepine;
6-(2-methyl-5-phenoxy-2,3,4,5-tetrahydro-1H-benzo[c]azepin-8-yl)pyridazin-3-amine;
2-methyl-5-phenoxy-8-(pyrimidin-2-yl)-2,3,4,5-tetrahydro-1H-benzo[c]azepine;
2-methyl-5-phenoxy-2-methyl-8-(pyrimidin-5-yl)-2,3,4,5-tetrahydro-1H-benzo[c]azepine;
2-methyl-5-phenoxy-8-(pyrazin-2-yl)-2,3,4,5-tetrahydro-1H-benzo[c]azepine;
2-methyl-5-phenoxy-2,3,4,5-tetrahydro-1H-benzo[c]azepin-8-yl)pyridin-2-amine;
2-methyl-5-phenoxy-2,3,4,5-tetrahydro-1H-benzo[c]azepin-8-yl)pyridazin-3(2H)-one;
2-methyl-8-(4-(methylsulfonyl)phenyl)-5-phenoxy-2,3,4,5-tetrahydro-1H-benzo[c]azepine;
2-(2-methyl-5-phenoxy-2,3,4,5-tetrahydro-1H-benzo[c]azepin-8-yl)benzonitrile;
8-([1,2,4]triazolo[1,5-a]pyridin-6-yl)-2-methyl-5-phenoxy-2,3,4,5-tetrahydro-1H-benzo[c]azepine;
2-methyl-5-phenoxy-2,3,4,5-tetrahydro-1H-benzo[c]azepin-8-yl)pyridin-2(1H)-one;
8-(4-(ethylsulfonyl)piperazin-1-yl)-2-methyl-5-phenoxy-2,3,4,5-tetrahydro-1H-benzo[c]azepine;
8-(6-methylpyridazin-3-yl)-5-phenoxy-2,3,4,5-tetrahydro-1H-benzo[c]azepine;
2-methyl-8-(6-methylpyridazin-3-yl)-5-phenoxy-2,3,4,5-tetrahydro-1H-benzo[c]azepine;

5-(2-fluorophenoxy)-2-methyl-8-(pyridazin-3-yl)-2,3,4,5-tetrahydro-1H-benzo[c]azepine;
5-(2-fluorophenoxy)-2-methyl-8-(1H-pyrazol-4-yl)-2,3,4,5-tetrahydro-1H-benzo[c]azepine;
6-(5-(2-fluorophenoxy)-2-methyl-2,3,4,5-tetrahydro-1H-benzo[c]azepin-8-yl)pyridazin-3-amine;
5-(2-fluorophenoxy)-2-methyl-8-(pyrimidin-2-yl)-2,3,4,5-tetrahydro-1H-benzo[c]azepine;
5-(2-fluorophenoxy)-2-methyl-8-(pyrimidin-5-yl)-2,3,4,5-tetrahydro-1H-benzo[c]azepine;
5-(2-fluorophenoxy)-2-methyl-8-(pyrazin-2-yl)-2,3,4,5-tetrahydro-1H-benzo[c]azepine;
6-(5-(2-fluorophenoxy)-2-methyl-2,3,4,5-tetrahydro-1H-benzo[c]azepin-8-yl)pyridin-2-amine;
6-(5-(2-fluorophenoxy)-2-methyl-2,3,4,5-tetrahydro-1H-benzo[c]azepin-8-yl)pyridazin-3(2H)-one;
5-(2-fluorophenoxy)-2-methyl-8-(4-(methylsulfonyl)phenyl)-2,3,4,5-tetrahydro-1H-benzo[c]azepine;
2-(5-(2-fluorophenoxy)-2-methyl-2,3,4,5-tetrahydro-1H-benzo[c]azepin-8-yl)benzonitrile;
8-([1,2,4]triazolo[1,5-a]pyridin-6-yl)-5-(2-fluorophenoxy)-2-methyl-2,3,4,5-tetrahydro-1H-benzo[c]azepine;
1-(5-(2-fluorophenoxy)-2-methyl-2,3,4,5-tetrahydro-1H-benzo[c]azepin-8-yl)pyridin-2(1H)-one;
8-(4-(ethylsulfonyl)piperazin-1-yl)-5-(2-fluorophenoxy)-2-methyl-2,3,4,5-tetrahydro-M-benzo[c]azepine;
5-(3-fluorophenoxy)-2-methyl-8-(pyridazin-3-yl)-2,3,4,5-tetrahydro-1H-benzo[c]azepine;
5-(3-fluorophenoxy)-2-methyl-8-(1H-pyrazol-4-yl)-2,3,4,5-tetrahydro-1H-benzo[c]azepine;
6-(5-(3-fluorophenoxy)-2-methyl-2,3,4,5-tetrahydro-1H-benzo[c]azepin-8-yl)pyridazin-3-amine;
5-(3-fluorophenoxy)-2-methyl-8-(pyrimidin-2-yl)-2,3,4,5-tetrahydro-1H-benzo[c]azepine;
5-(3-fluorophenoxy)-2-methyl-8-(pyrimidin-5-yl)-2,3,4,5-tetrahydro-1H-benzo[c]azepine;
5-(3-fluorophenoxy)-2-methyl-8-(pyrazin-2-yl)-2,3,4,5-tetrahydro-1H-benzo[c]azepine;
6-(5-(3-fluorophenoxy)-2-methyl-2,3,4,5-tetrahydro-1H-benzo[c]azepin-8-yl)pyridin-2-amine;
6-(5-(3-fluorophenoxy)-2-methyl-2,3,4,5-tetrahydro-1H-benzo[c]azepin-8-yl)pyridazin-3(2H)-one;
5-(3-fluorophenoxy)-2-methyl-8-(4-(methylsulfonyl)phenyl)-2,3,4,5-tetrahydro-1H-benzo[c]azepine;
2-(5-(3-fluorophenoxy)-2-methyl-2,3,4,5-tetrahydro-1H-benzo[c]azepin-8-yl)benzonitrile;
8-([1,2,4]triazolo[1,5-a]pyridin-6-yl)-5-(3-fluorophenoxy)-2-methyl-2,3,4,5-tetrahydro-1H-benzo[c]azepine;
8-([1,2,4]triazolo[4,3-a]pyridin-6-yl)-5-(3-fluorophenoxy)-2-methyl-2,3,4,5-tetrahydro-1H-benzo[c]azepine;
1-(5-(3-fluorophenoxy)-2-methyl-2,3,4,5-tetrahydro-1H-benzo[c]azepin-8-yl)pyridin-2(1H)-one;
8-(4-(ethylsulfonyl)piperazin-1-yl)-5-(3-fluorophenoxy)-2-methyl-2,3,4,5-tetrahydro-1H-benzo[c]azepine;
5-(4-fluorophenoxy)-2-methyl-8-(pyridazin-3-yl)-2,3,4,5-tetrahydro-1H-benzo[c]azepine;
5-(4-fluorophenoxy)-2-methyl-8-(1H-pyrazol-4-yl)-2,3,4,5-tetrahydro-1H-benzo[c]azepine;
6-(5-(4-fluorophenoxy)-2-methyl-2,3,4,5-tetrahydro-1H-benzo[c]azepin-8-yl)pyridazin-3-amine;
5-(4-fluorophenoxy)-2-methyl-8-(pyrimidin-2-yl)-2,3,4,5-tetrahydro-1H-benzo[c]azepine;
5-(4-fluorophenoxy)-2-methyl-8-(pyrimidin-5-yl)-2,3,4,5-tetrahydro-1H-benzo[c]azepine;
5-(4-fluorophenoxy)-2-methyl-8-(pyrazin-2-yl)-2,3,4,5-tetrahydro-1H-benzo[c]azepine;

6-(5-(4-fluorophenoxy)-2-methyl-2,3,4,5-tetrahydro-1H-benzo[c]azepin-8-yl)pyridin-2-amine;

6-(5-(4-fluorophenoxy)-2-methyl-2,3,4,5-tetrahydro-1H-benzo[c]azepin-8-yl)pyridazin-3(2H)-one;

5-(4-fluorophenoxy)-2-methyl-8-(4-(methylsulfonyl)phenyl)-2,3,4,5-tetrahydro-1H-benzo[c]azepine;

2-(5-(4-fluorophenoxy)-2-methyl-2,3,4,5-tetrahydro-1H-benzo[c]azepin-8-yl)benzonitrile;

8-([1,2,4]triazolo[1,5-a]pyridin-6-yl)-5-(4-fluorophenoxy)-2-methyl-2,3,4,5-tetrahydro-1H-benzo[c]azepine;

8-([1,2,4]triazolo[4,3-a]pyridin-6-yl)-5-(4-fluorophenoxy)-2-methyl-2,3,4,5-tetrahydro-1H-benzo[c]azepine;

1-(5-(4-fluorophenoxy)-2-methyl-2,3,4,5-tetrahydro-1H-benzo[c]azepin-8-yl)pyridin-2(1H)-one;

8-(4-(ethylsulfonyl)piperazin-1-yl)-5-(4-fluorophenoxy)-2-methyl-2,3,4,5-tetrahydro-1H-benzo[c]azepine;

5-(3,4-difluorophenoxy)-2-methyl-8-(pyridazin-3-yl)-2,3,4,5-tetrahydro-1H-benzo[c]azepine;

5-(2,4-difluorophenoxy)-2-methyl-8-(pyridazin-3-yl)-2,3,4,5-tetrahydro-1H-benzo[c]azepine;

5-(2-chlorophenoxy)-2-methyl-8-(pyridazin-3-yl)-2,3,4,5-tetrahydro-1H-benzo[c]azepine;

5-(2-chlorophenoxy)-2-methyl-8-(1H-pyrazol-4-yl)-2,3,4,5-tetrahydro-1H-benzo[c]azepine;

6-(5-(2-chlorophenoxy)-2-methyl-2,3,4,5-tetrahydro-1H-benzo[c]azepin-8-yl)pyridazin-3-amine;

5-(2-chlorophenoxy)-2-methyl-8-(pyrimidin-2-yl)-2,3,4,5-tetrahydro-1H-benzo[c]azepine;

5-(2-chlorophenoxy)-2-methyl-8-(pyrimidin-5-yl)-2,3,4,5-tetrahydro-1H-benzo[c]azepine;

5-(2-chlorophenoxy)-2-methyl-8-(pyrazin-2-yl)-2,3,4,5-tetrahydro-1H-benzo[c]azepine;

6-(5-(2-chlorophenoxy)-2-methyl-2,3,4,5-tetrahydro-1H-benzo[c]azepin-8-yl)pyridin-2-amine;

6-(5-(2-chlorophenoxy)-2-methyl-2,3,4,5-tetrahydro-1H-benzo[c]azepin-8-yl)pyridazin-3(2H)-one;

5-(2-chlorophenoxy)-2-methyl-8-(4-(methylsulfonyl)phenyl)-2,3,4,5-tetrahydro-1H-benzo[c]azepine;

2-(5-(2-chlorophenoxy)-2-methyl-2,3,4,5-tetrahydro-1H-benzo[c]azepin-8-yl)benzonitrile;

8-([1,2,4]triazolo[1,5-a]pyridin-6-yl)-5-(2-chlorophenoxy)-2-methyl-2,3,4,5-tetrahydro-1H-benzo[c]azepine;

1-(5-(2-chlorophenoxy)-2-methyl-2,3,4,5-tetrahydro-1H-benzo[c]azepin-8-yl)pyridin-2(1H)-one;

5-(2-chlorophenoxy)-8-(4-(ethylsulfonyl)piperazin-1-yl)-2-methyl-2,3,4,5-tetrahydro-1H-benzo[c]azepine;

5-(3-chlorophenoxy)-2-methyl-8-(pyridazin-3-yl)-2,3,4,5-tetrahydro-1H-benzo[c]azepine;

5-(3-chlorophenoxy)-2-methyl-8-(1H-pyrazol-4-yl)-2,3,4,5-tetrahydro-1H-benzo[c]azepine;

6-(5-(3-chlorophenoxy)-2-methyl-2,3,4,5-tetrahydro-1H-benzo[c]azepin-8-yl)pyridazin-3-amine;

5-(3-chlorophenoxy)-2-methyl-8-(pyrimidin-2-yl)-2,3,4,5-tetrahydro-1H-benzo[c]azepine;

5-(3-chlorophenoxy)-2-methyl-8-(pyrimidin-5-yl)-2,3,4,5-tetrahydro-1H-benzo[c]azepine;

5-(3-chlorophenoxy)-2-methyl-8-(pyrazin-2-yl)-2,3,4,5-tetrahydro-1H-benzo[c]azepine;

6-(5-(3-chlorophenoxy)-2-methyl-2,3,4,5-tetrahydro-1H-benzo[c]azepin-8-yl)pyridin-2-amine;

6-(5-(3-chlorophenoxy)-2-methyl-2,3,4,5-tetrahydro-1H-benzo[c]azepin-8-yl)pyridazin-3(2H)-one;

5-(3-chlorophenoxy)-2-methyl-8-(4-(methylsulfonyl)phenyl)-2,3,4,5-tetrahydro-1H-benzo[c]azepine;

2-(5-(3-chlorophenoxy)-2-methyl-2,3,4,5-tetrahydro-1H-benzo[c]azepin-8-yl)benzonitrile;

8-([1,2,4]triazolo[1,5-a]pyridin-6-yl)-5-(3-chlorophenoxy)-2-methyl-2,3,4,5-tetrahydro-1H-benzo[c]azepine;

1-(5-(3-chlorophenoxy)-2-methyl-2,3,4,5-tetrahydro-1H-benzo[c]azepin-8-yl)pyridin-2(1H)-one;

5-(3-chlorophenoxy)-8-(4-(ethylsulfonyl)piperazin-1-yl)-2-methyl-2,3,4,5-tetrahydro-1H-benzo[c]azepine;

5-(4-chlorophenoxy)-2-methyl-8-(pyridazin-3-yl)-2,3,4,5-tetrahydro-1H-benzo[c]azepine;

2-methyl-8-(pyridazin-3-yl)-5-(p-tolyloxy)-2,3,4,5-tetrahydro-1H-benzo[c]azepine;

2-methyl-8-(pyridazin-3-yl)-5-(4-(trifluoromethoxy)phenoxy)-2,3,4,5-tetrahydro-1H-benzo[c]azepine;

4-(2-methyl-8-(pyridazin-3-yl)-2,3,4,5-tetrahydro-1H-benzo[c]azepin-5-yloxy)benzonitrile;

2-methyl-8-(pyridazin-3-yl)-5-(4-(trifluoromethyl)phenoxy)-2,3,4,5-tetrahydro-1H-benzo[c]azepine;

6-(2-methyl-5-(4-(trifluoromethyl)phenoxy)-2,3,4,5-tetrahydro-1H-benzo[c]azepin-8-yl)pyridazin-3-amine;

2-methyl-8-(pyridazin-3-yl)-5-(o-tolyloxy)-2,3,4,5-tetrahydro-1H-benzo[c]azepine;

6-(2-methyl-5-(o-tolyloxy)-2,3,4,5-tetrahydro-1H-benzo[c]azepin-8-yl)pyridazin-3-amine;

5-(2-methoxyphenoxy)-2-methyl-8-(pyridazin-3-yl)-2,3,4,5-tetrahydro-1H-benzo[c]azepine;

6-(5-(2-methoxyphenoxy)-2-methyl-2,3,4,5-tetrahydro-1H-benzo[c]azepin-8-yl)pyridazin-3-amine;

5-(3,5-difluorophenoxy)-2-methyl-8-(pyridazin-3-yl)-2,3,4,5-tetrahydro-1H-benzo[c]azepine;

5-(3,5-difluorophenoxy)-2-methyl-8-(1H-pyrazol-4-yl)-2,3,4,5-tetrahydro-1H-benzo[c]azepine;

6-(5-(3,5-difluorophenoxy)-2-methyl-2,3,4,5-tetrahydro-1H-benzo[c]azepin-8-yl)pyridazin-3-amine;

5-(3,5-difluorophenoxy)-2-methyl-8-(pyrimidin-2-yl)-2,3,4,5-tetrahydro-1H-benzo[c]azepine;

5-(3,5-difluorophenoxy)-2-methyl-8-(pyrimidin-5-yl)-2,3,4,5-tetrahydro-1H-benzo[c]azepine;

5-(3,5-difluorophenoxy)-2-methyl-8-(pyrazin-2-yl)-2,3,4,5-tetrahydro-1H-benzo[c]azepine;

6-(5-(3,5-difluorophenoxy)-2-methyl-2,3,4,5-tetrahydro-1H-benzo[c]azepin-8-yl)pyridin-2-amine;

6-(5-(3,5-difluorophenoxy)-2-methyl-2,3,4,5-tetrahydro-1H-benzo[c]azepin-8-yl)pyridazin-3(2H)-one;

5-(3,5-difluorophenoxy)-2-methyl-8-(4-(methylsulfonyl)phenyl)-2,3,4,5-tetrahydro-1H-benzo[c]azepine;

2-(5-(3,5-difluorophenoxy)-2-methyl-2,3,4,5-tetrahydro-1H-benzo[c]azepin-8-yl)benzonitrile;

8-([1,2,4]triazolo[1,5-a]pyridin-6-yl)-5-(3,5-difluorophenoxy)-2-methyl-2,3,4,5-tetrahydro-1H-benzo[c]azepine;

1-(5-(3,5-difluorophenoxy)-2-methyl-2,3,4,5-tetrahydro-1H-benzo[c]azepin-8-yl)pyridin-2(1H)-one;

5-(3,5-difluorophenoxy)-8-(4-(ethylsulfonyl)piperazin-1-yl)-2-methyl-2,3,4,5-tetrahydro-1H-benzo[c]azepine;

5-(3,4-dichlorophenoxy)-2-methyl-8-(pyridazin-3-yl)-2,3,4,5-tetrahydro-1H-benzo[c]azepine;

2-methyl-8-(pyridazin-3-yl)-5-(pyridin-3-yloxy)-2,3,4,5-tetrahydro-1H-benzo[c]azepine;

2-methyl-5-(naphthalen-2-yloxy)-8-(pyridazin-3-yl)-2,3,4,5-tetrahydro-1H-benzo[c]azepine;

2-methyl-5-(naphthalen-1-yloxy)-8-(pyridazin-3-yl)-2,3,4,5-tetrahydro-1H-benzo[c]azepine;

2-methyl-8-(pyridazin-3-yl)-5-(quinolin-7-yloxy)-2,3,4,5-tetrahydro-1H-benzo[c]azepine;

5-(4-chlorophenoxy)-2-methyl-8-(pyridazin-3-yl)-2,3,4,5-tetrahydro-1H-benzo[c]azepine;

5-(3-fluorophenoxy)-2-methyl-8-(pyridazin-3-yl)-2,3,4,5-tetrahydro-1H-benzo[c]azepine;

2-methyl-5-(4-(trifluoromethyl)phenoxy)-2,3,4,5-tetrahydro-1H-benzo[c]azepine
8-([1,2,4]triazolo[1,5-a]pyridin-6-yl)-5-(4-fluorophenoxy)-2-methyl-2,3,4,5-tetrahydro-1H-benzo[c]azepine;
8-([1,2,4]triazolo[4,3-a]pyridin-6-yl)-5-(4-fluorophenoxy)-2-methyl-2,3,4,5-tetrahydro-1H-benzo[c]azepine;
1-(5-(4-fluorophenoxy)-2-methyl-2,3,4,5-tetrahydro-1H-benzo[c]azepin-8-yl)pyridin-2(1H)-one;
8-(6-methylpyridazin-3-yl)-5-phenoxy-2,3,4,5-tetrahydro-1H-benzo[c]azepine;
2-(5-(3,5-difluorophenoxy)-2,3,4,5-tetrahydro-1H-benzo[c]azepin-8-yl)-[1,2,4]triazolo[4,3-a]pyridin-3(2H)-one;
8-([1,2,4]triazolo[1,5-a]pyridin-6-yl)-5-(3,5-difluorophenoxy)-2,3,4,5-tetrahydro-1H-benzo[c]azepine;
8-(6-(difluoromethoxy)pyridazin-3-yl)-5-(3,5-difluorophenoxy)-2,3,4,5-tetrahydro-1H-benzo[c]azepine;
2-(5-(3,5-difluorophenoxy)-2,3,4,5-tetrahydro-1H-benzo[c]azepin-8-yl)pyridazin-3(2H)-one;
8-([1,2,4]triazolo[4,3-a]pyridin-6-yl)-5-(3,5-difluorophenoxy)-2-methyl-2,3,4,5-tetrahydro-1H-benzo[c]azepine;
8-(6-(difluoromethoxy)pyridazin-3-yl)-5-(3,5-difluorophenoxy)-2-methyl-2,3,4,5-tetrahydro-1H-benzo[c]azepine;
2-(5-(3,5-difluorophenoxy)-2-methyl-2,3,4,5-tetrahydro-1H-benzo[c]azepin-8-yl)-[1,2,4]triazolo[4,3-a]pyridin-3(2H)-one;
4-(2-methyl-5-phenoxy-2,3,4,5-tetrahydro-1H-benzo[c]azepin-8-yl)benzamide;
4-(5-(3,5-difluorophenoxy)-2-methyl-2,3,4,5-tetrahydro-1H-benzo[c]azepin-8-yl)benzonitrile;
5-(2,3-difluorophenoxy)-2-methyl-8-(pyridazin-3-yl)-2,3,4,5-tetrahydro-1H-benzo[c]azepine;
3-(2-methyl-8-(pyridazin-3-yl)-2,3,4,5-tetrahydro-1H-benzo[c]azepin-5-yloxy)benzonitrile;
5-(2,5-difluorophenoxy)-2-methyl-8-(pyridazin-3-yl)-2,3,4,5-tetrahydro-1H-benzo[c]azepine; and
5-(2,6-difluorophenoxy)-2-methyl-8-(pyridazin-3-yl)-2,3,4,5-tetrahydro-1H-benzo[c]azepine.

Other embodiments of the present invention are compounds of formulae I(A-E) where the carbon atom designated * is in the R configuration.

Other embodiments of the present invention are compounds of formulae I(A-E) where the carbon atom designated * is in the S configuration.

Another embodiment of the present invention is a mixture of stereoisomeric compounds of formulae I(A-E) where * is in the S or R configuration.

Within these embodiments, the selection of a particular preferred substituent at any one of $R^1$-$R^9$ does not affect the selection of a substituent at any of the others of $R^1$-$R^8$. That is, preferred compounds provided herein have any of the preferred substituents at any of the positions. For example, as described hereinabove, $R^1$ is preferably $C_1$-$C_6$ alkyl; the selection of $R^1$ as any one of $C_1$, $C_2$, $C_3$, $C_4$, $C_5$, or $C_6$ alkyl, does not limit the choice of $R^2$ in particular to any one of H, $C_1$-$C_6$ alkyl, or $C_1$-$C_6$ haloalkyl. Rather, for $R^1$ as any of $C_1$, $C_2$, $C_3$, $C_4$, $C_5$, or $C_6$ alkyl, $R^2$ is any of H, $C_1$, $C_2$, $C_3$, $C_4$, $C_5$, or $C_6$ alkyl or $C_1$, $C_2$, $C_3$, $C_4$, $C_5$, or $C_6$ haloalkyl. Similarly, the selection of $R^2$ as any of H, $C_1$, $C_2$, $C_3$, $C_4$, $C_5$, or $C_6$ alkyl or $C_1$, $C_2$, $C_3$, $C_4$, $C_5$, or $C_6$ haloalkyl does not limit the selection of $R^3$ in particular to any one of H, halogen, —$OR^{11}$, —$S(O)_n$ $R^{12}$, —CN, —$C(O)R^{12}$, $C_1$-$C_6$ alkyl, $C_3$-$C_6$ cycloalkyl, $C_4$-$C_7$ cycloalkylalkyl, or substituted $C_4$-$C_7$ cycloalkylalkyl.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

Another embodiment of the present invention is a mixture of compounds of formulae I(A-E) where the compound of formulae I(A-E) is radiolabeled, i.e., where one or more of the atoms described are replaced by a radioactive isotope of that atom (e.g., C replaced by $^{14}$C and H replaced by $^{3}$H). Such compounds have a variety of potential uses, e.g., as standards and reagents in determining the ability of a potential pharmaceutical to bind to neurotransmitter proteins.

Another embodiment of the present invention is a pharmaceutical composition containing a therapeutically effective amount of the compound of formulae I(A-E) and a pharmaceutically acceptable carrier.

Another aspect of the present invention relates to a method of treating a disorder which is created by or is dependent upon decreased availability of serotonin, norepinephrine, or dopamine. The method involves administering to a patient in need of such treatment a therapeutically effective amount of a compound of formulae I(A-E) or a pharmaceutically acceptable salt thereof. The method of the present invention is capable of treating subjects afflicted with various neurological and psychiatric disorders including, without limitation: lower back pain, attention deficit hyperactivity disorder (ADHD), cognition impairment, anxiety disorders especially generalized anxiety disorder (GAD), panic disorder, bipolar disorder, also known as manic depression or manic-depressive disorder, obsessive compulsive disorder (OCD), post-traumatic stress disorder (PTSD), acute stress disorder, social phobia, simple phobias, pre-menstrual dysphoric disorder (PMDD), social anxiety disorder (SAD), major depressive disorder (MDD), postnatal depression, dysthymia, depression associated with Alzheimer's disease, Parkinson's disease, or psychosis, supranuclear palsy, eating disorders, especially obesity, anorexia nervosa, bulimia nervosa, and binge eating disorder, analgesia, substance abuse disorders (including chemical dependencies) such as nicotine addiction, cocaine addiction, alcohol and amphetamine addiction, Lesch-Nyhan syndrome, neurodegenerative diseases such as Parkinson's disease, late luteal phase syndrome or narcolepsy, psychiatric symptoms such as anger, rejection sensitivity, movement disorders such as extrapyramidal syndrome, Tic disorders and restless leg syndrome (RLS), tardive dyskinesia, supranuclear palsy, sleep related eating disorder (SRED), night eating syndrome (NES), stress urinary incontinence (SUI), migraine, neuropathic pain, especially diabetic neuropathy, fibromyalgia syndrome (FS), chronic fatigue syndrome (CFS), sexual dysfunction, especially premature ejaculation and male impotence, and thermoregulatory disorders (e.g., hot flashes associated with menopause).

The compounds provided herein are particularly useful in the treatment of these and other disorders due, at least in part, to their ability to selectively bind to the transporter proteins for certain neurochemicals with a greater affinity than to the transporter proteins for other neurochemicals.

In another embodiment of the present invention, the above method further involves administering a therapeutically effective amount of a serotonin 1A receptor antagonist or a pharmaceutically acceptable salt thereof. Suitable serotonin 1A receptor antagonists include WAY 100135 and spiperone. WAY 100135 (N-(t-butyl)-3-[a-(2-methoxyphenyl)piperazin-1-yl]-2 phenylpropanamide) is disclosed as having an affinity for the serotonin 1A receptor in U.S. Pat. No. 4,988,814 to Abou-Gharbia et al., which is hereby incorporated by reference in its entirety. Also, Cliffe et al., *J Med Chem* 36:1509-10 (1993), which is hereby incorporated by reference in its entirety, showed that the compound is a serotonin 1A antagonist. Spiperone (8-[4-(4-fluorophenyl)-4-oxobutyl]-1-phenyl-1,3,8-triazaspiro[4,5]decan-4-one) is a well-known compound and is disclosed in U.S. Pat. Nos. 3,155,669 and 3,155,670, which are hereby incorporated by reference in their entirety. The activity of spiperone as a serotonin 1A antagonist is described in Middlemiss et al., *Neurosc and Biobehav Rev.* 16:75-82 (1992), which is hereby incorporated by reference in its entirety.

In another embodiment of the present invention, the above method further involves administering a therapeutically effective amount of a selective neurokinin-1 receptor antagonist or pharmaceutically acceptable salt thereof. Neurokinin-1 receptor antagonists that can be used in combination with the compound of formulae I(A-E) in the present invention are fully described, for example, in U.S. Pat. Nos. 5,373,003, 5,387,595, 5,459,270, 5,494,926, 5,162,339, 5,232,929, 5,242,930, 5,496,833, and 5,637,699; PCT International Patent Publication Nos. WO 90/05525, 90/05729, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and in U.K. Patent Application Nos. 2 266 529, 2 268 931, 2 269 170, 2 269 590, 2 271 774, 2 292 144, 2 293168, 2 293 169, and 2 302 689; European Patent Publication Nos. EP 0 360 390, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 699 674, 0 707 006, 0 708 101, 0 709 375, 0 709 376, 0 714 891, 0 723 959, 0 733 632 and 0 776 893, which are hereby incorporated by reference in their entirety. The preparations of such compounds are fully described in the aforementioned patents and publications.

In another embodiment of the present invention, the above method further involves administering a therapeutically effective amount of a norepinephrine precursor or a pharmaceutically acceptable salt thereof. Suitable norepinephrine precursors include L-tyrosine and L-phenylalanine Another aspect of the present invention is a method of inhibiting synaptic norepinephrine uptake in a patient in need thereof. The method involves administering a therapeutically effective inhibitory amount of a compound of formulae I(A-E).

Another aspect of the present invention is a method of inhibiting synaptic serotonin uptake in a patient in need thereof. The method involves administering a therapeutically effective inhibitory amount of a compound of formulae I(A-E).

Another aspect of the present invention is a method of inhibiting synaptic dopamine uptake in a patient in need thereof. The method involves administering a therapeutically effective inhibitory amount of a compound of formulae I(A-E).

Another aspect of the present invention is a therapeutic method described herein, where the (+)-stereoisomer of the compound of formulae I(A-E) is employed.

Another aspect of the present invention is a therapeutic method described herein, where the (−)-stereoisomer of the compound of formulae I(A-E) is employed.

Another aspect of the present invention is a kit comprising a compound of formulae I(A-E) and at least one compound selected from the group consisting of: a serotonin 1A receptor antagonist compound, a selective neurokinin-1 receptor antagonist compound, and a norepinephrine precursor compound.

Another aspect of the present invention relates to a method of treating a disorder referred to in the above-mentioned embodiments in a patient in need thereof. The method involves inhibiting synaptic serotonin and norepinephrine uptake by administering a therapeutically effective inhibitory amount of the compound of formulae I(A-E) which functions as both a dual acting serotonin and norepinephrine uptake inhibitor.

Another aspect of the present invention relates to a method of treating a disorder referred to in the above-mentioned embodiments in a patient in need thereof. The method involves inhibiting synaptic serotonin and dopamine uptake by administering a therapeutically effective inhibitory amount of the compound of formulae I(A-E) which functions as both a dual acting serotonin and dopamine uptake inhibitor.

Another aspect of the present invention relates to a method of treating a disorder referred to in the above-mentioned embodiments in a patient in need thereof. The method involves inhibiting synaptic dopamine and norepinephrine uptake by administering a therapeutically effective inhibitory amount of the compound of formulae I(A-E) which functions as both a dual acting dopamine and norepinephrine uptake inhibitor.

Another aspect of the present invention relates to a method of treating a disorder referred to in the above-mentioned embodiments in a patient in need thereof. The method involves inhibiting synaptic norepinephrine, dopamine and serotonin uptake by administering a therapeutically effective inhibitory amount of the compound of formulae I(A-E) which functions as a triple acting norepinephrine, dopamine, and serotonin uptake inhibitor.

Another aspect of the present invention relates to a method for inhibiting serotonin uptake in mammals. The method involves administering to a mammal requiring increased neurotransmission of serotonin a pharmaceutically effective amount of the compound of formulae I(A-E).

Another aspect of the present invention relates to a method for inhibiting dopamine uptake in humans. The method involves administering to a human requiring increased neurotransmission of dopamine a pharmaceutically effective amount of the compound of formulae I(A-E).

Another aspect of the present invention relates to a method for inhibiting norepinephrine uptake in humans. The method involves administering to a human requiring increased neurotransmission of norepinephrine a pharmaceutically effective amount of the compound of formulae I(A-E).

Another aspect of the present invention relates to a method of suppressing the desire of humans to smoke. The method involves administering to a human in need of such suppression an effective dose, to relieve the desire to smoke, of the compound of formulae I(A-E).

Another aspect of the present invention relates to a method of suppressing the desire of humans to consume alcohol. The method involves administering to a human in need of such suppression an effective dose, to relieve the desire to consume alcohol, of the compound of formulae I(A-E).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example those described by Larock, R. C., *Comprehensive Organic Transformations*, VCH publishers, (1989), which is hereby incorporated by reference in its entirety.

A compound of formulae I(A-E), including a group containing one or more nitrogen ring atoms, may be converted to the corresponding compound where one or more nitrogen ring atom of the group is oxidized to an N-oxide, preferably by reacting with a peracid, for example, peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxyl, amino, imino, thio, or carboxy groups, where these are desired in the final product, to avoid their unwanted participation in the reactions. Conventional protecting groups may be used in accordance with standard practice; for examples, see Green, *Protective Groups in Organic Chemistry*, John Wiley and Sons (1991) and McOmie, *Protective Groups in Organic Chemistry*, Plenum Press (1973), which are hereby incorporated by reference in their entirety.

In the reaction schemes described hereinafter, the synthesis of tetrahydrobenzazepines of the formulae I(A-E) is described.

The novel tetrahydrobenzazepine reuptake inhibitors of formula I of the present invention can be prepared by the general scheme outlined below (Scheme 1).

Scheme 1

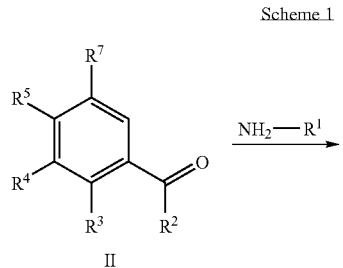

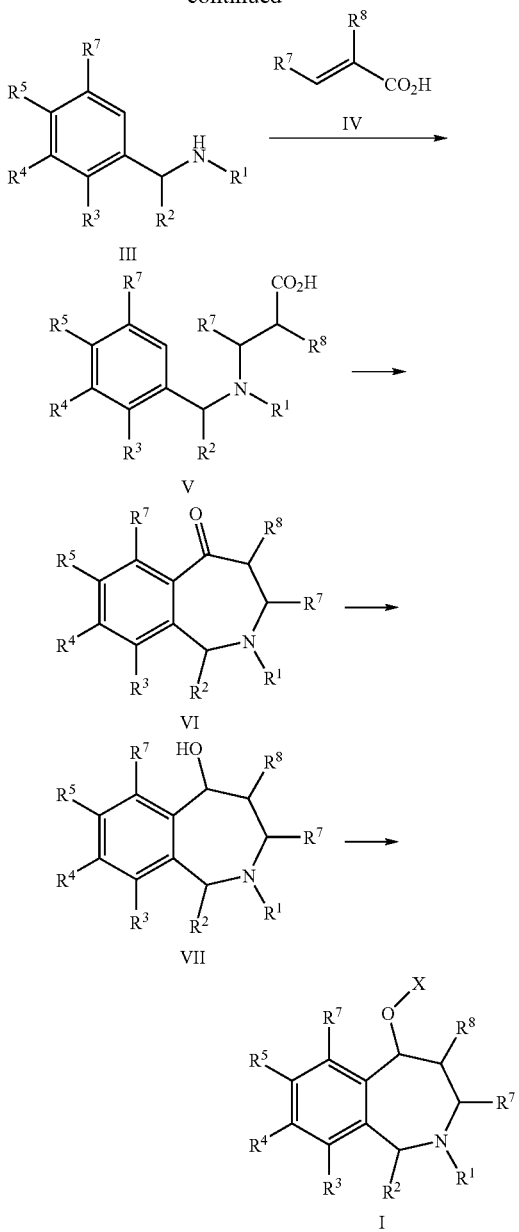

The $R^1$-substituted N-benzyl amines of formula (III) may be purchased from commercial sources, or alternatively, obtained from a simple reductive amination protocol. Thus, carbonyl containing compounds of formula (II) may be treated with $H_2N$—$R^1$ in lower alkyl alcoholic solvents (preferably methanol or ethanol) at temperatures at or below room temperature. The resulting imine may be reduced most commonly with alkali earth borohydrides (preferably sodium borohydride) to provide the desired amine intermediates of formula (III). Treatment of compounds of formula (III) with a base such as, but not limited to pyridine, followed by acrylic acid derivatives of formula (IV) give compounds of formula (V). The acids with the formula (V) may be cyclized to give the corresponding 5-benzazepinone of the formula (VI) on treatment with a strong acid such as, but not limited to, polyphosphoric acid or Eaton's reagent. Alternatively, acids with the formula (V) may be converted to the correspondent acyl chlorides using methods familiar to one skilled in the art of organic synthesis. Upon treatment with a Lewis acid, such as, but not limited to aluminum chloride, the acyl chlorides cyclize to give 5-benzazepinone of the formula (VI). The 5-benzazepinone of the formula (VI) may be reduced to the secondary alcohol intermediates (VII) on reaction with reducing agents such as, but not limited to, sodium borohydride in a lower alkyl alcohol solvent. Compounds of formula (VII) may be converted to compounds of formula (I) by treating with phenols X—OH under Mitsunobu Reaction conditions that are familiar to one skilled in the art of organic synthesis. The typical Mitsunobu Reaction conditions are 1,1'-(azodicarbonyl)dipiperidine ("ADDP") and (n-Bu)$_3$P in THF. Alternatively, compounds of formula (VII) may be converted to compounds of formula (I) by treating with X—Y (Y=Cl, Br, I) under basic conditions such as, but not limited to sodium hydride or alkali metal alkoxides in solvents such as THF.

The compounds of formula (I; $R^4$=aryl, heteroaryl) of the present invention may be prepared from the corresponding 8-methoxy, 8-Cl, 8-Br, or 8-I tetrahydrobenzazepine of formula (I; $R^4$=OCH$_3$, Cl, Br, I). The 8-methoxy tetrahydrobenzazepine (I; $R^4$=OCH$_3$) may be converted to the corresponding phenol of formula (I; $R^4$=OH) on treatment with a strong acid or a Lewis acid, such as, but not limited to, hydrobromic acid or boron tribromide. Alternatively, the phenol of formula I ($R^4$=OH) may be obtained from the corresponding 8-methoxy tetrahydrobenzazepine of formula I ($R^4$=OCH$_3$) on treatment with the sodium salt of an alkyl thiol, preferably ethane thiol. The phenol intermediate of formula (I; $R^4$=OH) may be converted into the corresponding triflate of formula (I; $R^4$=OSO$_2$CF$_3$) on treatment with a triflating reagent such as, but not limited to, trifluoromethanesulfonic anhydride, in the presence of a base, such as, but not limited to, triethylamine or pyridine. The reaction is carried out in an inert solvent, such as, but not limited to dichloromethane, at temperatures ranging from 0° C. to room temperature. Treatment of compounds of formula (I; $R^4$=Cl, Br, I, OSO$_2$CF$_3$) with aryl or heteroaryl boronic acids or aryl or heteroaryl boronic acid esters, of formula $R^4$—Z where Z is equivalent to B(OH)$_2$ or B(OR$^a$)(OR$^b$) (where $R^a$ and $R^b$ are lower alkyl, i.e., C$_1$-C$_6$, or taken together, $R^a$ and $R^b$ are lower alkylene, i.e., C$_2$-C$_{12}$) and $R^4$ is the corresponding aryl or heteroaryl group in the presence of a metal catalyst with or without a base in an inert solvent gives benzazepine compounds of formula (I; $R^4$=aryl, heteroaryl). Metal catalysts include, but are not limited to, salts or phosphine complexes of Cu, Pd, or Ni (e.g., Cu(OAc)$_2$, PdCl$_2$ (PPh$_3$)$_2$, NiCl$_2$ (PPh$_3$)$_2$, Pd(PPh$_3$)$_4$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides, alkali metal alkoxides, alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described by Gao et al., *Tetrahedron*, 50:979-988 (1994), which is hereby incorporated by reference in its entirety.

It will also be appreciated by one skilled in the art that compounds of formula (I; $R^4$=Cl, Br, I, OSO$_2$CF$_3$) may be converted to the boronic acid or boronate ester and subsequently treated with the desired optionally substituted aryl or heteroaryl halide in discrete steps or in tandem as described by Baudoin et al., *J. Org. Chem.* 67:1199-1207 (2002), which is hereby incorporated by reference in its entirety.

The compounds of formula (I; $R^4$=—NR$^{10}$R$^{11}$, —NR$^{12}$C (O)R$^{13}$) of the present invention may be prepared from the compounds of formula (I; $R^4$=Cl, Br, I, OSO$_2$CF$_3$) on reaction with an appropriate amine, amide or lactam, in the presence of a metal catalyst, with or without a base in an inert solvent. Metal catalysts include, but are not limited to, salts or complexes of Cu, Pd, or Ni (e.g., CuI, Cu(OAc)$_2$, PdCl$_2$ (dppf), NiCl(OAc)$_2$, Ni(COD)$_2$). Bases may include, but are not limited to, alkali metal carbonates, alkali metal hydrides, alkali metal alkoxides (preferably, sodium tert-butoxide), and alkali metal bis(trialkylsilyl)amides (preferably, lithium bis (trimethylsilyl)amide). A supporting ligand, such as, but not limited to L-proline or dimethylethylenediamine is often used. Inert solvents may include, but are not limited to, cyclic ethers (preferably, tetrahydrofuran or 1,4-dioxane), N,N-dialkylformamides (preferably, dimethylformamide), dialkylsulfoxides (preferably, dimethylsulfoxide), or aromatic hydrocarbons (preferably, benzene or toluene). Preferred reaction temperatures range from room temperature up to the boiling point of the solvent employed. The reactions may be run in conventional glassware or in a sealed reaction vessel.

It will also be appreciated by one skilled in the art that the secondary alcohols of formula (VII; $R^4$=Cl, Br, I) may be protected as, but not limited to, silyl ethers such as tert-butyldimethylsilyl ether by methods that that are familiar to one skilled in the art of organic synthesis. The silyl ether derivatives of formula (VII; $R^4$=Cl, Br, I) may then be converted to silyl ethers derivative of formula (VII; $R^4$=aryl, heteroaryl, —NR$^{10}$R$^{11}$, —NR$^{12}$C(O)R$^{13}$) by the aforementioned methods. The silyl group can be removed by treatment with tetrabutyl ammonium fluoride to give compounds of formula (VII). Compounds of formula (VII) may be converted to compounds of formula (I) by the aforementioned methods.

Compounds of formula I(A-E) may be obtained in enantiomerically pure (R) and (S) form by crystallization with chiral salts as well known to one skilled in the art, or alternatively, may be isolated through chiral HPLC employing commercially available chiral columns. Compounds of formula (VII) or the ether derivatives, such as the tert-butyldimethylsilyl ethers of compounds of formula (VII) could also be obtained as enantiomerically pure (R) and (S) form by crystallization with chiral salts as well known to one skilled in the art, or alternatively, may be isolated through chiral HPLC employing commercially available chiral columns.

It will be appreciated that compounds according to the present invention may contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formulae I(A-E) hereinabove. Such isomers can be separated from their mixtures, by the application or adaptation of known methods, for example chromatographic techniques and recrystallization techniques, or they are separately prepared from the appropriate isomers of their intermediates.

Radiolabelled compounds of the invention are synthesized by a number of means well known to those of ordinary skill in the art, e.g., by using starting materials incorporating therein one or more radioisotopes. Compounds of the present invention where a stable radioisotope, such as carbon-14, tritium, iodine-121, or another radioisotope, has been introduced synthetically are useful diagnostic agents for identifying areas of the brain or central nervous system that may be affected by disorders where norepinephrine, dopamine, or serotonin transporters and their uptake mechanism are implicated.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining two or more active ingredients useful in treating the disease. A kit may provide (alone or in combination with a pharmaceutically acceptable diluent or carrier) the compounds of formulae I(A-E) and the additional active ingredient (alone or in combination with diluent or carrier) selected from a serotonin 1A receptor antagonist, a selective neurokinin-1 receptor antagonist, and a norepinephrine precursor.

In practice, the compounds of the present invention may generally be administered parenterally, intravenously, subcutaneously, intramuscularly, colonically, nasally, intraperitoneally, rectally, or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol, and chloroform or mixtures thereof may also be used.

For parenteral administration, emulsions, suspensions or solutions of the products according to the invention in vegetable oil, for example sesame oil, groundnut oil, or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the present invention may be prepared by conventional means. For example, compounds of the present invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formulae I(A-E).

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.5 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The present invention provides compounds which inhibit synaptic norepinephrine, dopamine, and serotonin uptake and are, therefore, believed to be useful in treating a disorder which is created by or is dependent upon decreased availability of serotonin, norepinephrine or dopamine. Although the compounds of formulae I(A-E), inhibit synaptic norepinephrine, dopamine, and serotonin uptake, in any individual compound, these inhibitory effects may be manifested at the same or vastly different concentrations or doses. As a result, some compounds of formulae I(A-E), are useful in treating such a disorder at doses at which synaptic norepinephrine uptake may be substantially inhibited but at which synaptic serotonin uptake or dopamine uptake is not substantially inhibited, or vice versa. Also, some compounds of formulae I(A-E), are useful in treating such a disorder at doses at which synaptic dopamine uptake may be substantially inhibited but at which synaptic norepinephrine or serotonin uptake is not substantially inhibited, or vice versa. And, conversely, some compounds of formulae I(A-E), are useful in treating such a disorder at doses at which synaptic serotonin uptake may be substantially inhibited but at which synaptic norepinephrine or dopamine uptake is not substantially inhibited, or vice versa. Other compounds of formulae I(A-E), are useful in treating such a disorder at doses at which synaptic norepinephrine, dopamine, and serotonin uptake are substantially inhibited.

The present invention provides compounds where the inhibitory effects on serotonin and norepinephrine uptake occurs at similar or even the same concentrations of these compounds, while the effects on inhibition of dopamine uptake occurs at vastly different concentrations or doses. As a result, some compounds of formulae I(A-E), are useful in treating such a disorder at doses at which synaptic serotonin and norepinephrine uptake may be substantially inhibited but at which synaptic dopamine uptake is not substantially inhibited, or vice versa.

The present invention provides compounds where the inhibitory effects on serotonin and dopamine uptake occurs at similar or even the same concentrations of these compounds while the effects on inhibition of norepinephrine uptake occurs at vastly different concentrations or doses. As a result, some compounds of formulae I(A-E), are useful in treating such a disorder at doses at which synaptic serotonin and dopamine uptake may be substantially inhibited but at which synaptic norepinephrine uptake is not substantially inhibited, or vice versa.

The present invention provides compounds where the inhibitory effects on norepinephrine and dopamine uptake occurs at similar or even the same concentrations of these compounds while the effects on inhibition of dopamine uptake occurs at vastly different concentrations or doses. As a result, some compounds of formulae I(A-E) are useful in treating such a disorder at doses at which synaptic norepinephrine and dopamine uptake may be substantially inhibited but at which synaptic serotonin uptake is not substantially inhibited, or vice versa.

The present invention provides compounds where the inhibitory effects on norepinephrine, dopamine and serotonin uptake occur at similar or even the same concentration. As a result, some compounds of formulae I(A-E) are useful in treating such a disorder at doses at which synaptic norepinephrine, dopamine, and serotonin uptake may all be substantially inhibited.

The concentrations or doses at which a test compound inhibits synaptic norepinephrine, dopamine, and serotonin uptake is readily determined by the use of standard assay and techniques well known and appreciated by one of ordinary skill in the art. For example, the degree of inhibition at a particular dose in rats can be determined by the method of Dudley, *J Pharmacol Exp Ther* 217:834-840 (1981), which is hereby incorporated by reference in its entirety.

The therapeutically effective inhibitory dose is one that is effective in substantially inhibiting synaptic norepinephrine uptake, synaptic dopamine uptake, or synaptic serotonin uptake or inhibiting the synaptic uptake of two or more of norepinephrine, dopamine and serotonin uptake. The therapeutically effective inhibitory dose can be readily determined by those skilled in the art by using conventional range finding techniques and analogous results obtained in the test systems described above.

Compounds of this invention provide a particularly beneficial therapeutic index relative to other compounds available for the treatment of similar disorders. Without intending to be limited by theory, it is believed that this is due, at least in part, to some of the compounds having higher binding affinities for one or two of the neurotransmitter transporters, e.g., selectivity towards the norepinephrine transporter protein ("NET") over the transporters for other neurochemicals, e.g., the dopamine transporter protein ("DAT") and the serotonin transporter protein ("SERT").

Other compounds of the present invention may demonstrate selectivity towards the SERT over the transporters for other neurochemicals, e.g., the DAT and the NET.

Still other compounds of the present invention may demonstrate selectivity towards the DAT over the transporters for other neurochemicals, e.g., the SERT and the NET.

Other compounds of the present invention may demonstrate selectivity towards the SERT and the NET over the transporter for other neurochemical, e.g., the DAT.

Still other compounds of the present invention may demonstrate selectivity towards the SERT and the DAT over the transporter for other neurochemical, e.g., the NET.

Still other compounds of the present invention may demonstrate selectivity towards the NET and the DAT over the transporter for other neurochemical, e.g., the SERT.

Finally other compounds possess nearly identical affinity towards the NET, the DAT, and the SERT.

Binding affinities are demonstrated by a number of means well known to ordinarily skilled artisans, including, without limitation, those described in the Examples section hereinbelow. Briefly, for example, protein-containing extracts from cells, e.g., HEK293E cells, expressing the transporter proteins are incubated with radio labelled ligands for the proteins. The binding of the radio ligands to the proteins is reversible in the presence of other protein ligands, e.g., the compounds of the present invention; said reversibility, as described below, provides a means of measuring the compounds' binding affinities for the proteins (Ki or $IC_{50}$). A higher Ki or $IC_{50}$ value for a compound is indicative that the compound has less binding affinity for a protein than is so for a compound with a lower Ki or $IC_{50}$; conversely, lower Ki or $IC_{50}$ values are indicative of greater binding affinities.

Accordingly, the difference in compound selectivity for proteins is indicated by a lower Ki or $IC_{50}$ for the protein for which the compound is more selective, and a higher Ki or $IC_{50}$ for the protein for which the compound is less selective. Thus, the higher the ratio in Ki or $IC_{50}$ values of a compound for protein A over protein B, the greater is the compounds' selectivity for the latter over the former (the former having a higher Ki or $IC_{50}$ and the latter a lower Ki or $IC_{50}$ for that compound). Compounds provided herein possess a wide range of selectivity profiles for the norepinephrine, dopamine, and serotonin transporters as reflected by the ratios of the experimentally determined Ki or $IC_{50}$ values.

Selected compounds ("mono action transporter reuptake inhibitors") of the present invention have potent binding affinity for each of the biogenic amine transporters NET, DAT or SERT. For example, selected compounds of the present invention possess potent (NET Ki or $IC_{50}$<100 nM) and selective binding affinity for NET, where the Ki or $IC_{50}$ ratio of DAT/NET and SERT/NET is greater than 10:1. Other selected compounds of the present invention possess potent (SERT Ki or $IC_{50}$<100 nM) and selective binding affinity for SERT, where the Ki or $IC_{50}$ ratio of NET/SERT and DAT/SERT is greater than 10:1. Other selected compounds of the present invention possess potent (DAT Ki or $IC_{50}$<100 nM) and selective binding affinity for DAT, where the Ki or $IC_{50}$ ratio of NET/DAT and SERT/DAT is greater than 10:1.

Selected compounds ("dual action transporter reuptake inhibitors") of the present invention have potent binding affinity for two of the biogenic amine transporters, NET, DAT or SERT. For example, selected compounds of the present invention possess potent (NET & SERT Ki or $IC_{50}$ values <100 nM) and selective binding affinity for NET and SERT, where the Ki ratio of DAT/NET and DAT/SERT is greater than 10:1 while the Ki or $IC_{50}$ ratio of SERT/NET or NET/SERT is less than 10:1. Other selected compounds of the present invention possess potent (NET & DAT Ki or $IC_{50}$ values <100 nM) and selective binding affinity for NET and DAT, where the Ki ratio of SERT/NET and SERT/DAT is greater than 10:1 while the Ki or $IC_{50}$ ratio of DAT/NET or NET/DAT is less than 10:1. Other selected compounds of this invention possess potent (DAT & SERT Ki or $IC_{50}$ values <100 nM) and selective binding affinity for DAT and SERT, where the Ki or $IC_{50}$ ratio of NET/DAT and SERT/DAT is greater than 10:1 while the Ki or $IC_{50}$ ratio of SERT/NET or NET/SERT is less than 10:1.

Selected compounds ("triple action transporter reuptake inhibitors") of the present invention have potent binding affinity simultaneously for all three of the biogenic amine transporters, NET, DAT or SERT. For example, selected compounds of this invention possess potent (NET, DAT & SERT Ki or $IC_{50}$ values <100 nM) where the Ki or $IC_{50}$ ratios of NET/DAT, NET/SERT, DAT/NET, DAT/SERT, SERT/NET and SERT/DAT are all less than 10:1.

Selected compounds of the present invention have potent binding affinity (Ki or $IC_{50}$ values <100 nM) for one, two, or three of the biogenic amine transporters, NET, DAT and SERT where the Ki or $IC_{50}$ ratios for any of NET/SERT, NET/DAT, DAT/NET, DAT/SERT, SERT/NET, and SERT/DAT fall outside of the bounds defined for the "Mono-, Dual or Triple action transporter reuptake inhibitors" defined above.

Selected compounds of the present invention have less potent binding affinity (Ki or $IC_{50}$ values between 100 nM and 1000 nM) for one, two, or three of the biogenic amine transporters, NET, DAT and SERT, where the Ki or $IC_{50}$ ratios for any of NET/SERT, NET/DAT, DAT/NET, DAT/SERT, SERT/NET, and SERT/DAT fall within the bounds defined for the "Mono-, Dual or Triple action transporter reuptake inhibitors" defined above.

Finally, selected compounds of the present invention have less potent binding affinity (Ki or $IC_{50}$ values between 100 nM and 1000 nM) for one, two, or three of the biogenic amine transporters, NET, DAT, and SERT, where the Ki or $IC_{50}$ ratios for any of NET/SERT, NET/DAT, DAT/NET, DAT/SERT, SERT, SERT/NET, and SERT/DAT fall outside of the bounds defined for the "mono-, dual or triple action transporter reuptake inhibitors" defined above.

EXAMPLES

The following examples are provided to illustrate embodiments of the present invention but are by no means intended to limit its scope.

Example 1

Preparation of (+)-2-methyl-5-(naphthalen-2-yloxy)-8-(pyridazin-3-yl)-2,3,4,5-tetrahydro-1H-benzo[c] azepine, tartrate salt Step A: To a solution of 3-bromobenzaldehyde (75.5 g, 408 mmol) in methanol (500 mL) at 0° C. was added methylamine (40% in aqueous, 38 g, 490 mmol), and iodine (1 g, 3.9 mmol). The mixture was stirred at 0° C. for 30 minutes. Sodium borohydride (23.2 g, 614 mmol) was added in portions. The mixture was stirred at 0° C. for 5 hours. The solvent was removed, and the residue was taken up with water and dichloromethane. The organic layer was separated, washed with brine, dried over sodium sulfate and concentrated to give the benzylamine (80 g, crude) as a light yellow oil: $^1$H NMR ($CDCl_3$, 500 MHz) δ 7.48 (s, 1H), 7.38 (d, J=8.0 Hz, 1H), 7.24 (d, J=8.0 Hz, 1H), 7.19 (t, J=8.0 Hz, 1H), 3.72 (s, 1H), 2.46 (s, 3H); ESI MS m/z 200 [M+H]$^+$.

Step B: A solution of the benzylamine (26.4 g, 131 mmol) from Step A above, acrylic acid (9.5 g, 131 mmol) and pyridine (150 mL) was refluxed for 2 hours. The solvent was removed, and the residue was dried under vacuum to give the acid (37.6 g, crude) as a light yellow oil: $^1$H NMR ($CDCl_3$, 300 MHz) δ 7.75-7.68 (m, 2H), 7.48-7.43 (m, 2H), 3.67 (s, 2H), 2.84 (t, J=6.0 Hz, 2H), 2.56 (t, J=6.0 Hz, 2H), 2.34 (s, 3H); ESI MS m/z 272 [M+H]$^+$ Step C: A mixture of the acid (80 g, crude) from Step B above and triflic acid (350 g, 2333 mmol) was heated at 120° C. for 72 hours. After cooling to room temperature, the mixture was slowly diluted with water (1000 mL) at 0° C. The aqueous mixture was adjusted with NaOH to pH=9. The product was extracted with dichloromethane, washed with brine, dried over sodium sulfate and concentrated to give the ketone (38 g, crude): $^1$H NMR ($CDCl_3$, 500 MHz) δ 7.52-7.51 (m, 1H), 7.38-7.37 (m, 1H), 7.31-7.28 (m, 1H), 3.89 (s, 2H), 2.84 (m, 4H), 2.43 (s, 9H); ESI MS m/z 254 [M+H]$^+$.

Step D: To a solution of the ketone (1.9 g, 7.3 mmol) in methanol (20 mL) was added $NaBH_4$ (418 mg, 11.0 mmol) in portions at 0° C. The mixture was stirred at 0° C. for 1 hour. The solvent was removed, and the residue was taken up with dichloromethane/water. The organic layer was separated, washed with brine, dried over sodium sulfate, and concentrated to give the alcohol (2.1 g, crude) as a dark oil: $^1$H NMR ($CDCl_3$, 300 MHz) δ 7.60-7.42 (m, 1H), 7.37-7.33 (m, 1H), 7.26-7.23 (m, 1H), 4.86-4.82 (m, 1H), 3.90-3.84 (m, 1H), 3.72-3.67 (m, 1H), 3.22-3.18 (m, 1H), 2.90-2.82 (m, 1H), 2.34 (s, 3H), 2.14-2.07 (m, 1H), 1.95-1.91 (m, 1H); ESI MS m/z 256 [M+H]$^+$.

Step E: A mixture of the alcohol from Step D above (15.2 g, crude), t-butyldimethylsilyl chloride (10 g, 66 mmol), imidazole (11.1 g, 166 mmol) and DMF (100 mL) was stirred at room temperature overnight. The mixture was diluted with water, washed with saturated aqueous $NaHCO_3$ solution, brine, dried over sodium sulfate, and concentrated. The residue was purified with chromatography (98:1.8:0.2 to 95:4.5: 0.5 dichloromethane/methanol/concentrated ammonium hydroxide) to give the TBS ether (12 g, 59%) as a brown oil: $^1$H NMR ($CDCl_3$, 300 MHz) δ 8.01 (s, 1H), 7.33 (d, J=7.9 Hz, 1H), 7.24 (d, J=7.9 Hz, 1H), 4.82 (t, J=4.9 Hz, 1H), 3.64-3.61

(m, 1H), 3.27-3.18 (m 1H), 2.36 (s, 3H), 1.95-1.85 (m, 2H), 1.80-1.63 (m, 2H), 0.91 (s, 9H), 0.097-0.085 (m, 6H); ESI MS m/z 370 [M+H]$^+$.

Step F: To a solution of the bromide (12 g, crude) from Step E in DMSO (120 mL) was added bis(pinacolato)diboron (8.7 g, 34.1 mmol) and potassium acetate (9.5 g, 97 mmol). The mixture was purged with argon. 1,1'-Bis(diphenylphosphino)ferrocenedichloropalladium (1.9 mg, 2.5 mmol) was added to the mixture. The reaction was heated at 85° C. for 1.5 hours. After cooling to room temperature, the reaction mixture was diluted with dichloromethane, and filtered through a pad of Celite. The filtrate was washed with water, brine, dried over sodium sulfate and concentrated to give the desired boronate ester (19 g, crude) as a thick black liquid: ESI MS m/z 418 [M+H]$^+$.

Step G: The boronate ester (19 g, crude) from Step F above, 3-chloro-pyridazine (4.8 g, 42 mmol), and cesium carbonate (21 g, 63 mmol) were suspended in DMF (120 mL) and water (30 mL). The mixture was purged with argon. 1,1'-Bis(diphenylphosphino)ferrocenedichloropalladium (240 mg, 0.33 mmol) was added to the mixture. The mixture was heated at 100° C. for 2 hours. After cooling to room temperature, the reaction mixture was diluted with dichloromethane, and filtered through a pad of Celite. The filtrate was washed with water, brine, dried over sodium sulfate and concentrated. The residue was purified by flash chromatography (98:1.8:0.2 to 95:4.5:0.5 dichloromethane/methanol/concentrated ammonium hydroxide) to give 5-(tert-butyldimethylsilyloxy)-2-methyl-8-(pyridazin-3-yl)-2,3,4,5-tetrahydro-1H-benzo[c]azepine (4.7 g, 40% for 2 steps) as an oil. This oil was resolved using Chiralcel OD column (eluente:80 Hep:20 IPA:0.1 DEA) to give (+)-enantiomer (2.3 g, 98%, ([α]$^{25}_D$, +26.9° (C, 0.29 Methanol) and (−)-enantiomer (2.3 g, 98%, [α]$^{25}_D$, −23.2° (C, 0.28 Methanol)): $^1$H NMR (CDCl$_3$, 300 MHz) δ 9.15 (d, J=4.8 Hz, 1H), 7.91-7.84 (m, 3H), 7.54-7.50 (m, 2H), 4.96 (t, J=5.2 Hz, 1H), 4.26-4.05 (m, 1H), 3.85-3.73 (m, 1H), 3.30-3.21 (m, 1H), 2.97-2.91 (m, 1H), 2.32 (s, 3H) 1.95-1.85 (m, 2H), 0.91 (s, 9H), 0.097-0.085 (m, 6H); ESI MS m/z 370 [M+H]$^+$.

Step H: To the solution of the (−)-5-(tert-butyldimethylsilyloxy)-2-methyl-8-(pyridazin-3-yl)-2,3,4,5-tetrahydro-1H-benzo[c]azepine (2.14 g, 5.8 mmol) from Step G above in THF was added TBAF (1.0 M in THF, 10 mL, 10 mmol). The reaction mixture was stirred at room temperature for 3 hours. The solvent was removed. The residue was purified by flash chromatography (97:2.7:0.3 to 93:6.3:0.7 ethyl acetate/methanol/concentrated ammonium hydroxide) to give (−)-2-methyl-8-(pyridazin-3-yl)-2,3,4,5-tetrahydro-1H-benzo[c]azepin-5-ol (1.34 g, 90%) as a white solid ([α]$^{25}_D$, −28.6°, (C, 0.18 Methanol)): ESI MS m/z 256 [M+H]$^+$.

Step I: To a solution of (−)-2-methyl-8-(pyridazin-3-yl)-2,3,4,5-tetrahydro-1H-benzo[c]azepin-5-ol (17.8 mg, 0.070 mmol) from Step H above in methanol (1 mL) was added L-tartaric acid (11 mg, 0.073 mmol) followed by slow addition of water (5 mL). The resultant solution was lyophilized overnight to give (−)-2-methyl-8-(pyridazin-3-yl)-2,3,4,5-tetrahydro-1H-benzo[c]azepin-5-ol, tartrate salt (28 mg, 97%, AUC HPLC>99%) as a off-white solid: mp 102-104° C.; $^1$H NMR (CD$_3$OD, 500 MHz) δ 9.18 (d, J=5.0 Hz, 1H), 8.21 (d, J=8.7 Hz, 1H), 8.16 (s, 1H), 8.13 (d, J=7.9 Hz, 1H), 7.82 (dd, J=8.7, 4.9 Hz, 1H), 7.69-7.65 (m, 1H), 5.09-5.07 (m, 1H), 4.88-4.81 (m, 1H), 4.45-4.41 (m, 1H), 3.50-3.44 (m, 1H), 2.90 (s, 3H), 2.24-2.22 (m, 1H); ESI MS m/z 256 [M+H].

Step J: To a solution of (−)-2-methyl-8-(pyridazin-3-yl)-2,3,4,5-tetrahydro-1H-benzo[c]azepin-5-ol (80 mg, 0.31) from Step H above in THF (5 mL) was added napthalen-2-ol (67 mg, 0.47 mmol), tributylphosphine (95 mg, 0.47 mmol) and 1,1'-(azodicarboyl)dipiperidine (118 mg, 0.47 mmol) at room temperature. The reaction mixture was stirred at room temperature for 3 hours. The mixture was diluted with dichloromethane and washed with water, brine, dried over sodium sulfate and concentrated. The residue was purified by chromatography (98:2 to 95:5 ethyl acetate/methanol), followed by HPLC to give the (+)-5-(naphthalen-2-yloxy)-8-(pyridazin-3-yl)-2,3,4,5-tetrahydro-1H-benzo[c]azepine (60 mg, 48%) as a gum-like solid.

Step K: To a solution of the product (45 mg, 0.12 mmol) from Step J above in methanol (1 mL) was added L-tartaric acid (17 mg, 0.12 mmol) followed by slow addition of water (5 mL). The resultant solution was lyophilized overnight to give (+)-5-(naphthalen-2-yloxy)-8-(pyridazin-3-yl)-2,3,4,5-tetrahydro-1H-benzo[c]azepine, tartrate salt (58 mg, 94%, AUC HPLC>99%) as white solid: mp 122-124° C.; $^1$H NMR (CD$_3$OD, 500 MHz) δ 9.18 (d, J=5.0 Hz, 1H), 8.21 (s, 1H), 8.19 (d, J=8.7 Hz, 1H), 8.09 (d, J=8.0 Hz, 1H), 7.81-7.76 (m, 4H), 7.70 (d, J=8.2 Hz, 1H), 7.40 (t, J=8.2 Hz, 1H), 7.37 (s, 1H), 7.34-7.31 (m, 2H), 5.94 (d, J=8.2 Hz, 1H), 4.88-4.81 (m, 1H), 4.60-4.56 (m, 1H), 4.40 (s, 2H), 3.98-3.90 (m, 1H), 3.70-3.60 (m, 1H), 2.92 (s, 3H), 2.54-2.48 (m, 2H); ESI MS m/z 382 [M+H].

Example 2

Preparation of (+)-5-(4-chlorophenoxy)-2-methyl-8-(pyridazin-3-yl)-2,3,4,5-tetrahydro-1H-benzo[c]azepine, tartrate salt This compound was prepared from (−)-2-methyl-8-(pyridazin-3-yl)-2,3,4,5-tetrahydro-1H-benzo[c]azepin-5-ol from Step H in Example 1 and 4-chlorophenol, following the procedures of Steps J and K in Example 1. (+)-5-(4-Chlorophenyl)-8-(pyridazin-3-yl)-2,3,4,5-tetrahydro-1H-benzo[c]azepine, tartrate salt (AUC HPLC>99%) is a white solid: mp 106-108° C.; $^1$H NMR (CD$_3$OD, 500 MHz) δ 9.18 (d, J=5.0 Hz, 1H), 8.20-8.17 (m, 2H), 8.07 (d, J=8.0 Hz, 1H), 7.80 (dd, J=8.7, 3.8 Hz, 1H), 7.66 (d, J=7.9 Hz, 1H), 7.25 (d, J=9.0 Hz, 2H), 7.05 (d, J=9.0 Hz, 2H), 5.73 (d, J=7.6 Hz, 1H), 4.92-4.84 (m, 1H), 4.52-4.46 (m, 1H), 4.42 (s, 3H), 3.90-3.80 (m, 1H), 3.56-3.50 (m, 1H), 2.86 (s, 3H), 2.46-2.37 (m, 2H); ESI MS m/z 366 [M+H].

Example 3

Preparation of (+)-2-methyl-8-(pyridazin-3-yl)-5-(p-tolyloxy)-2,3,4,5-tetrahydro-1H-benzo[c]azepine, tartrate salt This compound was prepared from (−)-2-methyl-8-(pyridazin-3-yl)-2,3,4,5-tetrahydro-1H-benzo[c]azepin-5-ol from Step H in Example 1 and p-cresol, following the procedures of Steps J and K in Example 1. (+)-2-Methyl-8-(pyridazin-3-yl)-5-(p-tolyloxy)-2,3,4,5-tetrahydro-1H-benzo[c]azepine, tartrate salt (AUC HPLC>99%) is a white solid: mp 104-106° C.; $^1$H NMR (CD$_3$OD, 500 MHz) δ 9.18 (d, J=5.0 Hz, 1H), 8.20-8.18 (m, 2H), 8.08 (d, J=8.6 Hz, 1H), 7.80 (dd, J=8.7, 3.8 Hz, 1H), 7.66 (d, J=7.9 Hz, 1H), 7.06 (d, J=9.0 Hz, 2H), 6.93 (d, J=9.0 Hz, 2H), 5.69 (d, J=7.7 Hz, 1H), 4.96-4.88 (m, 1H), 4.55-4.52 (m, 1H), 4.43 (s, 3H), 3.98-3.93 (m, 1H), 3.60-3.58 (m, 1H), 2.93 (s, 3H), 2.54-2.35 (m, 2H); ESI MS m/z 346 [M+H].

Example 4

Preparation of (+)-2-methyl-8-(pyridazin-3-yl)-5-(4-(trifluoromethoxy)phenoxy)-2,3,4,5-tetrahydro-1H-benzo[c]azepine, tartrate salt This compound was prepared from (−)-2-methyl-8-(pyridazin-3-yl)-2,3,4,5-tetrahydro-1H-benzo[c]azepin-5-ol from Step H in Example 1 and 4-(trifluoromethoxy)phenol, following the procedures of Steps J and K in Example 1. (+)-2-Methyl-8-(pyridazin-3-yl)-5-(4-(trifluoromethoxy)phenoxy)-2,3,4,5-tetrahydro-1H-benzo[c]azepine, tartrate salt (AUC HPLC 98.4%) is a white solid: mp 104-106° C.; $^1$H NMR (CD$_3$OD, 500 MHz) δ 9.18 (d, J=5.0 Hz, 1H), 8.20-8.18 (m, 2H), 8.08 (d, J=8.0 Hz, 1H), 7.81 (dd, J=8.7, 3.8 Hz, 1H), 7.68 (d, J=8.0 Hz, 1H), 7.19 (d, J=9.0 Hz, 2H), 7.14 (d, J=9.0 Hz, 2H), 5.76 (d, J=8.0 Hz, 1H), 4.92-4.84 (m, 1H), 4.50-4.47 (m, 1H), 4.42 (s, 3H), 3.90-3.80 (m, 1H), 3.58-3.52 (m, 1H), 2.87 (s, 3H), 2.54-2.38 (m, 2H); ESI MS m/z 416 [M+H].

Example 5

Preparation of (+)-5-(3,5-difluorophenoxy)-2-methyl-8-(pyridazin-3-yl)-2,3,4,5-tetrahydro-1H-benzo[c]azepine, tartrate salt This compound was prepared from (−)-2-methyl-8-(pyridazin-3-yl)-2,3,4,5-tetrahydro-1H-benzo[c]azepin-5-ol from Step H in Example 1 and 3,5-difluorophenol, following the procedures of Steps J and K in Example 1. (+)-5-(3,5-Difluorophenoxy)-2-methyl-8-(pyridazin-3-yl)-2,3,4,5-tetrahydro-1H-benzo[c]azepine, tartrate salt (AUC HPLC>99%) is a white solid: mp 94-96° C.; $^1$H NMR (CD$_3$OD, 500 MHz) δ 9.18 (d, J=4.5 Hz, 1H), 8.22-8.20 (m, 2H), 8.12 (d, J=8.0 Hz, 1H), 7.81 (dd, J=8.7, 3.8 Hz, 1H), 7.70 (d, J=8.0 Hz, 1H), 6.78-6.75 (m, 2H), 6.58-6.53 (m, 1H), 5.82 (d, J=7.9 Hz, 1H), 4.88-4.81 (m, 1H), 4.58-4.53 (m, 1H), 4.43 (s, 3H), 3.92-3.82 (m, 1H), 3.65-3.58 (m, 1H), 2.90 (s, 3H), 2.58-2.40 (m, 2H); ESI MS m/z 368 [M+H].

Example 6

Preparation of (+)-4-(2-Methyl-8-(pyridazin-3-yl)-2,3,4,5-tetrahydro-1H-benzo[c]azepin-5-yloxy)benzonitrile, tartrate salt This compound was prepared from (−)-2-methyl-8-(pyridazin-3-yl)-2,3,4,5-tetrahydro-1H-benzo[c]azepin-5-ol from Step H in Example 1 and 4-hydroxybenzonitrile, following the procedures of Steps J and K in Example 1. (+)-4-(2-Methyl-8-(pyridazin-3-yl)-2,3,4,5-tetrahydro-1H-benzo[c]azepin-5-yloxy)benzonitrile, tartrate salt (AUC HPLC>99%) is a white solid: mp 94-96° C.; $^1$H NMR (CD$_3$OD, 500 MHz) δ 9.18 (d, J=4.9 Hz, 1H), 8.21-8.19 (m, 2H), 8.11 (d, J=8.0 Hz, 1H), 7.70-7.65 (m, 3H), 7.24 (d, J=8.8 Hz, 2H), 5.92 (d, J=7.7 Hz, 1H), 4.88-4.81 (m, 1H), 4.56-4.52 (m, 1H), 4.43 (s, 3H), 3.90-3.80 (m, 1H), 3.65-3.58 (m, 1H), 2.88 (s, 3H), 2.66-2.40 (m, 2H); ESI MS m/z 357 [M+H].

Example 7

Preparation of (+)-5-(3,4-Dichlorophenoxy)-2-methyl-8-(pyridazin-3-yl)-2,3,4,5-tetrahydro-1H-benzo[c]azepine, tartrate salt This compound was prepared from (−)-2-methyl-8-(pyridazin-3-yl)-2,3,4,5-tetrahydro-1H-benzo[c]azepin-5-ol from Step H in Example 1 and 3,4-dichlorophenol, following the procedures of Steps J and K in Example 1. (+)-5-(3,4-Dichlorophenoxy)-2-methyl-8-(pyridazin-3-yl)-2,3,4,5-tetrahydro-1H-benzo[c]azepine, tartrate salt (AUC HPLC 98.8%) is a white solid: mp 102-104° C.; $^1$H NMR (CD$_3$OD, 500 MHz) δ 9.18 (d, J=4.9 Hz, 1H), 8.21-8.19 (m, 2H), 8.11 (d, J=8.0 Hz, 1H), 7.82-7.80 (m, 1H), 7.67 (d, J=7.9 Hz, 1H), 7.40 (d, J=9.0 Hz, 1H), 7.29 (d, J=2.9 Hz, 1H), 7.05 (d, J=8.9 Hz, 1H), 5.79 (d, J=7.8 Hz, 1H), 4.88-4.80 (m, 1H), 4.53-4.45 (m, 1H), 4.42 (s, 3H), 3.90-3.80 (m, 1H), 3.60-3.52 (m, 1H), 2.88 (s, 3H), 2.56-2.38 (m, 2H); ESI MS m/z 400 [M+H].

Example 8

Preparation of (+)-5-(3,4-Difluorophenoxy)-2-methyl-8-(pyridazin-3-yl)-2,3,4,5-tetrahydro-1H-benzo[c]azepine, tartrate salt This compound was prepared from (−)-2-methyl-8-(pyridazin-3-yl)-2,3,4,5-tetrahydro-1H-benzo[c]azepin-5-ol from Step H in Example 1 and 3,4-difluorophenol, following the procedures of Steps J and K in Example 1. (+)-5-(3,4-Difluorophenoxy)-2-methyl-8-(pyridazin-3-yl)-2,3,4,5-tetrahydro-1H-benzo[c]azepine, tartrate salt (AUC HPLC>99%) is a white solid: mp 100-102° C.; $^1$H NMR (CD$_3$OD, 500 MHz) δ 9.18 (d, J=4.7 Hz, 1H), 8.21-8.19 (m, 2H), 8.11 (d, J=7.9 Hz, 1H), 7.83-7.80 (m, 1H), 7.67 (d, J=8.0 Hz, 1H), 7.19-7.13 (m, 1H), 7.09-7.05 (m, 1H), 6.89-6.87 (m, 1H), 5.73 (d, J=7.3 Hz, 1H), 4.89-4.81 (m, 1H), 4.60-4.50 (m, 1H), 4.44 (s, 3H), 3.96-3.88 (m, 1H), 3.64-3.55 (m, 1H), 2.92 (s, 3H), 2.56-2.38 (m, 2H); ESI MS m/z 368 [M+H].

Example 9

Preparation of (+)-5-(2,4-Difluorophenoxy)-2-methyl-8-(pyridazin-3-yl)-2,3,4,5-tetrahydro-1H-benzo[c]azepine, tartrate salt This compound was prepared from (−)-2-methyl-8-(pyridazin-3-yl)-2,3,4,5-tetrahydro-1H-benzo[c]azepin-5-ol from Step H in Example 1 and 2,4-difluorophenol following the procedures of Steps J and K in Example 1. (+)-5-(2,4-Difluorophenoxy)-2-methyl-8-(pyridazin-3-yl)-2,3,4,5-tetrahydro-1H-benzo[c]azepine, tartrate salt (AUC HPLC>99%) is a white solid: mp 98-100° C.; $^1$H NMR (CD$_3$OD, 500 MHz) δ 9.18 (d, J=4.9 Hz, 1H), 8.21-8.19 (m, 2H), 8.05 (d, J=7.9 Hz, 1H), 7.83-7.80 (m, 1H), 7.56 (d, J=7.9 Hz, 1H), 7.22-7.17 (m, 1H), 7.00-6.95 (m, 1H), 6.86-6.83 (m, 1H), 5.62 (d, J=7.0 Hz, 1H), 4.96-4.92 (m, 1H), 4.44-4.41 (m, 3H), 4.44 (s, 3H), 3.95-3.86 (m, 1H), 3.53-3.50 (m, 1H), 2.86 (s, 3H), 2.56-2.52 (m, 1H), 2.45-2.40 (m, 1H); ESI MS m/z 368 [M+H].

Example 10

Preparation of (−)-2-methyl-5-phenoxy-8-(pyridazin-3-yl)-2,3,4,5-tetrahydro-1H-benzo[c]azepine, tartrate salt Step A: To the solution of the (+)-5-(tert-butyldimethylsilyloxy)-2-methyl-8-(pyridazin-3-yl)-2,3,4,5-tetrahydro-1H-benzo[c]azepine (2.2 g, 5.8 mmol) from Step G in Example 1, THF (30 mL) was added TBAF (1.0 M in THF, 10 mL, 10 mmol). The reaction mixture was stirred at room temperature for 3 hours. The solvent was removed. The residue was purified by flash chromatography (97:2.7:0.3 to 93:6.3:0.7 ethyl acetate/methanol/concentrated ammonium hydroxide) to give 2-methyl-8-(pyridazin-3-yl)-2,3,4,5-tetrahydro-1H-benzo[c]azepin-5-ol (1.01 g, 66%) as a white solid [[α]$^{25}_D$, +37.1°, (C, 0.21 Methanol)]: ESI MS m/z 256 [M+H]$^+$.

Step B: To a solution of (+)-2-methyl-8-(pyridazin-3-yl)-2,3,4,5-tetrahydro-1H-benzo[c]azepin-5-ol (65 mg, 0.25) from Step A in THF (5 mL) was added phenol (73 mg, 0.77 mmol), tributylphosophine (156 mg, 0.77 mmol) and 1,1'-(azodicarboyl)dipiperidine (192 mg, 0.77 mmol) at room temperature. The reaction mixture was stirred at room temperature for 3 hours. The mixture was diluted with dichloromethane and washed with water, brine, dried over sodium sulfate and concentrated. The residue was purified by chromatography (98:2 to 95:5 ethyl acetate/methanol), followed by HPLC to give (–)-2-methyl-5-phenoxy-8-(pyridazin-3-yl)-2,3,4,5-tetrahydro-1H-benzo[c]azepine (52 mg, 62%) as a gum-like solid.

Step C: To a solution of the aryloxybenzazepine (52 mg, 0.16 mmol) from Step B above in methanol (1 mL) was added L-tartaric acid (23.5 mg, 0.16 mmol) followed by slow addition of water (5 mL). The resultant solution was lyophilized overnight to give (–)-2-methyl-5-phenoxy-8-(pyridazin-3-yl)-2,3,4,5-tetrahydro-1H-benzo[c]azepine, tartrate salt (70 mg, 93%, AUC HPLC>99%) as a white solid: mp 98-100° C.; $^1$H NMR (CD$_3$OD, 500 MHz) δ 9.17 (d, J=5.0 Hz, 1H), 8.21-8.18 (m, 2H), 8.08 (d, J=8.0 Hz, 1H), 7.82-7.79 (m, 1H), 7.68 (d, J=8.0 Hz, 1H), 7.28-7.25 (m, 2H), 7.06 (d, J=7.9 Hz, 2H), 6.95 (t, J=7.4 Hz, 1H), 5.75 (d, J=8.0 Hz, 1H), 4.92-4.84 (m, 1H), 4.51-4.48 (m, 1H), 4.41 (s, 2H), 3.95-3.85 (m, 1H), 3.57-3.55 (m, 1H), 2.88 (s, 3H), 2.46-2.38 (m, 2H); ESI MS m/z 332 [M+H].

Example 11

Preparation of (–)-2-methyl-8-(pyridazin-3-yl)-5-(pyridin-3-yloxy)-2,3,4,5-tetrahydro-1H-benzo[c]azepine, tartrate salt This compound was prepared from (+)-2-methyl-8-(pyridazin-3-yl)-2,3,4,5-tetrahydro-1H-benzo[c]azepin-5-ol from Step A in Example 10 and 3-hydroxypyridine, following the procedures of Steps B and C in Example 10. The salt (AUC HPLC>99%) is a white solid: mp 120-123° C.; $^1$H NMR (CD$_3$OD, 500 MHz) δ 9.18 (d, J=4.9 Hz, 1H), 8.36-8.38 (m, 1H), 8.21-8.19 (m, 2H), 8.16 (d, J=4.7 Hz, 1H), 8.11 (d, J=7.9 Hz, 1H), 7.83-7.80 (m, 1H), 7.70 (d, J=8.0 Hz, 1H), 7.59 (d, J=4.0 Hz, 1H), 7.38-7.35 (m, 1H), 5.87 (d, J=7.7 Hz, 1H), 4.92-4.84 (m, 1H), 4.52-4.46 (m, 1H), 4.42 (s, 4H), 3.95-3.85 (m, 1H), 3.60-3.59 (m, 1H), 2.90 (s, 3H), 2.55-2.42 (m, 2H); ESI MS m/z 333 [M+H].

Example 12

Preparation of (–)-5-(2-fluorophenoxy)-2-methyl-8-(pyridazin-3-yl)-2,3,4,5-tetrahydro-1H-benzo[c]azepine, tartrate salt This compound was prepared from (+)-2-methyl-8-(pyridazin-3-yl)-2,3,4,5-tetrahydro-1H-benzo[c]azepin-5-ol from Step A in Example 10 and 2-fluorophenol, following the procedures of Steps B and C in Example 10. (–)-5-(2-Fluorophenoxy)-2-methyl-8-(pyridazin-3-yl)-2,3,4,5-tetrahydro-1H-benzo[c]azepine, tartrate salt (AUC HPLC>98.4%) is a white solid: mp 96-98° C.; $^1$H NMR (CD$_3$OD, 500 MHz) 9.17 (d, J=6.3 Hz, 1H), 8.20-8.19 (m, 2H), 8.06 (d, J=7.9 Hz, 1H), 7.82-7.80 (m, 1H), 7.61 (d, J=7.9 Hz, 1H), 7.20 (d, J=7.3 Hz, 1H), 7.12-7.04 (m, 2H), 6.98-6.96 (m, 1H), 5.71 (d, J=7.3 Hz, 1H), 5.00-4.94 (m, 1H), 4.48-4.45 (m, 1H), 4.42 (s, 2H), 3.98-3.93 (m, 1H), 3.60-3.54 (m, 1H), 2.89 (s, 3H), 2.55-2.44 (m, 2H); ESI MS m/z 350 [M+H].

Example 13

Preparation of (–)-5-(3-fluorophenoxy)-2-methyl-8-(pyridazin-3-yl)-2,3,4,5-tetrahydro-1H-benzo[c]azepine, tartrate salt This compound was prepared from (+)-2-methyl-8-(pyridazin-3-yl)-2,3,4,5-tetrahydro-1H-benzo[c]azepin-5-ol from Step A in Example 10 and 3-fluorophenol, following the procedures of Steps B and C in Example 10. (–)-5-(3-Fluorophenoxy)-2-methyl-8-(pyridazin-3-yl)-2,3,4,5-tetrahydro-1H-benzo[c]azepine, tartrate salt (AUC HPLC 97.4%) is a white solid: mp 96-98° C.; $^1$H NMR (CD$_3$OD, 500 MHz) δ 9.18-9.17 (m, 1H), 8.21-8.18 (m, 2H), 8.11-8.09 (m, 1H), 7.83-7.80 (m, 1H), 7.70-7.68 (m, 1H), 7.28-7.26 (m, 1H), 6.91-6.83 (m, 2H), 6.70 (t, J=7.9 Hz, 1H), 5.79 (d, J=7.5 Hz, 1H), 4.86-4.84 (m, 1H), 4.52-4.48 (m, 1H), 4.42 (s, 2H), 3.92-3.83 (m, 1H), 3.62-3.52 (m, 1H), 2.85 (s, 3H), 2.47-2.42 (m, 2H); ESI MS m/z 350 [M+H].

Example 14

Preparation of (–)-5-(3,5-difluorophenoxy)-2-methyl-8-(pyridazin-3-yl)-2,3,4,5-tetrahydro-1H-benzo[c]azepine, tartrate salt This compound was prepared from (+)-2-methyl-8-(pyridazin-3-yl)-2,3,4,5-tetrahydro-1H-benzo[c]azepin-5-ol from Step A in Example 10 and 3,5-difluorophenol, following the procedures of Steps B and C in Example 10. (–)-5-(3,5-Difluorophenoxy)-2-methyl-8-(pyridazin-3-yl)-2,3,4,5-tetrahydro-1H-benzo[c]azepine, tartrate salt (AUC HPLC 98.3%) is a white solid: mp 120-122° C.; $^1$H NMR (CD$_3$OD, 500 MHz) δ 9.17 (d, J=4.9 Hz, 1H), 8.75-8.74 (m, 1H), 8.29 (d, J=7.7 Hz, 1H), 8.21 (s, 1H), 8.19 (d, J=8.7 Hz, 1H), 8.11 (d, J=8.0 Hz, 1H), 7.91 (d, J=9.0 Hz, 1H), 7.81-7.77 (m, 2H), 7.50-7.48 (m, 2H), 7.42-7.39 (m, 1H), 6.02 (d, J=7.8 Hz, 1H), 4.88-4.80 (m, 1H), 4.65-4.55 (m, 1H), 4.42 (s, 2H), 3.95-3.85 (m, 1H), 3.67-3.60 (m, 1H), 2.90 (s, 3H), 2.62-2.48 (m, 2H); ESI MS m/z 368 [M+H].

Example 15

Preparation of (–)-2-Methyl-5-(naphthalen-1-yloxy)-8-(pyridazin-3-yl)-2,3,4,5-tetrahydro-1H-benzo[c]azepine, tartrate salt This compound was prepared from (+)-2-methyl-8-(pyridazin-3-yl)-2,3,4,5-tetrahydro-1H-benzo[c]azepin-5-ol from Step A in Example 10 and 4-hydroxybenzonitrile, following the procedures of Steps B and C in Example 10. (+)-2-Methyl-5-(naphthalen-1-yloxy)-8-(pyridazin-3-yl)-2,3,4,5-tetrahydro-1H-benzo[c]azepine, tartrate salt (AUC HPLC>99%) is a white solid: mp 100-102° C.; $^1$H NMR (CD$_3$OD, 500 MHz) δ 9.17 (d, J=4.9 Hz, 1H), 8.39 (d, J=7.8 Hz, 1H), 8.22-8.19 (m, 2H), 8.10 (d, J=8.0 Hz, 1H), 7.82-7.80 (m, 2H), 7.47 (d, J=8.1 Hz, 1H), 7.32 (t, J=8.0 Hz, 1H), 6.99 (d, J=7.8 Hz, 1H) 5.99 (d, J=8.4 Hz, 1H), 4.92-4.84 (m, 1H), 4.61-4.58 (m, 1H), 4.42 (s, 2H), 3.95-3.85 (m, 1H), 3.70-3.63 (m, 1H), 2.90 (s, 3H), 2.68-2.52 (m, 2H); ESI MS m/z 382 [M+H].

Example 16

Preparation of (+)- and (−)-2-methyl-8-(6-methylpyridazin-3-yl)-5-phenoxy-2,3,4,5-tetrahydro-1H-benzo[c]azepine, tartrate salt Step A: To a solution of 3-bromobenzaldehyde (75.5 g, 408 mmol) in methanol (500 mL) at 0° C. was added methylamine (40% in aqueous, 38 g, 490 mmol), and iodine (1 g, 3.9 mmol). The mixture was stirred at 0° C. for 30 minutes. Sodium borohydride (23.2 g, 614 mmol) was added in portions. The mixture was stirred at 0° C. for 5 hours. The solvent was removed, and the residue was taken up with water and dichloromethane. The organic layer was separated, washed with brine, dried over sodium sulfate, and concentrated to give the benzylamine (80 g, crude) as a light yellow oil: $^1$H NMR (CDCl$_3$, 500 MHz) δ 7.48 (s, 1H), 7.38 (d, J=8.0 Hz, 1H), 7.24 (d, J=8.0 Hz, 1H), 7.19 (t, J=8.0 Hz, 1H), 3.72 (s, 1H), 2.46 (s, 3H); ESI MS m/z 200 [M+H]$^+$.

Step B: A solution of the benzylamine (26.4 g, 131 mmol) from Step A above, acrylic acid (9.5 g, 131 mmol) and pyridine (150 mL) was refluxed for 2 hours. The solvent was removed, and the residue was dried under vacuum to give the desired acid (37.6 g, crude) as a light yellow oil: $^1$H NMR (CDCl$_3$, 300 MHz) δ 7.68-7.75 (m, 2H), 7.48-7.43 (m, 2H), 3.67 (s, 2H), 2.84 (t, J=6.0 Hz, 2H), 2.56 (t, J=6.0 Hz, 2H), 2.34 (s, 3H); ESI MS m/z 272 [M+H]$^+$ Step C: A mixture of the acid (80 g, crude) from Step B above and triflic acid (350 g, 2333 mmol) was heated at 120° C. for 72 hours. After cooling to room temperature, the mixture was slowly diluted with water (1000 mL) with ice-bath cooling. The aqueous mixture was adjusted with NaOH to pH=9. The product was extracted with dichloromethane, washed with brine, dried and concentrated to give the desired lactone (38 g, crude) as a dark oil: $^1$H NMR (CDCl$_3$, 500 MHz) δ 7.52-7.51 (m, 1H), 7.38-7.37 (m, 1H), 7.31-7.28 (m, 1H), 3.89 (s, 2H), 2.84 (m, 4H), 2.43 (s, 9H); ESI MS m/z 254 [M+H]$^+$.

Step D: To a solution of the lactone from Step C above (1.9 g, 7.3 mmol) in methanol (20 mL) was added NaBH$_4$ (418 mg, 11.0 mmol) in portions at 0° C. The mixture was stirred at 0° C. for 1 hour. The solvent was removed, and the residue was taken up with dichloromethane/water. The organic layer was separated, washed with brine, dried and concentrated to give the desired alcohol (2.1 g, crude) as a dark oil: $^1$H NMR (CDCl$_3$, 300 MHz) δ 7.60-7.42 (m, 1H), 7.37-7.33 (m, 1H), 7.26-7.23 (m, 1H), 4.86-4.82 (m, 1H), 3.90-3.84 (m, 1H), 3.72-3.67 (m, 1H), 3.22-3.18 (m, 1H), 2.90-2.82 (m, 1H), 2.34 (s, 3H), 2.14-2.07 (m, 1H), 1.95-1.91 (m, 1H); ESI MS m/z 256 [M+H]$^+$.

Step E: To a solution of the alcohol (2.1 g, crude) from Step D above in THF (50 mL) was added phenol (928 mg, 9.8 mmol), tributylphosphine (2.0 g, 9.8 mmol) and 1,1'-(azodicarboyl)dipiperidine (2.48 g, 9.8 mmol) at room temperature. The reaction mixture was stirred at room temperature for 5 hours. The mixture was diluted with dichloromethane and washed with water, brine, dried and concentrated. The residue was purified by chromatography (98:2 to 95:5 ethyl acetate/methanol) to give the aryloxyether (3.8 g, crude) as a brown oil: $^1$H NMR (CDCl$_3$, 300 MHz) δ 7.34-7.22 (m, 5H), 6.96-6.87 (m, 3H), 5.34 (dd, J=8.2, 2.6 Hz, 1H), 4.00-3.75 (m, 1H), 3.49-3.31 (m 3H), 3.12-2.98 (m, 1H), 2.32 (s, 3H), 2.18-1.08 (m, 1H); ESI MS m/z 332 [M+H]$^+$.

Step F: To a solution of the bromide (3.8 g, crude) from Step E in DMSO (25 mL) was added bis(pinacolato)diboron (2.5 g, 9.8 mmol) and potassium acetate (2.41 g, 24.6 mmol). The mixture was purged with argon. 1,1'-Bis(diphenylphosphino)ferrocenedichloropalladium (600 mg, 0.82 mmol) was added to the mixture. The reaction was heated at 85° C. for 1.5 hours. After cooling to room temperature, the reaction mixture was diluted with dichloromethane, and filtered through a pad of Celite. The filterate was washed with water, brine, dried over sodium sulfate and concentrated to give the desired boronate ester (7.0 g, crude) as a thick black liquid: ESI MS m/z 380 [M+H]$^+$.

Step G: The boronate ester (3.5 g, crude) from Step F above, 3-chloro-6-methylpyridazine (625 mg, 5.1 mmol), and cesium carbonate (4.0 g, 6.8 mmol) were suspended in DMF (20 mL) and water (5 mL). The mixture was purged with argon. 1,1'-Bis(diphenylphosphino)ferrocenedichloropalladium (240 mg, 0.33 mmol) was added to the mixture. The mixture was heated at 100° C. for 2 hours. After cooling to room temperature, the reaction mixture was diluted with dichloromethane, and filtered through a pad of Celite. The filtrate was washed with water, brine, dried over sodium sulfate and concentrated. The residue was purified by flash chromatography (98:1.8:0.2 to 95:4.5:0.5 dichloromethane/methanol/concentrated ammonium hydroxide) to give 2-methyl-8-(6-methylpyridazin-3-yl)-5-phenoxy-2,3,4,5-tetrahydro-1H-benzo[c]azepine (500 mg, 40% for 3 steps) as an oil.

Step I: The free base of benzazepine from Step H above was resolved by preparative chiral HPLC(CHIRALPAK AD column, using 80:20:0.1 heptane/isopropanol/diethylamine as the eluente) to give enantiomer A [[α]$^{25}_D$, +30°, (C, 0.07 Methanol)] and enantiomer B [[α]$^{25}_D$, 62.8° (C, 0.07 Methanol)].

Step J: To a solution of the enantiomer A (160 mg, 0.46 mmol) from Step I above in methanol (2 mL) was added L-tartaric acid (70 mg, 0.47 mmol) followed by slow addition of water (10 mL). The resultant solution was lyophilized overnight to give (+)-2-methyl-8-(6-methylpyridazin-3-yl)-5-phenoxy-2,3,4,5-tetrahydro-1H-benzo[c]azepine, tartrate salt (200 mg, 87%, AUC HPLC 98.6%) as a off-white solid: mp 82-84° C.; $^1$H NMR (CD$_3$OD, 500 MHz) δ 8.16 (s, 1H), 8.07 (t, J=8.8 Hz, 2H), 7.69 (d, J=8.7 Hz, 1H), 7.67 (d, J=7.9 Hz, 1H), 7.26 (t, J=8.2 Hz, 2H), 7.06 (d, J=8.2 Hz, 2H), 6.95 (t, J=7.3 Hz, 1H) 5.75 (d, J=7.3 Hz, 1H), 4.63-4.53 (m, 1H), 4.00-3.90 (m, 1H), 3.68-3.58 (m, 1H), 2.93 (s, 3H), 2.72 (s, 3H), 2.55-2.38 (m, 2H); ESI MS m/z 346 [M+H].

Step K: To a solution of the enantiomer B (150 mg, 0.43 mmol) from Step I above in methanol (2 mL) was added L-tartaric acid (66 mg, 0.44 mmol) followed by slow addition of water (10 mL). The resultant solution was lyophilized overnight to give (−)-2-methyl-8-(6-methylpyridazin-3-yl)-5-phenoxy-2,3,4,5-tetrahydro-1H-benzo[c]azepine, tartrate salt (210 mg, 97%, AUC HPLC>99%) as a off-white solid: mp 80-82° C.; $^1$H NMR (CD$_3$OD, 500 MHz) δ 8.16 (s, 1H), 8.07 (t, J=8.8 Hz, 2H), 7.69 (d, J=8.7 Hz, 1H), 7.67 (d, J=7.9 Hz, 1H), 7.26 (t, J=8.2 Hz, 2H), 7.06 (d, J=8.2 Hz, 2H), 6.95 (t, J=7.3 Hz, 1H) 5.75 (d, J=7.3 Hz, 1H), 4.63-4.53 (m, 1H), 4.00-3.90 (m, 1H), 3.68-3.58 (m, 1H), 2.93 (s, 3H), 2.72 (s, 3H), 2.55-2.38 (m, 2H); ESI MS m/z 346 [M+H].

Example 17

Preparation of (+)- and (−)-5-(4-fluorophenoxy)-2-methyl-8-(pyridazin-3-yl)-2,3,4,5-tetrahydro-1H-benzo[c]azepine, tartrate salt Step A: To a solution of 3-bromobenzaldehyde (75.5 g, 408 mmol) in methanol (500 mL) at 0° C. was added methylamine (40% in aqueous, 38 g, 490 mmol), and iodine (1 g, 3.9 mmol). The mixture was stirred at 0° C. for 30 minutes.

Sodium borohydride (23.2 g, 614 mmol) was added in portions. The mixture was stirred at 0° C. for 5 hours. The solvent was removed, and the residue was taken up with water and dichloromethane. The organic layer was separated, washed with brine, dried over sodium sulfate and concentrated to give the benzylamine (80 g, crude) as a light yellow oil: $^1$H NMR (CDCl$_3$, 500 MHz) δ 7.48 (s, 1H), 7.38 (d, J=8.0 Hz, 1H), 7.24 (d, J=8.0 Hz, 1H), 7.19 (t, J=8.0 Hz, 1H), 3.72 (s, 1H), 2.46 (s, 3H); ESI MS m/z 200 [M+H]$^+$.

Step B: A solution of the benzylamine (26.4 g, 131 mmol) from Step A above, acrylic acid (9.5 g, 131 mmol) and pyridine (150 mL) was refluxed for 2 hours. The solvent was removed, and the residue was dried under vacuum to give the acid (37.6 g, crude) as a light yellow oil: $^1$H NMR (CDCl$_3$, 300 MHz) δ 7.75-7.68 (m, 2H), 7.48-7.43 (m, 2H), 3.67 (s, 2H), 2.84 (t, J=6.0 Hz, 2H), 2.56 (t, J=6.0 Hz, 2H), 2.34 (s, 3H); ESI MS m/z 272 [M+H]$^+$ Step C: A mixture of the acid (80 g, crude) from Step B above and triflic acid (350 g, 2333 mmol) was heated at 120° C. for 72 hours. After cooling to room temperature, the mixture was slowly diluted with water (1000 mL) at 0° C. The aqueous mixture was adjusted with NaOH to pH=9. The product was extracted with dichloromethane, washed with brine, dried over sodium sulfate and concentrated to give the ketone (38 g, crude): $^1$H NMR (CDCl$_3$, 500 MHz) δ 7.52-7.51 (m, 1H), 7.38-7.37 (m, 1H), 7.31-7.28 (m, 1H), 3.89 (s, 2H), 2.84 (m, 4H), 2.43 (s, 9H); ESI MS m/z 254 [M+H]$^+$.

Step D: To a solution of the ketone (1.9 g, 7.3 mmol) in methanol (20 mL) was added NaBH$_4$ (418 mg, 11.0 mmol) in portions at 0° C. The mixture was stirred at 0° C. for 1 hour. The solvent was removed, and the residue was taken up with dichloromethane/water. The organic layer was separated, washed with brine, dried over sodium sulfate, and concentrated to give the alcohol (2.1 g, crude) as a dark oil: $^1$H NMR (CDCl$_3$, 300 MHz) δ 7.60-7.42 (m, 1H), 7.37-7.33 (m, 1H), 7.26-7.23 (m, 1H), 4.86-4.82 (m, 1H), 3.90-3.84 (m, 1H), 3.72-3.67 (m, 1H), 3.22-3.18 (m, 1H), 2.90-2.82 (m, 1H), 2.34 (s, 3H), 2.14-2.07 (m, 1H), 1.95-1.91 (m, 1H); ESI MS m/z 256 [M+H]$^+$.

Step E: A mixture of the alcohol from Step D above (15.2 g, crude), tert-butyldimethylsilyl chloride (10 g, 66 mmol), imidazole (11.1 g, 166 mmol) and DMF (100 mL) was stirred at room temperature overnight. The mixture was diluted with water, saturated aqueous NaHCO$_3$ solution, brine, dried and concentrated. The residue was purified with chromatography (98:1.8:0.2 to 95:4.5:0.5 dichloromethane/methanol/concentrated ammonium hydroxide) to give the desired silyl ether (12 g, crude) as a brown oil: $^1$H NMR (CDCl$_3$, 300 MHz) δ 8.01 (s, 1H), 7.33 (d, J=7.9 Hz, 1H), 7.24 (d, J=7.9 Hz, 1H), 4.82 (t, J=4.9 Hz, 1H), 3.64-3.61 (m, 1H), 3.27-3.18 (m 1H), 2.36 (s, 3H), 1.95-1.85 (m, 2H), 1.80-1.63 (m, 2H), 0.91 (s, 9H), 0.097-0.085 (m, 6H); ESI MS m/z 370 [M+H]$^+$.

Step F: To a solution of the bromide (12 g, crude) from Step E in DMSO (120 mL) was added bis(pinacolato)diboron (8.7 g, 34.1 mmol) and potassium acetate (9.5 g, 97 mmol). The mixture was purged with argon. 1,1'-Bis(diphenylphosphino)ferrocenedichloropalladium (1.9 mg, 2.5 mmol) was added to the mixture. The reaction was heated at 85° C. for 1.5 hours. After cooling to room temperature, the reaction mixture was diluted with dichloromethane, and filtered through a pad of celite. The filtrate was washed with water, brine, dried over sodium sulfate and concentrated to give the desired boronate ester (19 g, crude) as a thick black liquid: ESI MS m/z 418 [M+H]$^+$.

Step G: The boronate ester (5.5 g, crude) from Step F above, 3-chloro-pyridazine (2.0 g, ~16 mmol), and cesium carbonate (4.2 g, 13 mmol) were suspended in DMF (30 mL) and water (8 mL). The mixture was purged with argon. 1,1'-Bis(diphenylphosphino)ferrocenedichloropalladium (400 mg, 0.52 mmol) was added to the mixture. The mixture was heated at 100° C. for 2 hours. After cooling to room temperature, the reaction mixture was diluted with dichloromethane, and filtered through a pad of celite. The filtrate was washed with water, brine, dried over sodium sulfate and concentrated. The residue was purified by flash chromatography (98:1.8:0.2 to 95:4.5:0.5 dichloromethane/methanol/concentrated ammonium hydroxide) to give 5-(tert-butyldimethylsilyloxy)-2-methyl-8-(pyridazin-3-yl)-2,3,4,5-tetrahydro-1H-benzo[c]azepine (1.3 g, 55% for 2 steps) as an brown oil: $^1$H NMR (CDCl$_3$, 300 MHz) δ 9.15 (d, J=4.8 Hz, 1H), 7.91-7.84 (m, 3H), 7.54-7.50 (m, 2H), 4.96 (t, J=5.2 Hz, 1H), 4.20-4.10 (m, 1H), 3.85-3.73 (m, 1H), 2.97-2.91 (m, 1H), 2.32 (s, 3H) d, J=7.9 Hz, 1H), 7.24 (d, J=7.9 Hz, 1H), 4.82 (t, J=4.9 Hz, 1H), 3.64-3.61 (m, 1H), 3.27-3.18 (m 1H), 2.36 (s, 3H), 1.95-1.85 (m, 2H), 1.80-1.63 (m, 2H), 0.91 (s, 9H), 0.097-0.085 (m, 6H); ESI MS m/z 370 [M+H]$^+$.

Step H: To the solution of the ether (1.3 g, 3.8 mmol) from Step G above in THF was added TBAF (1.0 M in THF, 10 mL, 10 mmol). The reaction mixture was stirred at room temperature for 3 hours. The solvent was removed. The residue was purified by flash chromatography (97:2.7:0.3 to 93:6.3:0.7 ethyl acetate/methanol/concentrated ammonium hydroxide) to give the desired alcohol (340 mg, 37%) as a white solid: ESI MS m/z 256 [M+H]$^+$.

Step J: To a solution of the 2-methyl-8-(pyridazin-3-yl)-2,3,4,5-tetrahydro-1H-benzo[c]azepin-5-ol (170 mg, 0.67) from Step H above in THF (5 mL) was added 4-fluorophenol (98 mg, 0.87 mmol), tributylphosphine (176 mg, 0.52 mmol) and 1,1'-(azodicarboyl)dipiperidine (220 mg, 0.87 mmol) at room temperature. The reaction mixture was stirred at room temperature for 3 hours. The mixture was diluted with dichloromethane and washed with water, brine, dried over sodium sulfate and concentrated. The residue was purified by chromatography (98:2 to 95:5 ethyl acetate/methanol), followed by preparative HPLC to give 544-fluorophenoxy)-2-methyl-8-(pyridazin-3-yl)-2,3,4,5-tetrahydro-1H-benzo[c]azepine (120 mg, 51%) as a gum-like solid. This compound was resolved using Chiralcel OJ column (eluente:80 Hep:20 EtOH:0.1 DEA) to give (+)-enantiomer (36 mg)) and (–)-enantiomer (37 mg).

Step K: To a solution of the (+)-enantiomer (36 mg, 0.10 mmol) from Step J above in methanol (1 mL) was added L-tartaric acid (16 mg, 0.11 mmol) followed by slow addition of water (5 mL). The resultant solution was lyophilized overnight to give (+)-5-(−4-fluorophenoxy)-2-methyl-8-(pyridazin-3-yl)-2,3,4,5-tetrahydro-1H-benzo[c]azepine, tartrate salt [46 mg, 88%, AUC HPLC>99%, [α]$^{25}_D$, +57.8°, (C, 0.19 Methanol) as a white solid: mp 96-98° C.; $^1$H NMR (CD$_3$OD, 500 MHz) δ 9.18 (d, J=4.9 Hz, 1H), 8.21-8.19 (m, 2H), 8.09 (d, J=8.0 Hz, 1H), 7.81 (dd, J=8.7, 3.8 Hz, 1H), 7.65 (d, J=8.0 Hz, 1H), 7.07-6.97 (m, 4H), 5.68 (d, J=8.0 Hz, 1H), 4.92-4.84 (m, 1H), 4.56-4.50 (m, 1H), 4.42 (s, 3H), 3.96-3.88 (m, 1H), 3.62-3.55 (m, 1H), 2.90 (s, 3H), 2.54-2.38 (m, 2H); ESI MS m/z 350 [M+H].

Step L: To a solution of the (−)-enantiomer (37 mg, 0.10 mmol) from Step J above in methanol (1 mL) was added L-tartaric acid (16 mg, 0.11 mmol) followed by slow addition of water (5 mL). The resultant solution was lyophilized overnight to give (−)-5-(4-fluorophenoxy)-2-methyl-8-(pyridazin-3-yl)-2,3,4,5-tetrahydro-1H-benzo[c]azepine, tartrate salt [47 mg, 88%, AUC HPLC>99%, [α]$^{25}_D$, 46.8°, (C, 0.22 Methanol) as a white solid: mp 90-92° C.; $^1$H NMR (CD$_3$OD, 500 MHz) δ 9.18 (d, J=4.9 Hz, 1H), 8.21-8.19 (m, 2H), 8.09 (d, J=8.0 Hz, 1H), 7.81 (dd, J=8.7, 3.8 Hz, 1H), 7.65

(d, J=8.0 Hz, 1H), 7.07-6.97 (m, 4H), 5.68 (d, J=8.0 Hz, 1H), 4.92-4.84 (m, 1H), 4.56-4.50 (m, 1H), 4.42 (s, 3H), 3.96-3.88 (m, 1H), 3.62-3.55 (m, 1H), 2.90 (s, 3H), 2.54-2.38 (m, 2H); ESI MS m/z 350 [M+H].

Example 18

Preparation of (−)-5-(naphthalen-2-yloxy)-2-methyl-8-(pyridazin-3-yl)-2,3,4,5-tetrahydro-1H-benzo[c]azepine, tartrate salt The above compound was prepared from 2-methyl-8-(pyridazin-3-yl)-2,3,4,5-tetrahydro-1H-benzo[c]azepin-5-ol from Step H in Example 17 and naphthalene-2-ol following the procedures of Steps J, K, and L in Example 17. (−)-5-(Naphthalen-2-yloxy)-2-methyl-8-(pyridazin-3-yl)-2,3,4,5-tetrahydro-1H-benzo[c]azepine, tartrate salt [AUC HPLC>99%, $[\alpha]^{25}{}_D$, −33°, (C, 0.033 Methanol) is a white solid: mp 120-122° C.; $^1$H NMR (CD$_3$OD, 500 MHz) δ 9.17 (d, J=4.9 Hz, 1H), 8.22 (s, 1H), 8.19 (d, J=8.7 Hz, 1H), 7.81-7.76 (m, 4H), 7.71 (d, J=8.3 Hz, 1H), 7.42-7.32 (m, 4H), 5.95 (d, J=8.1 Hz, 1H), 4.96-4.84 (m, 1H), 4.68-4.60 (m, 1H), 4.44 (s, 3H), 4.05-3.92 (m, 1H), 3.72-3.65 (m, 1H), 2.96 (s, 3H), 2.65-2.49 (m, 2H); ESI MS m/z 382 [M+H].

Example 19

Preparation of (±)-5-(4-fluorophenoxy)-2-methyl-8-(pyrimidin-5-yl)-2,3,4,5-tetrahydro-1H-benzo[c]azepine Step A: To a solution of 3-bromobenzaldehyde (75.5 g, 408 mmol) in methanol (500 mL) at 0° C. was added methylamine (40% aqueous solution, 38 g, 490 mmol), and iodine (1 g, 3.9 mmol). The mixture was stirred at 0° C. for 30 minutes. Sodium borohydride (23.2 g, 614 mmol) was added to the mixture in portions. The mixture was stirred at 0° C. for 5 hours. The solvent was removed under reduced pressure, and the residue was partitioned between water and dichloromethane. The organic layer was separated, washed with brine, dried over sodium sulfate, filtered and concentrated to give the benzylamine (80 g, crude) as a light yellow oil: $^1$H NMR (CDCl$_3$, 500 MHz) δ 7.48 (s, 1H), 7.38 (d, J=8.0 Hz, 1H), 7.24 (d, J=8.0 Hz, 1H), 7.19 (t, J=8.0 Hz, 1H), 3.72 (s, 2H), 2.46 (s, 3H); ESI MS m/z 200 [M+H]$^+$.

Step B: A solution of the benzylamine (26.4 g, 131 mmol) from Step A above, acrylic acid (9.5 g, 131 mmol) and pyridine (150 mL) was refluxed for 2 hours. The solvent was removed, and the residue was dried under vacuum to give the acid (37.6 g, crude) as a light yellow oil: $^1$H NMR (CDCl$_3$, 300 MHz) δ 7.68-7.75 (m, 2H), 7.48-7.43 (m, 2H), 3.67 (s, 2H), 2.84 (t, J=6.0 Hz, 2H), 2.56 (t, J=6.0 Hz, 2H), 2.34 (s, 3H); ESI MS m/z 272 [M+H]$^+$ Step C: A mixture of the acid (80 g, crude) from Step B above and triflic acid (350 g) was heated at 120° C. for 72 hours. The mixture cooled in an ice-bath and slowly diluted with water (1000 mL). The pH of aqueous mixture was adjusted pH=9 using NaOH. The product was extracted with dichloromethane, washed with brine, dried over sodium sulfate, filtered and concentrated to give the ketone (38 g, crude) as a dark oil: $^1$H NMR (CDCl$_3$, 500 MHz) δ 7.52-7.51 (m, 1H), 7.38-7.37 (m, 1H), 7.31-7.28 (m, 1H), 3.89 (s, 2H), 2.84 (m, 4H), 2.43 (s, 3H); ESI MS m/z 254 [M+H]$^+$.

Step D: To a solution of the ketone (1.9 g, 7.3 mmol) in methanol (20 mL) at 0° C. was added NaBH$_4$ (418 mg, 11.0 mmol) in portions. The mixture was stirred at 0° C. for 1 hour. The solvent was removed under reduced pressure, and the residue was partitioned between dichloromethane/water. The organic layer was separated, washed with brine, dried over sodium sulfate, filtered and concentrated to give the alcohol (2.1 g, crude) as a dark oil: $^1$H NMR (CDCl$_3$, 300 MHz) δ 7.60-7.42 (m, 1H), 7.37-7.33 (m, 1H), 7.26-7.23 (m, 1H), 4.86-4.82 (m, 1H), 3.90-3.84 (m, 1H), 3.72-3.67 (m, 1H), 3.22-3.18 (m, 1H), 2.90-2.82 (m, 1H), 2.34 (s, 3H), 2.14-2.07 (m, 1H), 1.95-1.91 (m, 1H); ESI MS m/z 256 [M+H]$^+$.

Step E: To a solution of the alcohol 3.0 g, crude) from Step D above in THF (87 mL) were added 4-fluorophenol (1.71 g, 15.2 mmol), tributylphosphine (3.8 mL, 15.2 mmol) and 1,1'-(azodicarboyl)dipiperidine (3.84 g, 15.2 mmol) at room temperature. The reaction mixture was stirred at room temperature for 5 hours, diluted with dichloromethane and washed with water and brine, dried over sodium sulfate, filtered and concentrated under reduced pressure. Purification of the residue by flash column chromatography (dichloromethane, then 99:0.9:0.1 to 90:9:1 dichloromethane/methanol/concentrated ammonium hydroxide) gave the partially purified aryloxyether, which was then sonicated in hexanes (~100 mL). The white insoluble precipitate formed was removed by filtration, and the filtrate was concentrated under reduced pressure and re-purified by flash column chromatography (ethyl acetate, then 99:1 to 95:5 ethyl acetate/methanol) to give the aryloxyether (2.5 g, partially pure) as a brown oil: $^1$H NMR (CDCl$_3$, 300 MHz) δ 7.34-7.31 (m, 2H), 7.18 (d, J=8.7 Hz, 1H), 6.93 (t, J=8.6 Hz, 2H), 6.84-6.79 (m, 2H), 5.24 (dd, J=7.8, 2.9 Hz, 1H), 4.00-3.75 (m, 2H), 3.40-3.20 (m, 1H), 3.10-2.90 (m, 1H), 2.32 (s, 3H), 2.20-2.05 (m, 2H).

Step F: To a solution of the bromide (2.5 g, partially pure) from Step E in DMSO (38 mL) were added bis(pinacolato) diboron (1.64 g, 6.48 mmol) and potassium acetate (1.73 g, 17.7 mmol). The mixture was purged with argon for ~10 minutes, and 1,1'-bis(diphenylphosphino)ferrocenedichloropalladium (140 mg, 0.18 mmol) was added to it. The reaction was heated at 80° C. for 2 hours. After cooling to room temperature, the reaction mixture was diluted with dichloromethane, washed with water and brine, dried over sodium sulfate, filtered and concentrated to give the desired boronate ester (3.0 g, crude) as a black oil which was used in the next step without purification: $^1$H NMR (CDCl$_3$, 500 MHz) δ 7.65 (d, J=7.6 Hz, 1H), 7.60 (s, 1H), 7.31 (d, J=7.4 Hz, 1H), 6.91 (t, J=8.6 Hz, 2H), 6.83-6.81 (m, 2H), 5.31-5.29 (m, 1H), 4.10-3.75 (m, 2H), 3.40-3.25 (m, 1H), 3.10-3.00 (m, 1H), 2.30 (s, 3H), 2.20-2.05 (m, 2H), 1.33-1.27 (m, 12H).

Step G: A mixture of the boronate ester (0.5 g, 0.98 mmol, crude) from Step F above, 5-bromopyrimidine (0.31 g, 1.96 mmol), and cesium carbonate (0.96 g, 2.94 mmol) in a solution of DMF (6 mL) and water (1.5 mL) was purged with argon for ~10 minutes. 1,1'-Bis(diphenylphosphino)ferrocenedichloropalladium (240 mg, 0.33 mmol) was added to the mixture, which was then heated at 80° C. for 3 hours. After cooling to room temperature, the reaction mixture was diluted with dichloromethane, washed with water and brine, dried over sodium sulfate, filtered and concentrated. The residue obtained was purified by preparative thin layer:chromatography (90:9:1 dichloromethane/methanol/concentrated ammonium hydroxide) twice to give the desired benzazepine (126 mg, 35% for 3 steps) as a brown oil: $^1$H NMR (CDCl$_3$, 300 MHz) δ 9.20 (s, 1H), 8.92 (s, 2H), 7.50-7.39 (m, 3H), 6.99-6.84 (m, 4H), 5.37 (dd, J=7.5, 3.2 Hz, 1H), 4.10-3.80 (m, 2H), 3.40-3.30 (m, 1H), 3.05-2.95 (m, 1H), 2.40 (s, 3H), 2.20-2.10 (m, 2H).

Example 20

Preparation of (±)-5-(4-fluorophenoxy)-2-methyl-8-(1H-pyrazol-4-yl)-2,3,4,5-tetrahydro-1H-benzo[c]azepine This compound was prepared by following the similar procedure in Step G of Example 19 using the bromide (0.25 g, 0.71 mmol, crude) from Step E of Example 19 above and 4-(4,4,5,5-tetramethyl-1,3,2-dioxaborolan-2-yl)-1H-pyrazole.

The product was obtained as a brown foam (40% yield): MS m/z 338 [M+H]$^+$.

Example 21

Preparation of (±)-6-(5-(4-fluorophenoxy)-2-methyl-2,3,4,5-tetrahydro-1H-benzo[c]azepin-8-yl)pyridazin-3-amine This compound was prepared by following the similar procedure in Step G of Example 19 using boronate ester from Step F of Example 19 and 6-chloropyridazin-3-amine. The product was obtained as brown oil (37% yield): MS m/z 365 [M+H]$^+$.

Example 22

Preparation of (±)-8-(4-(ethylsulfonyl)piperazin-1-yl)-5-(4-fluorophenoxy)-2-methyl-2,3,4,5-tetrahydro-1H-benzo[c]azepine This compound was prepared by using the bromide from Step E of Example 19 and 1-(ethylsulfonyl)piperazine via a cross coupling reaction using Pd(OAc)$_2$, X-phos and Cs$_2$CO$_3$ in refluxing toluene (31% yield): MS m/z 448 [M+H]$^+$.

Example 23

Preparation of (+)- and (−)-2-methyl-5-(4-(trifluoromethyl)phenoxy)-2,3,4,5-tetrahydro-1H-benzo[c]azepine, tartrate salt Step A: A solution of the benzylamine (47.2 g, 390 mmol), acrylic acid (29.5 g, 410 mmol) and pyridine (500 mL) was refluxed for 3 hours. The solvent was removed, and the residue was dried under vacuum to give the desired acid (80 g, crude) as a light yellow oil: $^1$H NMR (CDCl$_3$, 300 MHz) δ 7.38-7.29 (m, 5H), 3.74 (s, 2H), 2.87 (t, J=6.2 Hz, 2H), 2.56 (t, J=6.2 Hz, 2H), 2.35 (s, 3H); ESI MS m/z 194 [M+H]$^+$.

Step B: A mixture of the acid (15.3 g, crude) from step B above and thionyl chloride (18.9 g, 180 mmol) was combined and stirred for 2 hours. Excess thionyl chloride was removed. The residue was dissolved in dichloromethane (200 mL). To this solution was added AlCl$_3$ (31.7 g, 240 mmol). The mixture was refluxed for 5 hours. The mixture was poured into ice-water, and the resulting slurry was neutralized to pH 9. Celite (50 g) was mixed with the slurry, and the mixture was filtered, and washed with dichloromethane. The filtrate was washed with brine, dried and concentrated to give the desired lactone (9.2 g, crude) as a brown oil: $^1$H NMR (CDCl$_3$, 300 MHz) δ 7.77 (d, J=6.2 Hz, 1H), 7.47 (t, J=6.2 Hz, 1H), 7.37 (t, J=6.2 Hz, 1H), 7.19 (d, J=6.2 Hz, 1H), 3.94 (s, 2H), 2.95-2.82 (m, 4H), 2.43 (s, 3H); ESI MS m/z 176 [M+H]$^+$.

Step C: To a solution of the lactone form step C above (9.2 g, crude) in methanol (100 mL) was added NaBH$_4$ (3 g, crude) in portions at 0° C. The mixture was stirred at 0° C. for 0.5 hour. The solvent was removed, and the residue was taken up with dichloromethane/water. The organic layer was separated, washed with brine, dried and concentrated to give the desired alcohol (6.3 g, crude) as a dark oil: ESI MS m/z 178 [M+H]$^+$.

Step D: To a solution of the alcohol (270 mg, 1.53 mmol) from step C above in THF (50 mL) was added 4-trifluoromethoxyphenol (442 mg, 3.1 mmol), tributylphosophine (615 mg, 3.1 mmol) and 1,1'-(azodicarboyl)dipiperidine (772 mg, 3.1 mmol) at room temperature. The reaction mixture was stirred at room temperature for 5 hours. The mixture was diluted with dichloromethane and washed with water, brine, dried and concentrated. The residue was purified by chromatography (98:1.8:0.2 to 95:4.5:0.5 dichloromethane/methanol/concentrated ammonium hydroxide) to give the aryloxyether (300 mg, 62%) as a light yellow oil: ESI MS m/z 332 [M+H]$^+$.

Step E: The free base of benzazepine from Step H above was resolved by preparative chiral HPLC(CHIRALCEL OJ column, using 80:20:0.1 heptane/ethanol/diethylamine as the eluente) to give enantiomer A and enantiomer B.

Step F: To a solution of the enantiomer A (100 mg, 0.31 mmol) from step E above in methanol (1 mL) was added L-tartaric acid (48 mg, 0.32 mmol) followed by slow addition of water (5 mL). The resultant solution was lyophilized overnight to give (−)-2-methyl-5-(4-trifluoromethoxyphenoxy)-2,3,4,5-tetrahydro-1H-benzo[c]azepine, tartrate salt (148 mg, 100%, AUC HPLC 97.8%) as an off-white solid: mp 86-88° C.; ESI MS m/z 322 [M+H].

Step G: To a solution of the enantiomer B (130 mg, 0.40 mmol) from step E above in methanol (1 mL) was added L-tartaric acid (61 mg, 0.40 mmol) followed by slow addition of water (5 mL). The resultant solution was lyophilized overnight to give (+)-2-methyl-5-(4-trifluoromethoxyphenoxy)-2,3,4,5-tetrahydro-1H-benzo[c]azepine, tartrate salt (191 mg, 100%, AUC HPLC 97.2%) as an off-white solid: mp 88-90° C.; ESI MS m/z 322 [M+H].

Example 24

Preparation of (±)-5-(4-fluorophenoxy)-2-methyl-8-(pyrazin-2-yl)-2,3,4,5-tetrahydro-1H-benzo[c]azepine This compound was prepared by following the similar procedure in Step G of Example 19 using boronate ester from Step F of Example 19 and 2-chloropyrizine. The product was obtained as an white foam (40% yield): MS m/z 350 [M+H]$^+$.

Example 25

Preparation of (±)-6-(5-(4-fluorophenoxy)-2-methyl-2,3,4,5-tetrahydro-1H-benzo[c]azepin-8-yl)pyridin-2-amine This compound was prepared by following the similar procedure in Step G of Example 19 using the boronate ester (0.35 g, 0.88 mmol, crude) from Step F of Example 19 and 6-chloropyridin-2-amine. The product was obtained as an off-white foam (40% yield): MS m/z 364 [M+H]$^+$.

Example 26

Preparation of (±)-6-(5-(4-fluorophenoxy)-2-methyl-2,3,4,5-tetrahydro-1H-benzo[c]azepin-8-yl)pyridazin-3(2H)-one This compound was prepared by following the similar procedure in Step G of Example 19 using the boronate ester (0.32 g, 0.81 mmol, crude) from Step F of Example 19 and 6-chloropyridazin-3(2H)-one. The product was obtained an off-white foam (17% yield): MS m/z 366 [M+H]⁺.

Example 27

Preparation of (±)-5-(4-fluorophenoxy)-2-methyl-8-(4-(methylsulfonyl)phenyl)-2,3,4,5-tetrahydro-1H-benzo[c]azepine This compound was prepared by following the similar procedure in step G of Example 19 using the bromide (0.35 g, 1.0 mmol, crude) from Step E of Example 19 and 4-(methylsulfonyl)phenylboronic acid. The product was obtained as a light tan solid (54% yield): MS m/z 426 [M+H]⁺.

Example 28

Preparation of (±)-2-(5-(4-fluorophenoxy)-2-methyl-2,3,4,5-tetrahydro-1H-benzo[c]azepin-8-yl)benzonitrile This compound was prepared by following the similar procedure in Step G of Example 19 using the bromide (0.35 g, 1.0 mmol, crude) from Step E of Example 19 and 2-cyanophenylboronic acid, (64% yield): MS m/z 373 [M+H]⁺.

Example 29

Preparation of (±)-8-([1,2,4]triazolo[1,5-a]pyridin-6-yl)-5-(4-fluorophenoxy)-2-methyl-2,3,4,5-tetrahydro-1H-benzo[c]azepine This compound was prepared by following the similar procedure in Step G of Example 19 using the boronate ester from Step F of Example 19 and 6-bromo-[1,2,4]triazolo[1,5-a]pyridine. The product was obtained as an white foam (32% yield): MS m/z 389 [M+H]⁺.

Example 30

Preparation of (±)-8-([1,2,4]triazolo[4,3-a]pyridin-6-yl)-5-(4-fluorophenoxy)-2-methyl-2,3,4,5-tetrahydro-1H-benzo[c]azepine This compound was prepared by following the similar procedure in Step G of Example 19 using the boronate ester from Step E of Example 19 and 6-bromo-[1,2,4]triazolo[4,3-a]pyridine (23% yield): MS m/z 389 [M+H]⁺.

Example 31

Preparation of (±)-1-(5-(4-fluorophenoxy)-2-methyl-2,3,4,5-tetrahydro-1H-benzo[c]azepin-8-yl)pyridin-2(1H)-one Step A: To a solution of 3-bromobenzaldehyde (75.5 g, 408 mmol) in methanol (500 mL) at 0° C. was added methylamine (40% aqueous solution, 38 g, 490 mmol), and iodine (1 g, 3.9 mmol). The mixture was stirred at 0° C. for 30 minutes. Sodium borohydride (23.2 g, 614 mmol) was added to the mixture in portions. The mixture was stirred at 0° C. for 5 hours. The solvent was removed under reduced pressure, and the residue was partitioned between water and dichloromethane. The organic layer was separated, washed with brine, dried over sodium sulfate, filtered and concentrated to give the benzylamine (80 g, crude) as a light yellow oil: ¹H NMR (CDCl₃, 500 MHz) δ 7.48 (s, 1H), 7.38 (d, J=8.0 Hz, 1H), 7.24 (d, J=8.0 Hz, 1H), 7.19 (t, J=8.0 Hz, 1H), 3.72 (s, 2H), 2.46 (s, 3H); ESI MS m/z 200 [M+H]⁺.

Step B: A solution of the benzylamine (26.4 g, 131 mmol) from Step A above, acrylic acid (9.5 g, 131 mmol) and pyridine (150 mL) was refluxed for 2 hours. The solvent was removed, and the residue was dried under vacuum to give the acid (37.6 g, crude) as a light yellow oil: ¹H NMR (CDCl₃, 300 MHz) δ 7.68-7.75 (m, 2H), 7.48-7.43 (m, 2H), 3.67 (s, 2H), 2.84 (t, J=6.0 Hz, 2H), 2.56 (t, J=6.0 Hz, 2H), 2.34 (s, 3H); ESI MS m/z 272 [M+H]⁺

Step C: A mixture of the acid (80 g, crude) from Step B above and triflic acid (350 g) was heated at 120° C. for 72 hours. The mixture cooled in an ice-bath and slowly diluted with water (1000 mL). The pH of aqueous mixture was adjusted pH=9 using NaOH. The product was extracted with dichloromethane, washed with brine, dried over sodium sulfate, filtered and concentrated to give the ketone (38 g, crude) as a dark oil: ¹H NMR (CDCl₃, 500 MHz) δ 7.52-7.51 (m, 1H), 7.38-7.37 (m, 1H), 7.31-7.28 (m, 1H), 3.89 (s, 2H), 2.84 (m, 4H), 2.43 (s, 3H); ESI MS m/z 254 [M+H]⁺.

Step D: To a solution of the ketone (1.9 g, 7.3 mmol) in methanol (20 mL) at 0° C. was added NaBH₄ (418 mg, 11.0 mmol) in portions. The mixture was stirred at 0° C. for 1 hour. The solvent was removed under reduced pressure, and the residue was partitioned between dichloromethane/water. The organic layer was separated, washed with brine, dried over sodium sulfate, filtered and concentrated to give the alcohol (2.1 g, crude) as a dark oil: ¹H NMR (CDCl₃, 300 MHz) δ 7.60-7.42 (m, 1H), 7.37-7.33 (m, 1H), 7.26-7.23 (m, 1H), 4.86-4.82 (m, 1H), 3.90-3.84 (m, 1H), 3.72-3.67 (m, 1H), 3.22-3.18 (m, 1H), 2.90-2.82 (m, 1H), 2.34 (s, 3H), 2.14-2.07 (m, 1H), 1.95-1.91 (m, 1H); ESI MS m/z 256 [M+H]⁺.

Step E: To a solution of the alcohol (3.0 g, crude) from Step D above in THF (87 mL) was added 4-fluorophenol (1.71 g, 15.2 mmol), tributylphosphine (3.8 mL, 15.2 mmol) and 1,1'-(azodicarboyl)dipiperidine (3.84 g, 15.2 mmol) at room temperature. The reaction mixture was stirred at room temperature for 5 hours, diluted with dichloromethane and washed with water and brine, dried over sodium sulfate, filtered and concentrated under reduced pressure. Purification of the residue by flash column chromatography (dichloromethane, then 99:0.9:0.1 to 90:9:1 dichloromethane/methanol/concentrated ammonium hydroxide) gave the partially purified aryloxyether, which was then sonicated in hexanes (~100 mL). The white insoluble precipitate formed was removed by filtration, and the filtrate was concentrated under reduced pressure and re-purified by flash column chromatography (ethyl acetate, then 99:1 to 95:5 ethyl acetate/methanol) to give 8-bromo-5-(4-fluorophenoxy)-2-methyl-2,3,4,5-tetrahydro-1H-benzo[c]azepine (2.5 g, partially pure) as a brown oil: ¹H NMR (CDCl₃, 300 MHz) δ 7.34-7.31 (m, 2H), 7.18 (d, J=8.7 Hz, 1H), 6.93 (t, J=8.6 Hz, 2H), 6.84-6.79 (m, 2H), 5.24 (dd, J=7.8, 2.9 Hz, 1H), 4.00-3.75 (m, 2H), 3.40-3.20 (m, 1H), 3.10-2.90 (m, 1H), 2.32 (s, 3H), 2.20-2.05 (m, 2H).

Step F: To a solution of the bromide from Step E (0.4 g, 1.1 mmol, slightly impure) and 2-hydroxy-pyridine (0.13 g, 1.37 mmol) from Step E in 1,4-dioxane (1.4 mL) were added N,N'-dimethylethylenediamine (50 µL, 0.46 mmol) and potassium phosphate (0.48 g, 2.30 mmol). The mixture was purged with argon for ~10 minutes, and copper (I) iodide (40 mg, 0.2 mmol) was added to it. The reaction was heated at 110° C. for 12 hours. After cooling to room temperature, the reaction mixture was diluted with dichloromethane, washed with water and brine, dried over sodium sulfate, filtered and concentrated to give the crude product. Purification by preparative thin layer chromatography (90:9:1 dichloromethane/methanol/concentrated ammonium hydroxide) twice gave the desired product (144 mg, 36%) as an off-white foam: $^1$H NMR (CDCl$_3$, 300 MHz) δ 7.45-7.26 (m, 3H), 7.25-7.21 (m, 2H), 6.95 (t, J=8.6 Hz, 2H), 6.88-6.83 (m, 2H), 6.64 (d, J=9.2 Hz, 1H), 6.30-6.25 (m, 1H), 5.36-5.30 (m, 1H), 4.05-3.83 (m, 2H), 3.35-3.20 (m, 1H), 3.10-3.00 (m, 1H), 2.37 (s, 3H), 2.20-2.13 (m, 2H).

Example 32

Preparation of (−)-8-(6-methylpyridazin-3-yl)-5-phenoxy-2,3,4,5-tetrahydro-1H-benzo[c]azepine, tartrate salt Step A: To a solution of the enantiomer B (120 mg, 0.18 mmol, as the tartrate) from step I in Example 16 in dichloroethane (6 mL) was added the proton sponge (114 mg, 0.53 mmol), followed by 1-chloroethyl chloroformate (102 mg, 0.71 mmol) at 0° C. The mixture was then heated at reflux for 1.5 hours. The solvent was removed. To the residue was added MeOH (20 mL), and the resultant mixture was refluxed for 1 hour. After cooling to room temperature, the solvent was removed. The residue was diluted with dichloromethane (20 mL), and washed with saturated aqueous NaHCO$_3$ solution, brine, dried over sodium sulfate, and concentrated. The residue was purified by flash chromatography (98:1.8:0.2 to 95:4.5:0.5 dichloromethane/methanol/concentrated ammonium hydroxide) to give (−)-8-(6-methylpyridazin-3-yl)-5-phenoxy-2,3,4,5-tetrahydro-1H-benzo[c]azepine (16 mg, 27%) as a colorless semi-solid.

Step B: To a solution of the N-desmethylbenzazepine (16 mg, 0.048 mmol) from Step A above in MeOH (1 mL) was added L-tartaric acid (8 mg, 0.053 mmol) followed by slow addition of water (5 mL). The resultant solution was lyophilized overnight to give (−)-N-desmethyl-8-(6-methylpyridazin-3-yl)-5-phenoxy-2,3,4,5-tetrahydro-1H-benzo[c]azepine, tartrate salt (24 mg, quant., AUC HPLC 98.9%) as a off-white solid: mp 115-118° C.; $^1$H NMR (CD$_3$OD, 500 MHz) δ 8.15 (s, 1H), 8.08-8.04 (m, 2H), 7.69-7.67 (m, 1H), 7.27-7.24 (m, 1H), 7.06-7.04 (m, 2H), 6.96-6.93 (m, 1H), 5.80-5.78 (m, 1H), 4.90-4.84 (m, 1H), 4.55-4.50 (m, 1H), 4.42 (s, 3H), 3.94-3.84 (m, 1H), 3.65-3.55 (m, 1H), 2.74 (s, 3H), 2.58-2.50 (m, 1H), 2.63-2.45 (m, 1H); ESI MS m/z 332 [M+H].

Example 33

Preparation of (−)-2-methyl-8-(pyridazin-3-yl)-5-(quinolin-7-yloxy)-2,3,4,5-tetrahydro-1H-benzo[c]azepine, tartrate salt (+)-2-Methyl-8-(pyridazin-3-yl)-2,3,4,5-tetrahydro-1H-benzo[c]azepin-5-o 1 was obtained following the procedure of Step H in Example 1 from (+)-5-(tert-butyldimethylsilyloxy)-2-methyl-8-(pyridazin-3-yl)-2,3,4,5-tetrahydro-1H-benzo[c]azepine in Step G of Example 1. Ether formation between (+)-2-methyl-8-(pyridazin-3-yl)-2,3,4,5-tetrahydro-1H-benzo[c]azepin-5-ol and 7-hydroxyquinoline using procedures similar to those in Step B and C of Example 10 gave (−)-2-methyl-8-(pyridazin-3-yl)-5-(quinolin-7-yloxy)-2,3,4,5-tetrahydro-1H-benzo[c]azepine, tartrate salt (AUC HPLC 98.3%) as a white solid: [α]$^{25}_D$-168° (c 0.22, MeOH); mp 120-122° C.; ESI MS m/z 383 [M+H].

Example 34

Preparation of (−)-5-(2-chlorophenoxy)-2-methyl-8-(pyridazin-3-yl)-2,3,4,5-tetrahydro-1H-benzo[c]azepine, tartrate salt (+)-2-Methyl-8-(pyridazin-3-yl)-2,3,4,5-tetrahydro-1H-benzo[c]azepin-5-ol was obtained following the procedure of Step H in Example 1 from (+)-5-(tert-butyldimethylsilyloxy)-2-methyl-8-(pyridazin-3-yl)-2,3,4,5-tetrahydro-1H-benzo[c]azepine in Step G of Example 1. Ether formation between (+)-2-methyl-8-(pyridazin-3-yl)-2,3,4,5-tetrahydro-1H-benzo[c]azepin-5-ol and 2-chlorophenol using procedures similar to those in Step B and C of Example 10 gave (−) -5-(3-chlorophenoxy)-2-methyl-8-(pyridazin-3-yl)-2,3,4,5-tetrahydro-1H-benzo[c]azepine, tartrate salt (AUC HPLC>99%) as a white solid: mp 100-102° C.; 1H NMR (CD3OD, 500 MHz) δ 9.18 (d, J=5.0 Hz, 1H), 8.20-8.18 (m, 2H), 8.09 (d, J=8.0 Hz, 1H), 7.83-7.80 (m, 1H), 7.68 (d, J=8.0 Hz, 1H), 7.24 (t, J=8.2 Hz, 1H), 7.14-7.13 (m, 1H), 7.02 (d, J=8.2 Hz, 1H), 6.97 (d, J=8.0 Hz, 1H), 5.79 (d, J=7.9 Hz, 1H), 4.86-4.79 (m, 1H), 4.55-4.48 (m, 1H), 4.42 (s, 2H), 3.90-3.85 (m, 1H), 3.60-3.54 (m, 1H), 2.88 (s, 3H), 2.55-2.40 (m, 2H); ESI MS m/z 366 [M+H].

Example 35

Preparation of (−)-5-(2-chlorophenoxy)-2-methyl-8-(pyridazin-3-yl)-2,3,4,5-tetrahydro-1H-benzo[c]azepine, tartrate salt (+)-2-Methyl-8-(pyridazin-3-yl)-2,3,4,5-tetrahydro-1H-benzo[c]azepin-5-ol was obtained following the procedure of Step H in Example 1 from (+)-5-(tert-butyldimethylsilyloxy)-2-methyl-8-(pyridazin-3-yl)-2,3,4,5-tetrahydro-1H-benzo[c]azepine in Step G of Example 1. Ether formation between (+)-2-methyl-8-(pyridazin-3-yl)-2,3,4,5-tetrahydro-1H-benzo[c]azepin-5-ol and 2-chlorophenol using procedures similar to those in Step B and C of Example 10 gave (−) -5-(2-chlorophenoxy)-2-methyl-8-(pyridazin-3-yl)-2,3,4,5-tetrahydro-1H-benzo[c]azepine, tartrate salt (AUC HPLC 98.6%) as a white solid: mp 104-106° C.; 1H NMR (CD3OD, 500 MHz) δ 9.20-9.19 (m, 1H), 8.23-8.21 (m, 2H), 8.13-8.11 (m, 1H), 7.84-7.82 (m, 1H), 7.73-7.72 (m, 1H), 7.41-7.40 (m, 1H), 7.25-7.19 (m, 2H), 6.98-6.96 (m, 1H), 5.85-5.84 (m, 1H), 5.20-5.05 (m, 1H), 4.51-4.43 (m, 3H), 4.00-3.92 (m, 1H), 3.66-3.61 (m, 2H), 2.91 (s, 3H), 2.58-2.44 (m, 2H); ESI MS m/z 366 [M+H].

Example 36

Preparation of (+/−)-2-(5-(3,5-difluorophenoxy)-2,3,4,5-tetrahydro-1H-benzo[c]azepin-8-yl)-[1,2,4]triazolo[4,3-a]pyridin-3(2H)-one, tartrate salt Step A: To a solution of the alcohol (0.5 g, 1.95) from step D in Example 19 in THF (40 mL) were added 3,5-difluorophenol (0.38 g, 2.93 mmol), tributylphosphine (0.73 mL, 2.93 mmol) and 1,1'-(azodicarboyl)dipiperidine (0.74 g, 2.93 mmol) at room temperature. The reaction mixture was stirred at room temperature for 90 minutes, and filtered through celite. The filtrate was diluted with hexanes, and the additional precipitate formed was removed via filtration as well. The filtrate was concentrated under reduced pressure to give a brown oil. Purification of the residue by flash column chromatography (chloroform, then 99:1 to 80:20 chloroform/isopropanol) gave the partially purified aryloxyether (0.4 g)

which was used without further purification: ¹H NMR (CDCl₃, 500 MHz) δ 7.37-7.32 (m, 2H), 7.16 (d, J=8.1 Hz, 1H), 6.43-6.39 (m, 3H), 5.30-5.27 (m, 1H), 4.05-3.63 (m, 2H), 3.37-3.21 (m, 1H), 3.10-2.94 (m, 1H), 2.32 (s, 3H), 2.21-1.95 (m, 2H).

Step B: To a solution of the bromide (0.3 g, 0.8 mmol, partially pure) from step A in 1,4-dioxane (1 mL) were added pyridazin-3(2H)-one (94 mg, 0.98 mmol), N,N'-dimethylethylenediamine (35 μL, 0.33 mmol), and potassium phosphate (0.35 g, 1.63 mmol). The mixture was purged with argon, and copper (I) iodide (31 mg, 0.16 mmol) was added to it. The reaction was heated at 110° C. for 16 hours. After cooling to room temperature, the reaction mixture was diluted with dichloromethane, washed with water and brine, dried over sodium sulfate, filtered and concentrated to give the crude product. Purification by reverse phase semi-preparative HPLC (5% B to 50% B over 35 min; A=95:5 water/acetonitrile+0.05% TFA, B=95:5 acetonitrile/water+0.05% TFA), and conversion into the corresponding free base using 2N sodium carbonate gave the coupled product (202 mg, 64%) as a pale yellow foam: ¹H NMR (CDCl₃, 500 MHz) δ 7.89 (dd, J=3.8, 1.7 Hz, 1H), 7.51-7.48 (m, 2H), 7.40 (d, J=8.2 Hz, 1H), 7.27-7.22 (m, 2H), 7.05-7.03 (m, 1H), 6.46-6.40 (m, 3H), 5.38 (dd, J=9.2, 1.1 Hz, 1H), 4.05-3.79 (m, 2H), 3.37-3.26 (m, 1H), 3.10-2.95 (m, 1H), 2.32 (s, 3H), 2.26-2.05 m, 2H).

Step C: To an ice-cold solution of the benzazepine (0.17 g, 0.39 mmol) from step B and 1,8-bis(dimethylamino)naphthalene (Proton-Sponge, 0.25 g, 1.18 mmol) in 1,2-dichloroethane (4.6 mL) was added 1-chloroethyl chloroformate (0.21 mL, 1.98 mmol) dropwise. The reaction mixture was stirred at 0° C. for 3 hours, and then washed with 1N hydrochloric acid. The organic layer was separated, and the aqueous layer was washed with dichloromethane. The combined organic extract was dried over magnesium sulfate, filtered and concentrated under reduced pressure, and methanol (4.2 mL) was added to the residue. The solution was heated under reflux for 2 hours, and concentrated under reduced pressure. Purification by preparative thin layer chromatography (90:9:1 dichloromethane/methanol/concentrated ammonium hydroxide) gave partially pure material. Re-purification by preparative thin layer:chromatography (95:4.5:0.5 dichloromethane/methanol/concentrated ammonium hydroxide), followed by reverse phase semi-preparative HPLC (30% B to 50% B; A=95:5 water/acetonitrile+0.05% TFA, B=95:5 acetonitrile/water+0.05% TFA), and conversion into the corresponding free base using 2N sodium carbonate gave the N-desmethyl product (45 mg, 28%): ¹H NMR (300 MHz, CDCl₃) δ 7.98-7.83 (m, 3H), 7.52-7.47 (m, 1H), 7.28-7.21 (m, 2H), 6.67-6.50 (m, 3H), 6.50-6.40 (m, 1H), 5.70-5.60 (m, 1H), 4.30-4.10 (m, 1H), 4.00-3.90 (m, 1H), 3.60-3.40 (m, 1H), 3.30-3.20 (m, 1H), 2.20-2.00 (m, 2H).

To a solution of the N-desmethyl derivative (44 mg, 0.11 mmol) in methanol (1.5 mL) was added L-tartaric acid (16 mg, 0.11 mmol), followed by water (6 mL). The resultant solution was lyophilized overnight to give 2-(5-(3,5-difluorophenoxy)-2,3,4,5-tetrahydro-1H-benzo[c]azepin-8-yl)-[1,2,4]triazolo[4,3-a]pyridin-3(2H)-one (60 mg, >99%, AUC HPLC 98.2%) as an off-white solid: ¹H NMR (CD₃OD, 500 MHz) δ 8.21 (d, J=2.0 Hz, 1H), 8.14 (dd, J=8.4, 2.1 Hz, 1H), 7.86 (d, J=7.1, 1.2 Hz, 1H), 7.65 (d, J=8.4 Hz, 1H), 7.32-7.21 (m, 2H), 6.76-6.60 (m, 3H), 6.59-6.50 (m, 1H), 5.79 (d, J=7.4 Hz, 1H), 4.74 (d, J=14.6 Hz, 1H), 4.69-4.40 (m, 1H), 4.40 (s, 2H), 3.90-3.80 (m, 1H), 3.65-3.45 (m, 1H), 2.60-2.30 (m, 2H); ESI MS m/z 409 [M+H]⁺.

Example 37

Preparation of (+)- and (−)-8-([1,2,4]triazolo[1,5-a]pyridin-6-yl)-5-(3,5-difluorophenoxy)-2,3,4,5-tetrahydro-1H-benzo[c]azepine, tartrate salt Step A: To a solution of N-methyl benzazepine (1.5 g, 4.1 mmol) from Step A in Example 36 above was added proton sponge (1.3 g, 6.2 mmol), followed by 1-chloroethyl chloroformate (0.49 mL, 4.5 mmol). The reaction solution was stirred at room temperature for 2 hours and then it was diluted with dichloromethane and washed with aqueous HCl (1 N). The organic layer was separated, dried over sodium sulfate and concentrated in vacuo. The residue obtained was dissolved in methanol and refluxed for 90 minutes. The reaction solution was then cooled to room temperature, concentrated in vacuo. The residue obtained was dissolved in dichloromethane, washed with aqueous sodium bicarbonate, dried over sodium sulfate and concentrated in vacuo. The crude product obtained was purified by flash column chromatography (dichloromethane/methanol/concentrated ammonium hydroxide 99:0.9:0.1 to 92:7.2:0.8) to give the des-methyl benzazepine (1.14 g, 78%) as a dark oil: ¹H NMR (CDCl₃, 500 MHz) δ 7.35-7.31 (m, 2H), 7.18 (d, J=8.5 Hz, 1H), 6.43-6.38 (m, 3H), 5.35 (dd, J=7.5, 3.0 Hz, 1H), 4.10 (d, J=15.0 Hz, 1H), 3.87 (d, J=15.0 Hz, 1H), 3.51-3.46 (m, 1H), 3.24-3.19 (m, 1H), 2.20-1.99 (m, 2H).

Step B: To a solution of the des-methyl benzazepine (1.14 g, 2.1 mmol) from step A above in dichloromethane (30 mL) was added diisopropyl ethylamine (0.46 mL, 2.6 mmol) and 2-nitrobenzene-1-sulfonyl chloride (0.49 g, 2.2 mmol). The reaction solution was stirred at room temperature for 2 hours and then it was washed with aqueous sodium bicarbonate and 1N HCl. The resultant organic layer was dried over sodium sulfate and concentrated in vacuo. The crude product obtained was purified by flash column chromatography (hexanes/ethyl acetate 95:5 to 50:50) to give the desired N-protected benzazepine (1.1 g, 63%): ¹H NMR (500 MHz, CDCl₃) δ 7.79 (dd, J=8.0, 1.0 Hz, 1H), 7.72-7.62 (m, 3H), 7.45 (d, J=1.5 Hz, 1H), 7.40 (dd, J=8.0, 2.0 Hz, 1H), 7.16 (d, J=8.0 Hz, 1H), 6.43-6.39 (m, 3H), 5.34 (dd, J=7.0, 2.0 Hz, 1H), 4.72 (d, J=14.5 Hz, 1H), 4.49 (d, J=15.5 Hz, 1H), 3.93-3.74 (m, 2H), 2.32-2.20 (m, 2H).

Step C: To a solution of the bromide (1.1 g, 2.0 mmol) from step B above in DMSO (20 mL) were added bis(pinacolato)diboron (0.62 g, 2.4 mmol) and potassium acetate (0.59 g, 6.0 mmol). The mixture was purged with argon for about 10 minutes, and 1,1'-bis(diphenylphosphino)ferrocenedichloropalladium (0.12 g, 0.16 mmol) was added to it. The reaction was heated at 80° C. for 3 hours. After cooling to room temperature, the reaction mixture was diluted with ethyl acetate, washed with water and brine, dried over sodium sulfate, filtered, and concentrated in vacuo. The crude product obtained was partially purified by flash column chromatography (hexanes/ethyl acetate 95:5 to 60:40) to give the desired boronate ester (1.4 g, partially pure) as a yellow foam.

Step D: A mixture of the boronate ester (0.45 g, 0.76 mmol, partial pure) from step C above, 6-bromo-[1,2,4]triazolo[1,5-a]pyridine (0.18 g, 0.92 mmol), and cesium carbonate (0.74 g, 2.3 mmol) in a solution of DMF (8 mL) and water (2 mL) was purged with argon for about 10 minutes. 1,1'-Bis(diphenylphosphino)ferrocenedichloropalladium (56 mg, 0.076 mmol) was added to the mixture, which was then heated at 80° C. for 2 hours. After cooling to room temperature, the reaction mixture was diluted with dichloromethane, washed with water and brine, dried over sodium sulfate, filtered, and concentrated in vacuo. The residue obtained was purified by flash column chromatography (dichloromethane/methanol 99:1 to 96:4), followed by preparative thin layer chromatography (dichloromethane/methanol 95:5) to give benzazepine (0.27 g, partially pure) as a yellow solid, which was used in the next step without further purification.

Step E: To a solution of the protected benzazepine (0.27 g, partially pure) from step D in a mixture of dichloromethane (2 mL) and ethanol (8 mL) were added potassium carbonate (0.18 g, 1.3 mmol) and thiophenol (0.10 mL, 0.92 mmol). The reaction mixture was stirred at room temperature for 36 hours and then it was quenched with aqueous sodium hydroxide (2N), extracted with dichloromethane and a 3:1 mixture of chloroform and 2-propanol. The combined organic extract was dried over sodium sulfate and concentrated in vacuo. The crude product obtained was purified by flash column chromatography (dichloromethane/methanol/concentrated ammonium hydroxide 99:0.9:0.1 to 90:9:1) to give the desmethyl benzazepine (102 mg, 59%) as a white foam: $^1$H NMR (500 MHz, CDCl$_3$) δ 8.77 (s, 1H), 8.37 (s, 1H), 7.83 (d, J=8.5 Hz, 1H), 7.76 (dd, J=8.5, 1.5 Hz, 1H), 7.46-7.43 (m, 2H), 7.40 (s, 1H), 6.50-6.40 (m, 3H), 5.50-5.47 (m, 1H), 4.24 (d, J=15.0 Hz, 1H), 4.01 (d, J=15.0 Hz, 1H), 3.57-3.52 (m, 1H), 3.31-3.25 (m, 1H), 2.21-2.11 (m, 2H). The racemic benzazepine was then resolved by preparative chiral HPLC(CHIRALCEL OJ column, using 40:60:0.1 heptanes/2-propanol/diethylamine as the eluent) to give the (+)-enantiomer $[[α]^{25}_D+42.0°$ (c 0.067, CDCl$_3$)] (49 mg) and the (−)-enantiomer $[[α]^{25}_D-48.0°$ (c 0.067, CDCl$_3$)] (46 mg).

Step F: To a solution of single enantiomer freebase in methanol was added L-tartaric acid, followed by water. The resultant solution was lypholized to give the corresponding tartrate salt. (+)-8-([1,2,4]triazolo[1,5-a]pyridin-6-yl)-5-(3,5-difluorophenoxy)-2,3,4,5-tetrahydro-1H-benzo[c]azepine, L-tartrate [AUC HPLC 99%, Chiralcel OJ 99%] as a white solid: $^1$H NMR (500 MHz, CD$_3$OD) δ 9.12 (s, 1H), 8.45 (s, 1H), 8.04 (d, J=9.0 Hz, 1H), 7.87 (d, J=9.0 Hz, 1H), 7.82-7.79 (m, 2H), 7.67 (d, J=7.5 Hz, 1H), 6.76 (dd, J=7.5, 1.5 Hz, 1H), 6.55 (t, J=7.5 Hz, 1H), 5.83 (d, J=7.0 Hz, 1H), 4.75 (d, J=14.5 Hz, 1H), 4.50 (d, J=14.5 Hz, 1H), 4.40 (s, 2.2H), 3.83 (t, J=10.0 Hz, 1H), 3.64-3.57 (m, 1H), 2.57-2.32 (m, 2H); ESI MS m/z 393 [M+H]$^+$. (−)-8-([1,2,4]triazolo[1,5-a]pyridin-6-yl)-5-(3,5-difluorophenoxy)-2,3,4,5-tetrahydro-1H-benzo[c]azepine, L-tartrate [AUC HPLC 99%, Chiralcel OJ 99%] as a white solid: $^1$H NMR (500 MHz, CD$_3$OD) δ 9.12 (s, 1H), 8.45 (s, 1H), 8.04 (d, J=9.0 Hz, 1H), 7.87 (d, J=9.0 Hz, 1H), 7.82-7.79 (m, 2H), 7.67 (d, J=7.5 Hz, 1H), 6.76 (dd, J=7.5, 1.5 Hz, 1H), 6.55 (t, J=7.5 Hz, 1H), 5.83 (d, J=7.0 Hz, 1H), 4.75 (d, J=14.5 Hz, 1H), 4.50 (d, J=14.5 Hz, 1H), 4.40 (s, 2.2H), 3.83 (t, J=10.0 Hz, 1H), 3.64-3.57 (m, 1H), 2.57-2.32 (m, 2H); ESI MS m/z 393 [M+H]$^+$.

Example 38

Preparation of (+/−) 8-(6-(difluoromethoxy)pyridazin-3-yl)-5-(3,5-difluorophenoxy)-2,3,4,5-tetrahydro-1H-benzo[c]azepine, tartrate salt Step A: A mixture of the boronate ester (0.45 g, 0.76 mmol, partially pure) from step C of Example 37, 3-chloro-6-(difluoromethoxy)pyridazine (0.16 g, 0.91 mmol), and cesium carbonate (0.74 g, 2.3 mmol) in a solution of DMF (8 mL) and water (2 mL) was purged with argon for about 10 minutes. 1,1'-Bis(diphenylphosphino)ferrocenedichloropalladium (56 mg, 0.076 mmol) was added to the mixture, which was then heated at 80° C. for 2 hours. After cooling to room temperature, the reaction mixture was diluted with dichloromethane, washed with water and brine, dried over sodium sulfate, filtered, and concentrated in vacuo. The residue obtained was purified by FCC (hexanes/ethyl acetate 95:5 to 45:55) to give the protected benzazepine (0.29 g, partially pure), which was used in the next step without further purification.

Step B: To a solution of the protected benzazepine (0.29 g, partially pure) from step A above in a mixture of dichloromethane (3 mL) and ethanol (8 mL) were added potassium carbonate (0.30 g, 2.1 mmol) and thiophenol (0.15 mL, 1.5 mmol). The reaction mixture was stirred at room temperature for 20 hours and then it was quenched with aqueous sodium bicarbonate, extracted with a 3:1 mixture of chloroform and IPA. The combined organic extract was dried over sodium sulfate and concentrated in vacuo. The crude product obtained was purified by preparative thin layer chromatography (dichloromethane/methanol/concentrated ammonium hydroxide 90:9:1) to give the racemic benzazepine (127 mg, 40%) as a yellow foam:

$^1$H NMR (CDCl$_3$, 500 MHz) δ 7.92 (d, J=9.0 Hz, 1H), 7.89 (d, J=2.0 Hz, 1H), 7.81 (dd, J=8.0, 2.0 Hz, 1H), 7.75 (t, J=72.0 Hz, 1H), 7.47 (dd, J=8.0, 1.5 Hz, 1H), 7.21 (d, J=9.0 Hz, 1H), 6.47-6.39 (m, 3H), 5.49 (d, J=10.5 Hz, 1H), 4.25 (d, J=15.0 Hz, 1H), 4.02 (d, J=15.0 Hz, 1H), 3.55-3.51 (m, 1H), 3.30-3.25 (m, 1H), 2.30-2.04 (m, 2H).

To a solution of this freebase in methanol was added L-tartaric acid, followed by water. The resultant solution was lypholized to give (+/−)-8-(6-(difluoromethoxy)pyridazin-3-yl)-5-(3,5-difluorophenoxy)-2,3,4,5-tetrahydro-1H-benzo[c]azepine, tartrate salt [AUC HPLC 95.4%] as an off-white solid: $^1$H NMR (CD$_3$OD, 500 MHz) δ 8.25 (d, J=9.5 Hz, 1H), 8.13 (s, 1H), 8.05 (d, J=7.5 Hz, 1H), 7.76 (t, J=71.5 Hz, 1H), 7.69 (d, J=8.0 Hz, 1H), 7.48 (d, J=9.0 Hz, 1H), 6.74 (d, J=7.5 Hz, 2H), 6.55 (t, J=9.0 Hz, 1H), 5.84 (d, J=7.0 Hz, 1H), 4.74 (d, J=15.0 Hz, 1H), 4.49 (d, J=15.0 Hz, 1H), 4.40 (s, 2.3H), 3.84-3.75 (m, 1H), 3.65-3.56 (m, 1H), 2.54-2.35 (m, 2H); ESI MS m/z 420 [M+H]$^+$.

Example 39

Preparation of (+/−)-2-(5-(3,5-difluorophenoxy)-2-methyl-2,3,4,5-tetrahydro-1H-benzo[c]azepin-8-yl) pyridazin-3(2H)-one and (+1H)-2-(5-(3,5-difluorophenoxy)-2,3,4,5-tetrahydro-1H-benzo[c]azepin-8-yl)pyridazin-3(2H)-one, tartrate salt Step A: To a solution of the bromide (0.3 g, 0.8 mmol, partially pure) from Step A in Example 36 in 1,4-dioxane (1 mL) were added pyridazin-3(2H)-one (94 mg, 0.98 mmol), N,N'-dimethylethylenediamine (35 μL, 0.33 mmol), and potassium phosphate (0.35 g, 1.63 mmol). The mixture was purged with argon, and copper (I) iodide (31 mg, 0.16 mmol) was added to it. The reaction was heated at 110° C. for 16 hours. After cooling to room temperature, the reaction mixture was diluted with dichloromethane, washed with water and brine, dried over sodium sulfate, filtered, and concentrated to give the crude product. Purification by reverse phase semi-preparative HPLC (5% B to 50% B over 35 min; A=95:5 water/acetonitrile+0.05% TFA, B=95:5 acetonitrile/water+ 0.05% TFA), and conversion into the corresponding free base using 2N sodium carbonate gave the coupled product 245-(3, 5-difluorophenoxy)-2-methyl-2,3,4,5-tetrahydro-1H-benzo[c]azepin-8-yl)pyridazin-3(2H)-one (202 mg, 64%) as a pale yellow foam: $^1$H NMR (CDCl$_3$, 500 MHz) δ 7.89 (dd, J=3.8, 1.7 Hz, 1H), 7.51-7.48 (m, 2H), 7.40 (d, J=8.2 Hz, 1H), 7.27-7.22 (m, 2H), 7.05-7.03 (m, 1H), 6.46-6.40 (m, 3H), 5.38 (dd, J=9.2, 1.1 Hz, 1H), 4.05-3.79 (m, 2H), 3.37-3.26 (m, 1H), 3.10-2.95 (m, 1H), 2.32 (s, 3H), 2.26-2.05 m, 2H).

Step B: To an ice-cold solution of the benzazepine (0.14 g, 0.15 mmol) from step A and 1,8-bis(dimethylamino)naphthalene (Proton-Sponge, 0.23 g, 1.07 mmol) in 1,2-dichloroethane (4.2 mL) was added 1-chloroethyl chloroformate (0.19 mL, 1.78 mmol) dropwise. The reaction mixture was stirred at 0° C. for 3 hours, and then washed with 1N hydrochloric acid. The organic layer was separated, and the aqueous layer was washed with dichloromethane. The combined organic extract was dried over magnesium sulfate, filtered and concentrated under reduced pressure, and methanol (4.2 mL) was added to the residue. The solution was heated under reflux for 2 hours, and concentrated under reduced pressure. Purification by preparative thin layer chromatography (90:9:1 dichloromethane/methanol/concentrated ammonium hydroxide) gave partially pure material. Re-purification by preparative thin layer:chromatography (95:4.5:0.5 dichloromethane/methanol/concentrated ammonium hydroxide), followed by reverse phase semi-preparative HPLC (30% B to 50% B; A=95:5 water/acetonitrile+0.05% TFA, B=95:5 acetonitrile/water+0.05% TFA), and conversion into the corresponding free base using 2N sodium carbonate gave the N-desmethyl product (23 mg, 17%): $^1$H NMR (300 MHz, CDCl$_3$) δ 8.04-8.01 (m, 1H), 7.52-7.42 (m, 4H), 7.09-7.05 (m, 1H), 6.67-6.63 (m, 2H), 6.55-6.40 (m, 1H), 5.70-5.60 (m, 1H), 4.20-4.05 (m, 1H), 4.05-6.90 (m, 1H), 3.50-3.20 (m, 2H), 2.20-2.05 (m, 2H).

To a solution of the N-desmethyl derivative (21 mg, 0.06 mmol) in methanol (1 mL) was added L-tartaric acid (9 mg, 0.06 mmol), followed by water (5 mL). The resultant solution was lyophilized overnight to give (+/−)-2-(5-(3,5-difluorophenoxy)-2,3,4,5-tetrahydro-1H-benzo[c]azepin-8-yl)pyridazin-3(2H)-one, tartrate salt (30 mg, >99%, AUC HPLC 97.1%) as an off-white solid: $^1$H NMR (CD$_3$OD, 500 MHz) δ 8.04 (dd, J=3.8, 1.6 Hz, 1H), 7.69 (d, J=1.4 Hz, 1H), 7.65-7.64 (m, 2H), 7.48 (dd, J=9.5, 3.8 Hz, 1H), 7.09 (dd, J=9.5, 1.6 Hz, 1H), 6.73 (dd, J=9.0, 2.2 Hz, 2H), 6.58-6.47 (m, 1H), 5.84-5.73 (m, 1H), 5.73-5.58 (m, 1H), 4.41-4.39 (m, 1H), 4.39 (s, 2H), 3.84-3.68 (m, 1H), 3.58-3.47 (m, 1H), 2.53-2.21 (m, 2H); ESI MS m/z 370 [M+H]$^+$.

Example 40

Preparation of (+)- and (−)-8-([1,2,4]triazolo[4,3-a]pyridin-6-yl)-5-(3,5-difluorophenoxy)-2-methyl-2,3,4,5-tetrahydro-1H-benzo[c]azepine, tartrate salt Step A: To a mixture of the bromide (1.21 g, 3.29 mmol, partially pure) from step A in Example 36, potassium acetate (0.97 g, 9.86 mmol) and bis(pinacolato)diboron (0.92 g, 3.62 mmol) was added DMSO (21 mL). The mixture was purged with argon for about 10 minutes, and 1,1'-bis(diphenylphosphino)ferrocenedichloropalladium (81 mg, 0.10 mmol) was added to it. The reaction was heated at 80° C. for 3 hours. After cooling to room temperature, the reaction mixture was partitioned between water and dichloromethane. The aqueous layer was separated, and re-extracted with dichloromethane (2×). The combined organic extract was washed with 1:1 water/brine, dried over sodium sulfate, filtered and concentrated to give the desired boronate ester (1.24 g, crude) as a black oil which was used in the next step without purification.

Step B: To mixture of the boronate ester (0.3 g, crude) from step A above, 6-bromo-[1,2,4]triazolo[4,3-a]pyridine (0.32 g, 1.64 mmol), and cesium carbonate (0.80 g, 2.47 mmol) in a solution of DMF (5 mL) and water (1.25 mL) was purged with argon for about 10 minutes. 1,1'-Bis(diphenylphosphino)ferrocenedichloropalladium (40 mg, 0.05 mmol) was added to the mixture, which was then heated at 80° C. for 4 hours. After cooling to room temperature, the reaction mixture was diluted with dichloromethane, washed with water and brine, dried over magnesium sulfate, filtered and concentrated. The residue obtained was purified by reverse phase semi-preparative HPLC (5% B to 50% B over 50 min; A=95:5 water/acetonitrile+0.05% TFA, B=95:5 acetonitrile/water+0.05% TFA), and converted into the corresponding free base using 2N sodium carbonate to give the coupled product (70 mg, 20%) as a brown foam, which was resolved by preparative chiral HPLC(CHIRALPAK AD column, using 80:20:0.1 heptanes/isopropanol/diethylamine as the eluent) to give enantiomer A and enantiomer B. Enantiomer A was subjected to flash column chromatography (dichloromethane, then 95:4.5:0.5 to 90:9:1 dichloromethane/methanol/concentrated ammonium hydroxide) to remove traces of diethylamine. Enantiomer B was subjected to further chiral purification (CHIRALCEL OD column, using 80:20:0.1 heptanes/ethanol/diethylamine as the eluent), followed by flash column chromatography (dichloromethane, then 95:4.5:0.5 to 90:9:1 dichloromethane/methanol/concentrated ammonium hydroxide).

To a solution of enantiomer A (23 mg, 0.05 mmol) in methanol (0.5 mL) was added L-tartaric acid (8 mg, 0.05 mmol) followed by water (4 mL). The resultant solution was lyophilized overnight to give (+)-8-([1,2,4]triazolo[4,3-a]pyridin-6-yl)-5-(3,5-difluorophenoxy)-2-methyl-2,3,4,5-tetrahydro-1H-benzo[c]azepine, tartrate salt (30 mg, 95%, AUC HPLC 99%) as an off-white solid:
[[α]$^{25}_D$+44.3° (c 0.09, CD$_3$OD)]; $^1$H NMR (CD$_3$OD, 500 MHz) δ 9.22 (s, 1H), 8.81 (s, 1H), 7.86-7.80 (m, 2H), 7.77-7.74 (m, 2H), 7.64 (d, J=8.1 Hz, 1H), 6.74 (dd, J=9.0, 2.0 Hz, 2H), 6.57-6.53 (m, 1H), 5.77 (d, J=7.6 Hz, 1H), 4.76-4.63 (m, 1H), 4.42 (s, 2H), 4.43-4.30 (m, 1H), 3.89-3.74 (m, 1H), 3.58-3.47 (m, 1H), 2.83 (s, 3H), 2.58-2.31 (m, 2H); ESI MS m/z 407 [M+H]$^+$.

To a solution of enantiomer B (24 mg, 0.06 mmol) in methanol (0.5 mL) was added L-tartaric acid (9 mg, 0.06 mmol) followed by water (4 mL). The resultant solution was lyophilized overnight to give the correspondent tartrate salt of (−)-enantiomer (32 mg, >99%, AUC HPLC>99%) as an off-white solid: [[α]$^{25}_D$-54.5° (c 0.11, CD$_3$OD)]; ESI MS m/z 407 [M+H]$^+$.

Example 41

Preparation of (+)- and (−)-8-(6-(difluoromethoxy)pyridazin-3-yl)-5-(3,5-difluorophenoxy)-2-methyl-2,3,4,5-tetrahydro-1H-benzo[c]azepine, tartrate salt Step A: To mixture of the boronate ester (0.3 g, crude) from step A in Example 40, 3-chloro-6-(difluoromethoxy)pyridazine (0.17 g, 0.94 mmol), and cesium carbonate (0.80 g, 2.47 mmol) in a solution of DMF (5 mL) and water (1.25 mL) was purged with argon for about 10 minutes. 1,1'-Bis(diphenylphosphino)ferrocenedichloropalladium (40 mg, 0.05 mmol) was added to the mixture, which was then heated at 80° C. for 2 hours. After cooling to room temperature, the reaction mixture was diluted with dichloromethane, washed with water and brine, dried over magnesium sulfate, filtered, and concentrated. The residue obtained was purified by reverse phase semi-preparative HPLC (5% B to 50% B over 50 min; A=95:5 water/acetonitrile+0.05% TFA, B=95:5 acetonitrile/water+0.05% TFA), and converted into the corresponding free base using 2N sodium carbonate to give the coupled product (114 mg, 32%), which was resolved by preparative chiral HPLC(CHIRALPAK AD column, using 80:20:0.1 heptanes/isopropanol/diethylamine as the eluent) to give enantiomer A and enantiomer B. Enantiomer A was subjected to flash column chromatography (dichloromethane, then 99:0.9:0.1 to 90:9:1 dichloromethane/methanol/concentrated ammonium hydroxide) to remove traces of diethylamine. Enantiomer B was subjected to further chiral purification (CHIRALCEL OD column, using 80:20:0.1 heptanes/ethanol/diethylamine as the eluent), followed by flash column chromatography (dichloromethane, then 99:0.9:0.1 to 90:9:1 dichloromethane/methanol/concentrated ammonium hydroxide).

To a solution of enantiomer A (18 mg, 0.04 mmol) in methanol (0.5 mL) was added L-tartaric acid (6 mg, 0.04 mmol) followed by water (4 mL). The resultant solution was lyophilized overnight to give (+)-8-(6-(difluoromethoxy)pyridazin-3-yl)-5-(3,5-difluorophenoxy)-2-methyl-2,3,4,5-tetrahydro-1H-benzo[c]azepine (Enantimer A), tartrate salt (24 mg, >99%, AUC HPLC>99%) as an off-white solid: $[[\alpha]^{25}_D+53.1°$ (c 0.10, $CD_3OD$)]; $^1H$ NMR ($CD_3OD$, 500 MHz) δ 8.26 (d, J=9.2 Hz, 1H), 8.10 (d, J=1.7 Hz, 1H), 8.04 (dd, J=7.8, 1.8 Hz, 1H), 7.76 (t, J=71.9 Hz, 1H), 7.65 (d, J=8.0 Hz, 1H), 7.48 (d, J=9.2 Hz, 1H), 6.73 (dd, J=9.0, 2.0 Hz, 2H), 6.56-6.52 (m, 1H), 5.78 (d, J=8.8 Hz, 1H), 4.74-4.58 (m, 1H), 4.43-4.39 (m, 1H), 4.41 (s, 2H), 3.84-3.68 (m, 1H), 3.53-3.37 (m, 1H), 2.79 (s, 3H), 2.53-2.26 (m, 2H); ESI MS m/z 434 $[M+H]^+$.

To a solution of enantiomer B (34 mg, 0.08 mmol) in methanol (0.5 mL) was added L-tartaric acid (12 mg, 0.08 mmol) followed by water (4 mL). The resultant solution was lyophilized overnight to give the correspondent tartrate salt of (−)-enantiomer (46 mg, >99%, AUC HPLC>99%) as a white solid: $[[\alpha]^{25}_D-60.0°$ (c 0.08, $CD_3OD$)]; ESI MS m/z 434 $[M+H]^+$.

Example 42

Preparation of (+)- and (−)-6-(5-(3,5-difluorophenoxy)-2-methyl-2,3,4,5-tetrahydro-1H-benzo[c]azepin-8-yl)pyridazin-3-amine, tartrate salt Step A: To mixture of the boronate ester (0.3 g, crude) from step A in Example 40, 6-chloropyridazin-3-amine (0.21 g, 1.64 mmol), and cesium carbonate (0.80 g, 2.47 mmol) in a solution of DMF (5 mL) and water (1.25 mL) was purged with argon for about 10 minutes. 1,1'-Bis(diphenylphosphino)ferrocenedichloropalladium (40 mg, 0.06 mmol) was added to the mixture, which was then heated at 80° C. for 2 hours. After cooling to room temperature, the reaction mixture was diluted with dichloromethane, washed with water and brine, dried over magnesium sulfate, filtered, and concentrated. The residue obtained was purified by reverse phase semi-preparative HPLC (5% B to 50% B over 50 minutes; A=95:5 water/acetonitrile+0.05% TFA, B=95:5 acetonitrile/water+0.05% TFA), and converted into the corresponding free base using 2N sodium carbonate to give the coupled product (99 mg, 32%) as a white foam, which was resolved by preparative chiral HPLC(CHIRALCEL OD column, using 90:10:0.1 heptanes/ethanol/diethylamine as the eluent) to give enantiomer A and enantiomer B.

To a solution of enantiomer A (30 mg, 0.08 mmol) in methanol (1 mL) was added L-tartaric acid (12 mg, 0.08 mmol) followed by water (5 mL). The resultant solution was lyophilized overnight to give (+)-6-(5-(3,5-difluorophenoxy)-2-methyl-2,3,4,5-tetrahydro-1H-benzo[c]azepin-8-yl)pyridazin-3-amine, tartrate salt (41 mg, 99%, AUC HPLC>99%) as an off-white solid: $[[\alpha]^{25}_D+133.3°$ (c 0.07, methanol)]; $^1H$ NMR ($CD_3OD$, 500 MHz) δ 8.08 (s, 1H), 7.91 (dd, J=7.9, 1.6 Hz, 1H), 7.82 (d, J=9.3 Hz, 1H), 7.59 (d, J=7.9 Hz, 1H), 7.02 (d, J=9.3 Hz, 1H), 6.75-6.71 (m, 2H), 6.55-6.51 (m, 1H), 5.75 (d, J=7.7 Hz, 1H), 4.83-4.80 (m, 1H), 4.44-4.40 (m, 1H), 4.41 (s, 2H), 3.90-2.75 (m, 1H), 3.70-3.55 (m, 1H), 2.87 (s, 3H), 2.55-2.30 (m, 2H); ESI MS m/z 383 $[M+H]^+$.

To a solution of enantiomer B (29 mg, 0.08 mmol) in methanol (1 mL) was added L-tartaric acid (11 mg, 0.08 mmol) followed by water (5 mL). The resultant solution was lyophilized overnight to give the correspondent tartrate salt of (−)-enantiomer (40 mg, >99%, AUC HPLC>99%) as an off-white solid: $[[\alpha]^{25}_D-45.2°$ (c 0.10, methanol)]; ESI MS m/z 383 $[M+H]^+$.

Example 43

Preparation of (+)- and (−)-2-(5-(3,5-difluorophenoxy)-2-methyl-2,3,4,5-tetrahydro-1H-benzo[c]azepin-8-yl)-[1,2,4]triazolo[4,3-a]pyridin-3(2H)-one, tartrate salt Step A: To a solution of the bromide (0.3 g, 0.8 mmol, partially pure) from Step A in Example 36 in 1,4-dioxane (1 mL) were added [1,2,4]triazolo[4,3-a]pyridin-3(2H)-one (0.13 g, 0.98 mmol), N,N'-dimethylethylenediamine (35 μL, 0.33 mmol), and potassium phosphate (0.35 g, 1.63 mmol). The mixture was purged with argon, and copper (I) iodide (31 mg, 0.16 mmol) was added to it. The reaction was heated at 110° C. for 16 hours. After cooling to room temperature, the reaction mixture was diluted with dichloromethane, washed with water and brine, dried over sodium sulfate, filtered and concentrated to give the crude product. Purification by reverse phase semi-preparative HPLC (5% B to 50% B over 35 minutes; A=95:5 water/acetonitrile+0.05% TFA, B=95:5 acetonitrile/water+0.05% TFA), and conversion into the corresponding free base using 2N sodium carbonate gave the coupled product (158 mg, 46%) as a yellow foam, which was resolved by preparative chiral HPLC(CHIRALCEL OJ column, using 60:40:0.1 heptanes/ethanol/diethylamine as the eluent) to give enantiomer A and enantiomer B.

To a solution of enantiomer A (65 mg, 0.15 mmol) in methanol (1 mL) was added L-tartaric acid (23 mg, 0.15 mmol) followed by water (5 mL). The resultant solution was lyophilized overnight to give 2-(5-(3,5-difluorophenoxy)-2-methyl-2,3,4,5-tetrahydro-1H-benzo[c]azepin-8-yl)-[1,2,4]triazolo[4,3-a]pyridin-3(21)-one (Enantiomer A), tartrate salt (86 mg, 98%, AUC HPLC 97.9%) as an off-white solid: $^1H$ NMR ($CD_3OD$, 500 MHz) δ 8.20 (d, J=2.0 Hz, 1H), 8.14 (dd, J=8.4, 2.1 Hz, 1H), 7.88 (d, J=7.1 Hz, 1H), 7.62 (d, J=8.4 Hz, 1H), 7.30 (dd, J=6.4, 1.1 Hz, 1H), 7.23 (d, J=9.5 Hz, 1H), 6.74 (dd, J=8.9, 1.9 Hz, 2H), 6.70-6.65 (m, 1H), 6.56-6.52 (m, 1H), 5.74-5.72 (m, 1H), 4.80-4.63 (m, 1H), 4.43-4.26 (m, 1H), 4.42 (s, 2H), 3.89-3.63 (m, 1H), 3.52-3.37 (m, 1H), 2.83 (s, 3H), 2.47-2.26 (m, 2H); ESI MS m/z 423 $[M+H]^+$. Anal. Calcd. for $C_{23}H_{20}F_2N_4O_2.1.1C_4H_6O_6.0.75H_2O$: C, 54.75; H, 4.71; N, 9.32. Found: C, 54.70; H, 4.68; N, 9.03.

To a solution of enantiomer B (60 mg, 0.14 mmol) in methanol (1 mL) was added L-tartaric acid (21 mg, 0.14 mmol) followed by water (5 mL). The resultant solution was lyophilized overnight to give the correspondent tartrate salt of Enantiomer B (80 mg, 98%, AUC HPLC 98.5%) as an off-white solid; ESI MS m/z 423 $[M+H]^+$. Anal. Calcd. for $C_{23}H_{20}F_2N_4O_2.1.1C_4H_6O_6.0.25H_2O$: C, 55.59; H, 4.61; N, 9.46. Found: C, 55.48; H, 4.48; N, 9.31.

Example 44

Preparation of 1-(5-(3,5-difluorophenoxy)-2-methyl-2,3,4,5-tetrahydro-1H-benzo[c]azepin-8-yl)pyridin-2(1H)-one (Enantiomer A), tartrate salt and the tartrate salt of Enantiomer B Step A: To a solution of the bromide (0.3 g, 0.8 mmol, partially pure) from Step A in Example 36 in 1,4-dioxane (1 mL) were added 2-hydroxypyridine (93 mg, 0.98 mmol), N,N'-dimethylethylenediamine (35 µL, 0.33 mmol) and potassium phosphate (0.35 g, 1.63 mmol). The mixture was purged with argon, and copper (I) iodide (31 mg, 0.16 mmol) was added to it. The reaction was heated at 110° C. for 16 hours. After cooling to room temperature, the reaction mixture was diluted with dichloromethane, washed with water and brine, dried over sodium sulfate, filtered and concentrated to give the crude product. Purification by reverse phase semi-preparative HPLC (5% B to 50% B over 35 minutes; A=95:5 water/acetonitrile+0.05% TFA, B=95:5 acetonitrile/water+0.05% TFA), and conversion into the corresponding free base using 2N sodium carbonate gave the coupled product (103 mg, 33%) as a pale yellow foam, which was resolved by preparative chiral HPLC (CHIRALCEL OJ column, using 80:20:0.1 heptanes/ethanol/diethylamine as the eluent) to give enantiomer A and enantiomer B.

To a solution of enantiomer A (40 mg, 0.1 mmol) in methanol (1 mL) was added L-tartaric acid (16 mg, 0.1 mmol) followed by water (5 mL). The resultant solution was lyophilized overnight to give 1-(5-(3,5-difluorophenoxy)-2-methyl-2,3,4,5-tetrahydro-1H-benzo[c]azepin-8-yl)pyridin-2 (1H)-one (Enantiomer A), (55 mg, 99%, AUC HPLC>99%) as an off-white solid: $^1$H NMR (CD$_3$OD, 500 MHz) δ 7.65-7.60 (m, 3H), 7.48 (d, J=2.1 Hz, 1H), 7.44 (d, J=8.1 Hz, 1H), 6.73 (dd, J=9.0, 1.9 Hz, 2H), 6.64 (d, J=9.1 Hz, 1H), 6.58-6.42 (m, 2H), 5.78 (d, J=8.6 Hz, 1H), 4.68-4.47 (m, 1H), 4.41 (s, 2H), 4.37-4.16 (m, 1H), 3.79-3.58 (m, 1H), 3.47-3.37 (m, 1H), 2.76 (s, 3H), 2.47-2.26 (m, 2H); ESI MS m/z 383 [M+H]$^+$. Anal. Calcd. for C$_{22}$H$_{20}$F$_2$N$_2$O$_2$.1.1C$_4$H$_6$O$_6$.0.25H$_2$O: C, 57.44; H, 4.95; N, 5.07. Found: C, 57.36; H, 5.05; N, 4.94.

To a solution of enantiomer B (32 mg, 0.08 mmol) in methanol (1 mL) was added L-tartaric acid (12 mg, 0.08 mmol) followed by water (5 mL). The resultant solution was lyophilized overnight to give the correspondent tartrate salt of Enantiomer B (44 mg, 98%, AUC HPLC 98.6%) as an off-white solid: ESI MS m/z 383 [M+H]$^+$. Anal. Calcd. for C$_{22}$H$_{20}$F$_2$N$_2$O$_2$.1.1C$_4$H$_6$O$_6$: C, 58.64; H, 4.92; N, 5.26. Found: C, 58.70; H, 5.12; N, 5.23.

Example 45

Preparation of (+)- and (−)-4-(2-methyl-5-phenoxy-2,3,4,5-tetrahydro-1H-benzo[c]azepin-8-yl)banzamide, tartrate salt The two enantiomers in Example 45 were prepared from the boronate ester from Step F in Example 16 and 4-bromobenzamide following the procedures of Step G, H, I and J in Example 16. (+)-4-(2-Methyl-5-phenoxy-2,3,4,5-tetrahydro-1H-benzo[c]azepin-8-yl)banzamide, tartrate salt (AUC HPLC 98.9%) is a white solid: mp 106-108° C.; $^1$H NMR (CD$_3$OD, 500 MHz)

δ 9.11 (s, 1H), 8.44 (s, 1H), 8.03 (d, J=9.3 Hz, 1H), 7.87 (79.11 (s, 1H), 8.44 (s, 1H), 8.03 (d, J=9.3 Hz, 1H), 7.87 (d, J=10.2 Hz, 1H), 7.80-7.78 (m, 2H), 7.63 (d, J=7.9 Hz, 1H), 7.26 (t, J=8.5 Hz, 2H), 7.06 (d, J=8.0 Hz, 2H), 6.95 (t, J=7.3 Hz, 1H), 5.74 (d, J=7.3 Hz, 1H), 4.92-4.84 (m, 1H), 4.54-4.50 (m, 1H), 4.42 (s, 3H), 3.93-3.90 (m, 1H), 3.60-3.54 (m, 1H), 2.91 (s, 1H), 2.49 2.38 (m 2H); ESI MS m/z 373 [M+H]. (+4-(2-methyl-5-phenoxy-2,3,4,5-tetrahydro-1H-benzo[c] azepin-8-yl)banzamide, tartrate salt (AUC HPLC 98.9%) is a white solid: mp 118-120° C.; ESI MS m/z 373 [M+H].

Example 46

Preparation of (+)- and (−)-2-Methyl-8-(4-methylsulfonylphenyl)-5-phenoxy-2,3,4,5-tetrahydro-1H-benzo[c]azepine, tartrate salt and (−)-2-Methyl-8-(4-methylsulfonylphenyl)-5-phenoxy-2,3,4,5-tetrahydro-1H-benzo[c]azepine, tartrate salt The two enantiomers in Example 46 were prepared from the boronate ester from Step F in Example 16 and 1-chloromethylsulfonylbenzene following the procedures of Step G, H, I and J in Example 16. (+)-2-Methyl-8-(4-methylsulfonylphenyl)-5-phenoxy-2,3,4,5-tetrahydro-1H-benzo[c] azepine, tartrate salt (AUC HPLC 98.9%) is a white solid: mp 116-118° C.; $^1$H NMR (CD$_3$OD, 500 MHz) δ 8.03 (d, J=8.5 Hz, 2H), 7.90 (d, J=8.5 Hz, 2H), 7.76-7.72 (m, 2H), 7.61 (d, J=8.0 Hz, 1H), 7.28-7.24 (m, 2H), 7.04 (d, J=7.9 Hz, 2H), 6.94 (t, J=7.4 Hz, 1H), 5.71 (d, J=7.8 Hz, 1H), 4.91-4.80 (m, 1H), 4.44-4.40 (m, 3H), 3.90-3.85 (m, 1H), 3.58-3.54 (m, 1H), 3.15 (s, 3H), 2.85 (s, 3H), 2.45-2.36 (m 2H); ESI MS m/z 408 [M+H]. (+2-Methyl-8-(4-methylsulfonylphenyl)-5-phenoxy-2,3,4,5-tetrahydro-1H-benzo[c]azepine, tartrate salt (AUC HPLC 98.9%) is a white solid: mp 116-118° C.; ESI MS m/z 408 [M+H].

Example 47

Preparation of (+)- and (−)-5-(3,5-difluorophenoxy)-2-methyl-8-(4-(methylsulfonyl)phenyl)-2,3,4,5-tetrahydro-1H-benzo[c]azepine, tartrate salt Step A: A mixture of the bromide (0.2 g, partially pure) from Step A in Example 36, 4-(methylsulfonyl)phenylboronic acid (0.15 g, 0.76 mmol), and cesium carbonate (0.49 g, 1.52 mmol) in a solution of DMF (3 mL) and water (0.75 mL) was purged with argon for about 10 minutes. 1,1'-Bis(diphenylphosphino)ferrocenedichloropalladium (25 mg, 0.03 mmol) was added to the mixture, which was then heated at 80° C. for 4 hours. After cooling to room temperature, the reaction mixture was diluted with dichloromethane, washed with water and brine, dried over sodium sulfate, filtered and concentrated. The residue obtained was purified by preparative thin layer chromatography (90:10 chloroform/isopropanol) to give the desired aryloxybenzazepine (129 mg, 59%) as an off-white solid, which was resolved by preparative chiral HPLC(CHIRALCEL OD column, using 80:20:0.1 heptanes/ethanol/diethylamine as the eluent) to give enantiomer A and enantiomer B.

To a solution of enantiomer A (60 mg, 0.13 mmol) in methanol (1 mL) was added L-tartaric acid (20 mg, 0.13 mmol) followed by water (5 mL). The resultant solution was lyophilized overnight to give (−)-5-(3,5-difluorophenoxy)-2-methyl-8-(4-(methylsulfonyl)phenyl)-2,3,4,5-tetrahydro-1H-benzo[c]azepine, tartrate salt (80 mg, >99%, AUC HPLC 99%) as an off-white solid: [[α]$^{25}$$_D$-42.0° (c 0.07, CD$_3$OD)]; $^1$H NMR (CD$_3$OD, 500 MHz) δ 8.04 (d, J=8.5 Hz, 2H), 7.91 (d, J=8.5 Hz, 2H), 7.77-7.74 (m, 2H), 7.62 (d, J=7.7 Hz, 1H), 6.73 (dd, J=8.9, 2.0 Hz, 2H), 6.55 (t, J=9.9 Hz, 1H), 5.76 (d, J=7.2 Hz, 1H), 4.79-4.63 (m, 1H), 4.43-4.40 (m, 1H), 4.42 (s, 2H), 3.84-3.68 (m, 1H), 3.58-3.42 (m, 1H), 3.15 (s, 3H), 2.83 (s, 3H), 2.53-2.26 (m, 2H); ESI MS m/z 444 [M+H]$^+$. Anal. Calcd. for C$_{24}$H$_{23}$F$_2$NO$_3$S.1.1C$_4$H$_6$O$_6$.O$_2$O: C, 54.44; H, 5.08; N, 2.24. Found: C, 54.61; H, 4.88; N, 2.18.

To a solution of enantiomer B (62 mg, 0.14 mmol) in methanol (1 mL) was added L-tartaric acid (21 mg, 0.14 mmol) followed by water (5 mL). The resultant solution was lyophilized overnight to give the correspondent (+)-enantiomer, tartrate salt (81 mg, 97%, AUC HPLC>99%) as an off-white solid: [[α]$^{25}$$_D$+58.8° (c 0.09, CD$_3$OD)]; ESI MS m/z 444 [M+H]$^+$. Anal. Calcd. for C$_{24}$H$_{23}$F$_2$NO$_3$S.1.1C$_4$H$_6$O$_6$.0.5H$_2$O: C, 55.23; H, 4.99; N, 2.27. Found: C, 55.06; H, 4.95; N, 2.13.

Example 48

Preparation of (+)- and (−)-4-(5-(3,5-difluorophenoxy)-2-methyl-2,3,4,5-tetrahydro-1H-benzo[c]azepin-8-yl)benzonitrile, tartrate salt Step A: A mixture of the bromide (0.19 g, partially pure) from Step A in Example 36, 4-cyanophenylboronic acid (0.11 g, 0.78 mmol), and cesium carbonate (0.51 g, 1.56 mmol) in a solution of DMF (3 mL) and water (0.75 mL) was purged with argon for about 10 minutes. 1,1′-Bis(diphenylphosphino)ferrocenedichloropalladium (25 mg, 0.03 mmol) was added to the mixture, which was then heated at 80° C. for 4 hours. After cooling to room temperature, the reaction mixture was diluted with dichloromethane, washed with water and brine, dried over sodium sulfate, filtered and concentrated. The residue obtained was purified by preparative thin layer chromatography (90:10 chloroform/isopropanol) to give the desired aryloxybenzazepine (113 mg, 56%) as a brown solid, which was resolved by preparative chiral HPLC (CHIRALCEL OJ column, using 80:20:0.1 heptanes/isopropanol/diethylamine as the eluent) to give enantiomer A and enantiomer B.

To a solution of enantiomer A (50 mg, 0.13 mmol) in methanol (1 mL) was added L-tartaric acid (19 mg, 0.13 mmol) followed by water (5 mL). The resultant solution was lyophilized overnight to give (−)-4-(5-(3,5-difluorophenoxy)-2-methyl-2,3,4,5-tetrahydro-1H-benzo[c]azepin-8-yl)benzonitrile, tartrate salt (68 mg, 98%, AUC HPLC 97.3%) as an off-white solid: [[α]$^{25}$$_D$−39.6° (c 0.09, CD$_3$OD)]; $^1$H NMR (CD$_3$OD, 500 MHz) δ 7.85-7.80 (m, 4H), 7.75-7.73 (m, 2H), 7.61 (d, J=7.7 Hz, 1H), 6.74 (dd, J=9.0, 2.0 Hz, 2H), 6.56-6.53 (m, 1H), 5.76 (d, J=8.1 Hz, 1H), 4.80-4.58 (m, 1H), 4.43-4.39 (m, 1H), 4.42 (s, 2H), 3.89-3.74 (m, 1H), 3.58-3.37 (m, 1H), 2.83 (s, 3H), 2.53-2.21 (m, 2H); ESI MS m/z 391 [M+H]$^+$. Anal. Calcd. for C$_{24}$H$_{20}$F$_2$N$_2$O.1.2C$_4$H$_6$O$_6$.0.5H$_2$O: C, 59.69; H, 4.90; N, 4.83. Found: C, 59.62; H, 4.89; N, 4.85.

To a solution of enantiomer B (51 mg, 0.13 mmol) in methanol (1 mL) was added L-tartaric acid (20 mg, 0.13 mmol) followed by water (5 mL). The resultant solution was lyophilized overnight to give the correspondent (+)-enantiomer, tartrate salt (68 mg, 98%, AUC HPLC>99%) as an off-white solid:
[[α]$^{25}$$_D$+58.9° (c 0.09, CD$_3$OD)]; ESI MS m/z 391 [M+H]$^+$. Anal. Calcd. for C$_{24}$H$_{20}$F$_2$N$_2$O.1.1C$_4$H$_6$O$_6$.0.5H$_2$O: C, 60.42; H, 4.93; N, 4.96. Found: C, 60.45; H, 4.96; N, 4.72.

Example 49

Preparation of (−)-2-Methyl-5-phenoxy-8-(pyrimidin-2-yl)-2,3,4,5-tetrahydro-1H-benzo[c]azepine, tartrate salt This compound was prepared from the boronate ester from step F of Example 16 and 2-bromopyrimidine following the procedures of Step G, H, and J in Example 16. (−)-2-Methyl-5-phenoxy-8-(pyrimidin-2-yl)-1-2,3,4,5-tetrahydro-1H-benzo[c]azepine, tartrate salt (AUC HPLC 98.9%) is a white solid: [[α]$^{25}$$_D$−52.5° (c 0.04, MeOH)]; mp 108-110° C.; 1H NMR (CD3OD, 500 MHz) δ 8.85 (d, J=4.9 Hz, 2H), 8.45 (s, 1H), 8.41 (d, J=7.9 Hz, 1H), 7.62 (d, J=8.0 Hz, 1H), 7.38 (t, J=4.9 Hz, 1H), m, 2H), 7.28-7.24 (m, 2H), 7.05 (d, J=8.0 Hz, 2H), 6.95 (t, J=7.3 Hz, 1H), 5.73 (d, J=8.0 Hz, 1H), 4.90-4.84 (m, 1H), 4.52-4.48 (m, 1H), 4.41 (s, 3H), 3.88-3.84 (m, 1H), 3.58-3.54 (m, 1H), 2.88 (s, 3H), 2.55-2.35 (m, 2H); ESI MS m/z 332 [M+H].

Example 50

Preparation of (+)- and (−)-8-(6-aminopyridazin-3-yl)-2-methyl-5-phenoxy-2,3,4,5-tetrahydro-1H-benzo[c]azepine, tartrate salt The two enantiomers in Example 50 were prepared from the boronate ester from Step F in Example 16 and 6-chloropyridazin-3-amine following the procedures of Step G, H, I and J in Example 16. (+)-8-(6-Aminopyridazin-3-yl)-2-methyl-5-phenoxy-2,3,4,5-tetrahydro-1H-benzo[c]azepine, tartrate salt (AUC HPLC 97%) is a white solid: mp 102-104° C.; $^1$H NMR (CD$_3$OD, 500 MHz) δ 8.20 (s, 1H), 8.04 (s, 1H), 8.00 (d, J=8.0 Hz, 1H), 7.86 (s, 1H), 7.69 (d, J=8.0 Hz, 1H), 7.28-7.24 (m, 2H), 7.04 (d, J=8.0 Hz, 1H), 6.95 (t, J=7.4 Hz, 1H), 5.71 (d, J=7.8 Hz, 1H), 4.90-4.86 (m, 1H), 4.49-4.46 (m, 1H), 4.43 (s, 3H), 3.90-3.85 (m, 1H), 3.64-3.44 (m, 3H), 2.91 (s, 3H), 2.48-2.36 (m, 2H); ESI MS m/z 347 [M+H]. (−)-8-(6-aminopyridazin-3-yl)-2-methyl-5-phenoxy-2,3,4,5-tetrahydro-1H-benzo[c]azepine, tartrate salt (AUC HPLC 97%) is a white solid: mp 112-114° C.; ESI MS m/z 347 [M+H].

Example 51

Preparation of (−)-5-(2,3-difluorophenoxy)-2-methyl-8-(pyridazin-3-yl)-2,3,4,5-tetrahydro-1H-benzo[c]azepine, tartrate salt (+)-2-Methyl-8-(pyridazin-3-yl)-2,3,4,5-tetrahydro-1H-benzo[c]azepin-5-ol was obtained following the procedure of Step H in Example 1 from (+)-5-(tert-butyldimethylsilyloxy)-2-methyl-8-(pyridazin-3-yl)-2,3,4,5-tetrahydro-1H-benzo[c]azepine in Step G of Example 1. Ether formation between (+)-2-methyl-8-(pyridazin-3-yl)-2,3,4,5-tetrahydro-1H-benzo[c]azepin-5-ol and 2,3-difluorohenol using procedures similar to those in Step B and C of Example 10 gave (−)-5-(2,3-difluorophenoxy)-2-methyl-8-(pyridazin-3-yl)-2,3,4,5-tetrahydro-1H-benzo[c]azepine, tartrate salt (AUC HPLC>99%) as a white solid: mp 112-114° C.;
1H NMR (CD3OD, 500 MHz) δ 9.18 (d, J=5.0 Hz, 1H), 8.20-8.19 (m, 2H), 8.08 (d, J=8.0 Hz, 1H), 7.62-7.61 (m, 1H), 7.64-7.62 (d, J=7.9 Hz, 1H), 7.05-7.03 (m, 1H), 6.89-6.85 (m, 1H), 5.78 (,d, J=7.2 Hz, 1H), 4.98-4.94 (m, 1H), 4.54-4.48 (m, 1H), 4.42 (s, 3H), 3.98-3.92 (m, 1H), 3.63-3.58 (m, 1H), 2.90 (s, 3H), 2.64-2.44 (m, 2H); ESI MS m/z 368 [M+H].

Example 52

Preparation of (−)-5-(3-cyanophenoxy)-2-methyl-8-(pyridazin-3-yl)-2,3,4,5-tetrahydro-1H-benzo[c]azepine, tartrate salt (+)-2-Methyl-8-(pyridazin-3-yl)-2,3,4,5-tetrahydro-1H-benzo[c]azepin-5-ol was obtained following the procedure of Step H in Example 1 from (+)-5-(tert-butyldimethylsilyloxy)-2-methyl-8-(pyridazin-3-yl)-2,3,4,5-tetrahydro-1H-benzo[c]azepine in Step G of Example 1. Ether formation between (+)-2-methyl-8-(pyridazin-3-yl)-2,3,4,5-tetrahydro-1H-benzo[c]azepin-5-ol and 3-hydroxybenzonitrile using procedures similar to those in Step B and C of Example 10 gave (−)-5-(3-cyanophenoxy)-2-methyl-8-(pyridazin-3-yl)-2,3,4,5-tetrahydro-1H-benzo[c]azepine, tartrate salt (AUC HPLC>99%) as a white solid: mp 113-115° C.;

1H NMR (CD3OD, 500 MHz) δ 9.17 (d, J=4.9 Hz, 1H), 8.20-8.17 (m, 2H), 8.08 (d, J=7.9 Hz, 1H), 7.82-7.80 (m, 1H), 7.67 (d, J=8.0 Hz, 1H), 7.48-7.40 (m, 3H), 7.32 (d, J=7.5 hz, 1H), 5.84 (d, J=8.1 Hz, 1H), 4.79-4.74 (m, 1H), 4.45-4.40 (m, 3H), 3.85-3.75 (m, 1H), 3.56-3.50 (m, 1H), 2.80 (s, 3H), 2.44-2.38 (m, 2H); ESI MS m/z 357 [M+H].

Example 53

Preparation of (−)-5-(4-cyanophenoxy)-2-methyl-8-(pyridazin-3-yl)-2,3,4,5-tetrahydro-1H-benzo[c]azepine, tartrate salt (+)-2-Methyl-8-(pyridazin-3-yl)-2,3,4,5-tetrahydro-1H-benzo[c]azepin-5-ol was obtained following the procedure of Step H in Example 1 from (+)-5-(tert-butyldimethylsilyloxy)-2-methyl-8-(pyridazin-3-yl)-2,3,4,5-tetrahydro-1H-benzo[c]azepine in Step G of Example 1. Ether formation between (+)-2-methyl-8-(pyridazin-3-yl)-2,3,4,5-tetrahydro-1H-benzo[c]azepin-5-ol and 4-hydroxybenzonitrile using procedures similar to those in Step B and C of Example 10 gave (−)-5-(4-cyanophenoxy)-2-methyl-8-(pyridazin-3-yl)-2,3,4,5-tetrahydro-1H-benzo[c]azepine, tartrate salt (AUC HPLC>99%) as a white solid: mp 110-112° C.;

1H NMR (CD3OD, 500 MHz) δ 9.17 (d, J=4.9 Hz, 1H), 8.20-8.17 (m, 2H), 8.08 (d, J=7.9 Hz, 1H), 7.68-7.64 (m, 2H), 7.23 (d, J=8.8 Hz, 2H), 5.90 (d, J=8.8 Hz, 2H), 4.74-4.70 (m, 1H), 4.46-4.42 (m, 3H), 3.85-3.75 (m, 1H), 3.56-3.50 (m, 1H), 2.80 (s, 3H), 2.44-2.38 (m, 2H); ESI MS m/z 357 [M+H].

Example 54

Preparation of (−)-5-(2,5-difluorophenoxy)-2-methyl-8-(pyridazin-3-yl)-2,3,4,5-tetrahydro-1H-benzo[c]azepine, tartrate salt (+)-2-Methyl-8-(pyridazin-3-yl)-2,3,4,5-tetrahydro-1H-benzo[c]azepin-5-ol was obtained following the procedure of Step H in Example 1 from (+)-5-(tert-butyldimethylsilyloxy)-2-methyl-8-(pyridazin-3-yl)-2,3,4,5-tetrahydro-1H-benzo[c]azepine in Step G of Example 1. Ether formation between (+)-2-methyl-8-(pyridazin-3-yl)-2,3,4,5-tetrahydro-1H-benzo[c]azepin-5-ol and 2,5-difluorophenol using procedures similar to those in Step B and C of Example 10 gave (−)-5-(2,5-difluorophenoxy)-2-methyl-8-(pyridazin-3-yl)-2,3,4,5-tetrahydro-1H-benzo[c]azepine, tartrate salt (AUC HPLC>99%) as a white solid: mp 102-104° C.;

1H NMR (CD3OD, 500 MHz) δ 9.17 (d, J=5.0 Hz, 1H), 8.20-8.18 (m, 2H), 8.08 (d, J=8.0 Hz, 1H), 7.82-7.80 (m, 1H), 7.63 (d, J=8.0 Hz, 1H), 7.14-7.04 (m, 2H), 3.72-3.68 (m, 1H), 5.75 (d, J=7.5 Hz, 1H), 4.90-4.82 (m, 1H), 4.44-4.41 (m, 3H), 3.90-3.80 (m, 1H), 3.58-3.54 (m, 1H), 2.82 (s, 3H), 2.60-2.40 (m, 2H); ESI MS m/z 368 [M+H].

Example 55

Preparation of (+5-(2,6-difluorophenoxy)-2-methyl-8-(pyridazin-3-yl)-2,3,4,5-tetrahydro-1H-benzo[c]azepine, tartrate salt (+)-2-Methyl-8-(pyridazin-3-yl)-2,3,4,5-tetrahydro-1H-benzo[c]azepin-5-ol was obtained following the procedure of Step H in Example 1 from (+)-5-(tert-butyldimethylsilyloxy)-2-methyl-8-(pyridazin-3-yl)-2,3,4,5-tetrahydro-1H-benzo[c]azepine in Step G of Example 1. Ether formation between (+)-2-methyl-8-(pyridazin-3-yl)-2,3,4,5-tetrahydro-1H-benzo[c]azepin-5-ol and 2,6-difluorophenol using procedures similar to those in Step B and C of Example 10 gave (−)-5-(2,6-difluorophenoxy)-2-methyl-8-(pyridazin-3-yl)-2,3,4,5-tetrahydro-1H-benzo[c]azepine, tartrate salt (AUC HPLC>99%) as a white solid: mp 98-100° C.; 1H NMR (CD3OD, 500 MHz) δ 9.02-9.00 (m, 1H), 8.35-8.00 (m, 4H), 7.50-7.40 (m, 1H), 7.02-6.92 (m, 3H), 5.52-5.48 (m, 1H), 5.16-5.10 (M, 1H), 4.42 (S, 3H), 4.02-4.00 (M, 1H), 3.88-3.78 (M, 2H), 2.50 (S, 3H), 2.76-2.42 (m, 2H); ESI MS m/z 368 [M+H].

Example 56

Primary Binding Assay

Preparation of Membranes

Recombinant HEK-293 cells expressing either the hSERT, hDAT, or hNET proteins were harvested from T-175 flasks as follows. The medium was removed from the flasks and the cells rinsed with HBSS without Ca and without Mg. The cells were then incubated for 5-10 minutes in 10 mM Tris-Cl, pH 7.5, 5 mM EDTA before the cells were lifted with a combination of pipetting and scraping, as needed. The cell suspension was collected into centrifuge bottles and homogenized for 30 seconds with a Polytron homogenizer. The suspension was centrifuged for 30 minutes at 32,000×g, 4° C. The supernatant was decanted and the pellet resuspended and homogenized in 50 mM Tris-Cl, pH 7.5, 1 mM EDTA for 10 seconds. The suspension was then centrifuged again for 30 minutes at 32,000×g, 4° C. The supernatant was decanted and the pellet resuspended in 50 mM Tris-Cl, pH 7.5, 1 mM EDTA and briefly homogenized. A Bradford assay (Bio-rad) was performed and the membrane preparation diluted to 2 mg/ml with 50 mM Tris-Cl, pH 7.5, 1 mM EDTA. Aliquots were prepared, and then frozen and stored at −80° C.

SERT Radioligand Binding Assay

Compounds were dissolved in 100% DMSO at a concentration 100 times the desired highest assay concentration, serially diluted 1:3 in 100% DMSO, and 0.4 µl/well of each solution esd dispensed to a Nunc polypropylene, round bottom, 384-well plate. 100% inhibition is defined with 0.4 µl/well of 1 mM fluoxetine dissolved in DMSO. 20 µl/well of a 2× membrane preparation (15 ug/ml in 50 mM Tris-Cl, pH 7.5, 120 mM NaCl, 5 mM KCl) and 20 µl/well of a 2× radioligand solution (520 µM [$^{125}$I]RTI-55 in 50 mM Tris-Cl, pH 7.5, 120 mM NaCl, 5 mM KCl) were added to each well and the reaction incubated for 1 hour at room temperature. The contents of the assay plate were then transferred to a Millipore Multiscreen$_{HTS}$ GF/B filter plate which has been pretreated with 0.5% PEI for at least one hour. The plate was vacuum filtered and washed with 7 washes of 100 µl/well 50 mM Tris-Cl, pH 7.5, 120 mM NaCl, 5 mM KCl chilled to 4° C. The filtration and washing was completed in less than 90 seconds. The plates were air-dried overnight, 12 µl/well of MicroScint scintillation fluid added, and the plates counted in a Trilux.

DAT Radioligand Binding Assay

Compounds were dissolved in 100% DMSO at a concentration 100 times the desired highest assay concentration, serially diluted 1:3 in 100% DMSO, and 0.4 µl/well of each solution was dispensed to a Nunc polypropylene, round bottom, 384-well plate. 100% inhibition is defined with 0.4 µl/well of 1 mM GBR-12935 dissolved in DMSO. 20 ul/well of a 2× membrane preparation (12.5 µg/ml in 30 mM sodium phosphate buffer, pH 7.9 at 4° C.) and 20 µl/well of a 2× radioligand solution (250 µM [$^{125}$I]RTI-55 in 30 mM sodium phosphate buffer, pH 7.9 at 4° C.) were added to the well and the reaction incubated for 1 hour at room temperature. The contents of the assay plate were then transferred to a Millipore Multiscreen$_{HTS}$ GF/B filter plate which had been pretreated with 0.5% PEI for at least one hour. The plate was vacuum-filtered and washed with 7 washes of 100 μl/well 50 mM Tris-Cl, pH 7.5, 120 mM NaCl, 5 mM KCl chilled to 4° C. The filtration and washing were completed in less than 90 seconds. The plates were air-dried overnight, 12 μl/well of MicroScint scintillation fluid added, and the plates counted in a Trilux.

NET Radioligand Binding Assay

Compounds were dissolved in 100% DMSO at a concentration 100 times the desired highest assay concentration, serially diluted 1:3 in 100% DMSO, and 1.0 μl/well of each solution was dispensed to a Nunc polypropylene, round bottom, 384-well plate. 100% inhibition is defined with 1.0 μl/well of 10 mM desipramine dissolved in DMSO. 50 μl/well of a 2× membrane preparation (0.4 mg/ml in 50 mM Tris-Cl, pH 7.5, 120 mM NaCl, 5 mM KCl) and 50 μl/well of a 2× radioligand solution (4 nM [$^3$H]nisoxetine in 50 mM Tris-Cl, pH 7.5, 120 mM NaCl, 5 mM KCl) were added to the well and the reaction incubated for 1 hour at room temperature. The contents of the assay plate were then transferred to a Millipore Multiscreen$_{HTS}$ GF/B filter plate which had been pretreated with 0.5% PEI for at least one hour. The plate was vacuum filtered and washed with 7 washes of 100 μl/well 50 mM Tris-Cl, pH 7.5, 120 mM NaCl, 5 mM KCl chilled to 4° C. The filtration and washing is completed in less than 90 seconds. The plates were air-dried overnight, 12 μl/well of MicroScint scintillation fluid added, and the plates counted in a Trilux.

Data Analysis

The raw data is normalized to percent inhibition using control wells defining 0% (DMSO only) and 100% (selective inhibitor) inhibition which are run on each plate. Each plate is run in triplicate, and the concentration response curve thus generated is fit using the four-parameter dose response equation, Y=Bottom+(Top−Bottom)/(1+10^((Log IC$_{50}$−X)*Hill-Slope)) in order to determine the IC$_{50}$ value for each compound. The radioligand concentration chosen for each assay corresponds to the K$_d$ concentration determined through saturation binding analysis for each assay.

Example 57

Occupancy Assay

Male Sprague-Dawley (180-300 g) (Charles River Laboratories, Wilmington, Mass.) were orally dosed with a test compound (suspended in 0.25% methylcellulose in distilled water). After 60 minutes survival post-dose, rats were sacrificed, and the brains were evacuated and rapidly frozen in chilled isopentane. The frozen brain tissues were stored at −80° C. until use.

The brain tissues were thawed and homogenized in 7-10 volumes of incubation buffer using a polytron homogenizer (Kinematica, Littau-Lucerne, Switzerland). Sample aliquots were frozen immediately in dry ice/ethanol and stored at −80° C. Protein content was measured for each brain using a Coomassie protein assay kit (Pierce, Rockford, Ill.). In a 96 deep-well plate, 100 μg of tissue (0.4 mg/ml) was incubated with an appropriate radio ligand under conditions same as for the brain section binding as shown in Table 1 below. The effect of the incubation time and temperature on occupancy assessment was also evaluated. At the end of the incubation time, the reactions were stopped by filtering through FPXLR-196 filters (Brandel, Gaithersburg, Md.) that had been soaked in 0.5-1.0% polyethyleneimine for 1 hour at 4° C. The filters were washed twice with ice-cold incubation buffer, tritium was measured using a Wallac Microbeta liquid scintillation counter.

TABLE 1

Radioligands and Incubation Conditions for ex vivo Homogenate Binding Assay

| Transporter | Radioligand | Concentration | Nonspecific Drug | Buffer | Incubation time | Temp |
|---|---|---|---|---|---|---|
| SERT | [$^3$H]-citalopram | 2 nM | 10 uM Fluoxetine | 50 mM Tris, 120 mM NaCl, 5 mM KCl (pH 7.4 at 25° C.) | 20 minutes | 4° C. |
| DAT | [$^{125}$I]-RTI-55 | 0.4 nM | 10 uM GBR-12935 | 30 mM sodium phosphate (pH 7.9 at 4° C.) | 10 minutes | 4° C. |
| NET | [$^3$H]-nisoxetine | 5 nM | 10 uM Reboxetine | 50 mM Tris, 300 mM NaCl, 5 mM KCl (pH 7.4 at 25° C.) | 20 minutes | 4° C. |

The radioactivity of the filters was measured as disintegrations per minute on a LKB Trilux liquid scintillation counter or Packard Cobra II gamma counter. Specific binding was calculated by subtracting the value of nonspecific binding density from that of total binding density (non-drug treated tissue) in the corresponding region or tissue homogenate. The percent of specific binding was calculated as the following: percent specific binding=(specific binding in drug treated minus nonspecific binding)/(total binding minus nonspecific binding)×100%. The percentage of specific binding in a drug treated condition is inversely proportional to the percent inhibition or percent receptor occupancy by the drug.

Example 58 in vivo Behavioral Assays

For All Tests

All animals were maintained in accordance with the guidelines of the Committee on Animals of the Bristol-Myers Squibb Company and *Guide for Care and Use of Laboratory Animals*, Institute of Animal Laboratory Resources, 1996, which are hereby incorporated by reference in their entirety. Research protocols were approved by the Bristol-Myers Squibb Company Institutional Animal Care and Use Committee.

Mouse Tail Suspension Assay

Male Swiss Webster mice are housed 3-4 per cage in rooms maintained at a constant temperature (21-23° C.) and humidity (50±10%) on a 12-hour light/dark cycle. Animals have ad libitum access to water and food throughout studies. On the day of testing, they are brought into the testing room and allowed to acclimate for 1 hour. To begin testing, the tail is attached to a piece of tape which is then attached to a hook on the ceiling of a sound-attenuated chamber. Immobility is automatically recorded using the Med Associates software. Compounds are administered acutely at a fixed pretreatment interval before session.

Rat Forced Swim Assay

Male Sprague Dawley rats are housed in pairs in rooms maintained at a constant temperature (21-23° C.) and humidity (50±10%) on a 12-hour light/dark cycle. Animals have ad libitum access to water and food throughout studies. Animals are handled for two minutes each on the two days prior to the start of the experiment. On the first day of testing, rats are placed in the swim tank (a Pyrex cylinder 46 cm tall×21 cm in diameter, filled with 30 cm of water ranging between 24-26° C.) for 15 minutes (the pre-swim session). At the end of the 15-minute session, rats are dried and replaced in their home cage. Compounds are administered at three time points in the next 24 hour (23.5, 5, and 1 hour), prior to a second test swim. This swim test is 5 minutes in duration and the animals' behavior is videotaped and active behaviors (immobility, swimming, climbing) are scored. At the end of each 5-second period during the 5-minute test session the rat's behavior is scored as one of the following: immobility (the rat remained floating in the water without struggling and made only those movements necessary to keep its head above water), swimming (the rat made active swimming motions, more than necessary to merely maintain its head above water, e.g., moving around in the cylinder), or climbing (the rat made active movements with its forepaws in and out of the water, usually directed against the cylinder wall). Compounds are only identified by a predesignated code and the experimenter remains blinded throughout the experiment (including while scoring videotapes).

Rat and Mouse Locomotor Activity

Animals are housed according to conditions described above for the two species. The testing apparatus consisted of Plexiglas chambers equipped with Digiscan activity monitors (Omnitech Electronics, Columbus, Ohio) that detect interruptions of eight photobeams. Horizontal activity was recorded in 5-minute bins for a total of 60 minutes and expressed as total distance covered (in cm). Compounds were administered acutely at a fixed pretreatment interval prior to testing.

Although the invention has been described in detail, for the purpose of illustration, it is understood that such detail is for that purpose and variations can be made therein by those skilled in the art without departing from the spirit and scope of the invention which is defined by the following claims.

What is claimed:

1. A compound of formulae I(A-E) having the following structure:

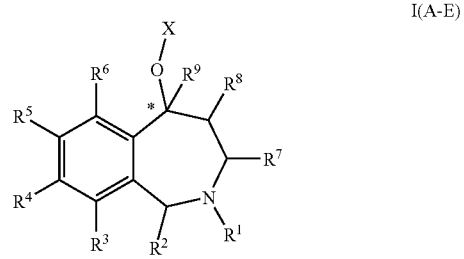

I(A-E)

wherein:
the carbon atom designated * is in the R or S configuration; and

X represents a 5- or 6-membered aromatic monocyclic carbocycle or heterocycle selected from the group consisting of phenyl, pyridyl, 2-oxo-pyridin-1(2H)-yl, pyrimidinyl, pyridazinyl, pyrazinyl, triazinyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, substituted from 1 to 4 times with substituents as defined below in $R^{14}$, or other 5- or 6-membered aromatic monocyclic carbocycles or heterocycles containing 1-4 heteroatoms selected from the group consisting of oxygen, nitrogen, and sulfur, substituted from 1 to 4 times with substituents as defined below in $R^{14}$; or X is a [5,5]-, [6,5]-, [6,6]-, or [6,7]-fused bicyclic carbocycle or heterocycle selected from the group consisting of indenyl, benzofuranyl, benzothiophenyl, indolyl, isoindolyl, benzooxazolyl, benzothiazolyl, benzoisothiazolyl, benzoisoxazolyl, indazolyl, benzoimidazolyl, benzotriazolyl, naphthyl, quinolinyl, isoquinolinyl, quinazolinyl, cinnolinyl, phthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, imidazo[1,2-a]pyrazinyl, 3,3-dimethyl-2-oxoindolinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, substituted from 1 to 4 times with substituents as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^2$ is gem-dimethyl;

$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^3$, $R^5$, and $R^6$ are each independently a 5- or 6-membered monocyclic carbocycle or heterocycle, optionally substituted from 1 to 4 times with substituents as defined below in $R^{14}$;

$R^4$ is H, halogen, —OR$^{12}$, —S(O)$_n$R$^{13}$, —CN, —C(O)R$^{13}$, —NR C$^{10}$R$^{11}$, C$_1$-C$_6$ alkyl, C$_2$-C$_6$ alkenyl, C$_2$-C$_6$ alkynyl, C$_3$-C$_6$ cycloalkyl, or C$_4$-C$_7$ cycloalkylalkyl, where each of the C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted from 1 to 3 times with substituents as defined below in R$^{15}$;

$R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of C$_1$-C$_3$ alkyl, —C(O)R$^{13}$, and —S(O)$_n$R$^{13}$; or $R^4$ is an aromatic monocyclic or bicyclic carbocycle or an aromatic or non-aromatic monocyclic or bicyclic heterocycle selected from the group consisting of phenyl, pyridyl, 2-oxo-pyridin-1(2H)-yl, pyrimidinyl, pyridazinyl, 6-oxopyridazin-1(6H)-yl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indenyl, indolyl, isoindolyl, benzofuranyl, benzothiophenyl, indolinyl, indazolyl, benzimidazolyl, benzooxazolyl, benzothiazolyl, benzoisoxazolyl, benzoisothiazolyl, benzotriazolyl, naphthyl, quinolinyl, isoquinolinyl, quinazolinyl, cinnolinyl, pthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 3,3-dimethyl-2-oxoindolinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo41,2,4]triazolo[4,3-a]pyridin-2(3H)-yl, and 2-oxooxazolidin-3-yl, or other 5- or 6-membered aromatic monocyclic carbocycles or aromatic or non-aromatic monocyclic or bicyclic heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, substituted from 1 to 4 times with substituents as defined below in R$^{14}$;

provided that for compounds of formula IA, X is substituted phenyl and R$^4$ is substituted aromatic monocyclic or bicyclic carbocycle or heterocycle;

provided that for compounds of formula IB, X is substituted aromatic bicyclic carbocycle or heterocycle and R$^4$ is substituted aromatic monocyclic or bicyclic carbocycle or heterocycle;

provided that for compounds of formula IC, X is substituted phenyl and R$^4$ is H, —OR$^{12}$, —S(O)$_n$R$^{13}$, C(O)R$^{13}$, —NR$^{10}$R$^{11}$, —CN, halogen, or C$_1$-C$_6$ alkyl, where C$_1$-C$_6$ alkyl is optionally substituted from 1 to 3 times with substituents as defined below in R$^{15}$;

provided that for compounds of formula ID, X is substituted aromatic bicyclic carbocycle or heterocycle and R$_4$ is H, —OR$^{12}$, —S(O)$_n$R$^{13}$, C(O)R$^{13}$, —NR$^{10}$R$^{11}$, —CN, halogen, or C$_1$-C$_6$ alkyl, where C$_1$-C$_6$ alkyl is optionally substituted from 1 to 3 times with substituents as defined below in R$^{15}$; and provided that for compounds of formula IE, X is substituted aromatic monocyclic heterocycle and R$^4$ is substituted aromatic monocyclic or bicyclic carbocycle or heterocycle;

$R^7$ is selected from the group consisting of H, —S(O)$_n$R$^{13}$, —C(O)R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, where each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted from 1 to 3 times with substituents as defined below in R$^{15}$;

$R^8$ is selected from the group consisting of H, halogen, —OR$^{12}$, —S(O)$_n$R$^{13}$, —CN, —C(O)R$^{13}$, —NR$^{10}$R$^{11}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, where each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted from 1 to 3 times with substituents as defined below in R$^{15}$; or $R^7$ and $R^8$ are gem-dimethyl, with the proviso that only one of R$^7$ and R$^8$ is gem-dimethyl;

$R^9$ is H, halogen, —OR$^{12}$, —SR$^{10}$, C$_1$-C$_6$alkyl, —CN, or NR$^{10}$R$^{11}$, where C$_1$-C$_6$ alkyl is optionally substituted from 1 to 3 times with substituents as defined below in R$^{15}$;

$R^{10}$ and $R^{11}$ are each independently selected from the group consisting of H, —C(O)R$^{13}$, C$_1$-C$_6$ alkyl, C$_3$-C$_6$ cycloalkyl, and C$_4$-C$_7$ cycloalkylalkyl, where each of C$_1$-C$_6$ alkyl, C$_3$-C$_6$ cycloalkyl, and C$_4$-C$_7$ cycloalkylalkyl is optionally substituted from 1 to 3 times with substituents as defined below in R$^{15}$;

$R^{10}$ and $R^{11}$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in R$^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, and is optionally substituted from 1 to 3 times with a substituent selected independently at each occurrence thereof from the group consisting of halogen, cyano, —OR$^{12}$, —NR$^{12}$R$^{13}$, —S(O)$_n$R$^{13}$, —C(O)R$^{13}$, and C$_1$-C$_4$ alkyl, where each of C$_1$-C$_4$ alkyl is optionally substituted from 1 to 3 times with substituents as defined below in R$^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on a ring carbon with from 1 to 3 times with a substituent selected independently at each occurrence thereof from the group consisting of halogen, cyano, —OR$^{12}$, —NR$^{12}$R$^{13}$, —S(O)$_n$R$^{13}$, —C(O)R$^{13}$, and C$_1$-C$_4$ alkyl, or on the additional nitrogen atom from 1 to 3 times with a substituent selected independently at each occurrence thereof from the group consisting of $S(O)_nR^{13}$, —C(O)$R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{14}$; or when $R^4$ is —$NR^{10}R^{11}$ or —C(O)$NR^{10}R^{11}$, either R or $R^{11}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —C(O)$R^{13}$, and —$S(O)_nR^{13}$, or either $R^{10}$ or $R^{11}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —C(O)$R^{13}$, and —$S(O)_nR^{13}$;

$R^{12}$ is selected from the group consisting of H, $C_1$-$C_4$ alkyl, $C_3$-$C_6$ cycloalkyl, $C_4$-$C_7$ cycloalkylalkyl, and —C(O)$R^{13}$, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{13}$ is selected from the group consisting of H, —$NR^{10}R^{11}$, $C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$; or $R^{12}$ and $R^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or $R^{12}$ and $R^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —$OR^{10}$, —$S(O)_nR^{10}$, —C(O)$R^{10}$, —C(O)$NR^{10}R^{11}$ and $C_1$-$C_4$ alkyl, where each of $C_1$-$C_4$ alkyl is optionally substituted from 1 to 3 times with substituents as defined below in $R^{15}$;

n is 0, 1, or 2;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —C(O)$R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of —CN, halogen, C(O)$R^{13}$, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$;

or an oxide thereof, or a pharmaceutically acceptable salt thereof.

2. The compound according to claim 1, wherein X is substituted phenyl and $R^4$ is substituted aromatic monocyclic or bicyclic carbocycle or heterocycle.

3. The compound according to claim 1, wherein X is substituted aromatic bicyclic carbocycle or heterocycle and $R^4$ is substituted aromatic monocyclic or bicyclic carbocycle or heterocycle.

4. The compound according to claim 1, wherein X is substituted phenyl and $R_4$ is H, —$OR^{12}$, —$S(O)_nR^{13}$, C(O)$R^{13}$, —$NR^{10}R^{11}$, —CN, halogen, and $C_1$-$C_6$ alkyl, wherein $C_1$-$C_6$ alkyl is optionally substituted from 1 to 3 times with substituents as defined in $R^{15}$.

5. The compound according to claim 1, wherein X is substituted aromatic bicyclic carbocycle or heterocycle and $R^4$ is H, —$OR^{12}$, —$S(O)_nR^{13}$, C(O)$R^{13}$, —$NR^{10}R^{11}$, —CN, halogen, and $C_1$-$C_6$ alkyl, wherein $C_1$-$C_6$ alkyl is optionally substituted from 1 to 3 times with substituents as defined in $R^{15}$.

6. The compound according to claim 1, wherein X is substituted aromatic monocyclic heterocycle and $R^4$ is substituted aromatic monocyclic or bicyclic carbocycle or heterocycle.

7. The compound according to claim 1, wherein:

X is phenyl, substituted from 1 to 4 times with substituents as defined in $R^{14}$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, difluoromethoxy or trifluoromethoxy;

$R^5$ is H, fluoro, chloro, methyl, trifluoromethyl, difluoromethoxy, trifluoromethoxy, cyano, hydroxyl or methoxy;

$R^6$ is H, fluoro, chloro, methyl, trifluoromethyl, difluoromethoxy, trifluoromethoxy, cyano, hydroxyl or methoxy;

$R^7$ is H, gem-dimethyl, or $C_1$-$C_4$ alkyl, where $C_1$-$C_4$ alkyl is optionally substituted from 1 to 3 times with substituents as defined below in $R^{15}$;

$R^8$ is H, hydroxyl, fluoro, chloro, methyl, $C_1$-$C_3$ alkyl optionally substituted with hydroxyl or amino, or amino optionally substituted with $C_1$-$C_3$ alkyl; and $R^9$ is H, fluoro, chloro, methyl, hydroxyl, or cyano.

8. The compound according to claim 7, wherein:

$R^4$ is H, halogen, —$OR^{12}$, —$S(O)_nR^{13}$, —CN, —C(O)$R^{13}$, —$NR^{10}R^{11}$, or $C_1$-$C_6$ alkyl, wherein $C_1$-$C_6$ alkyl is optionally substituted from 1 to 3 times with substituents as defined in $R^{15}$.

9. The compound according to claim 7, wherein $R^4$ is phenyl, pyridyl, 2-oxo-pyridin-1(2H)-yl, pyrimidinyl, pyridazinyl, 6-oxopyridazin-1(6H)-yl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indenyl, indolyl, isoindolyl, benzofuranyl, benzothiophenyl, indolinyl, indazolyl, benzimidazolyl, benzooxazolyl, benzothiazolyl, benzoisoxazolyl, benzoisothiazolyl, benzotriazolyl, naphthyl, quinolinyl, isoquinolinyl, quinazolinyl, cinnolinyl, pthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 3,3-dimethyl-2-oxoindolinyl, benzo[c][1,2,5]oxadiazolyl, benzo[c][1,2,5]thiadiazolyl, 3,4-dihydro-2H-benzo [b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, oxooxazolidin-3-yl, substituted from 1 to 4 times with substituents as defined in $R^{14}$.

10. The compound according to claim 1, wherein:
X represents a 5- or 6-membered monocyclic heterocycle selected from the group consisting of pyridyl, 2-oxopyridin-1(2H)-yl, pyrimidinyl, pyridazinyl, pyrazinyl, triazinyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, substituted from 1 to 4 times with substituents as defined in $R^{14}$;
$R^1$ is H, methyl, ethyl, or isopropyl;
$R^2$ is H, methyl, or gem-dimethyl;
$R^3$ is H, methyl, hydroxyl, methoxy, fluoro, chloro, cyano, trifluoromethyl, difluoromethoxy or trifluoromethoxy;
$R^5$ is H, fluoro, chloro, methyl, trifluoromethyl, difluoromethoxy, trifluoromethoxy, cyano, hydroxyl or methoxy;
$R^6$ is H, fluoro, chloro, methyl, trifluoromethyl, difluoromethoxy, trifluoromethoxy, cyano, hydroxyl or methoxy;
$R^7$ is H, gem-dimethyl, or $C_1$-$C_4$ alkyl, where $C_1$-$C_4$ alkyl is optionally substituted from 1 to 3 times with substituents as defined below in $R^{15}$;
$R^8$ is H, hydroxyl, fluoro, chloro, methyl, $C_1$-$C_3$ alkyl optionally substituted with hydroxyl or amino, or amino optionally substituted with $C_1$-$C_3$ alkyl; and
$R^9$ is H, fluoro, chloro, methyl, hydroxyl, or cyano.

11. The compound according to claim 10, wherein $R^4$ is phenyl, pyridyl, 2-oxo-pyridin-1(2H)-yl, pyrimidinyl, pyridazinyl, 6-oxopyridazin-1(6H)-yl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indenyl, indolyl, isoindolyl, benzofuranyl, benzothiophenyl, indolinyl, indazolyl, benzimidazolyl, benzooxazolyl, benzothiazolyl, benzoisoxazolyl, benzoisothiazolyl, benzotriazolyl, naphthyl, quinolinyl, isoquinolinyl, quinazolinyl, cinnolinyl, pthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 3,3-dimethyl-2-oxoindolinyl, benzo[c][1,2,5]oxadiazolyl, benzo[c][1,2,5]thiadiazolyl, 3,4-dihydro-2H-benzo [b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, oxooxazolidin-3-yl, substituted from 1 to 4 times with substituents as defined in $R^{14}$.

12. The compound according to claim 1, wherein:
X is a [5,5]-, [6,5]-, [6,6]-, or [6,7]-fused aromatic bicyclic carbocycle or heterocycle selected from the group consisting of indenyl, benzofuranyl, benzothiophenyl, indolyl, isoindolyl, benzooxazolyl, benzothiazolyl, benzoisothiazolyl, benzoisoxazolyl, indazolyl, benzoimidazolyl, benzotriazolyl, naphthyl, quinolinyl, isoquinolinyl, quinazolinyl, cinnolinyl, phthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, imidazo[1,2-a]pyrazinyl, 3,3-dimethyl-2-oxoindolinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, substituted from 1 to 4 times with substituents as defined in $R^{14}$;
$R^1$ is H, methyl, ethyl, or isopropyl;
$R^2$ is H, methyl, or gem-dimethyl;
$R^3$ is H, methyl, hydroxyl, methoxy, fluoro, chloro, cyano, trifluoromethyl, difluoromethoxy or trifluoromethoxy;
$R^5$ is H, fluoro, chloro, methyl, trifluoromethyl, difluoromethoxy, trifluoromethoxy, cyano, hydroxyl or methoxy;
$R^6$ is H, fluoro, chloro, methyl, trifluoromethyl, difluoromethoxy, trifluoromethoxy, cyano, hydroxyl or methoxy;
$R^7$ is H, gem-dimethyl, or $C_1$-$C_4$ alkyl, where $C_1$-$C_4$ alkyl is optionally substituted from 1 to 3 times with substituents as defined below in $R^{15}$;
$R^8$ is H, hydroxyl, fluoro, chloro, methyl, $C_1$-$C_3$ alkyl optionally substituted with hydroxyl or amino, or amino optionally substituted with $C_1$-$C_3$ alkyl; and
$R^9$ is H, fluoro, chloro, methyl, hydroxyl, or cyano.

13. The compound according to claim 12, wherein:
$R^4$ is H, halogen, —$OR^{12}$, —S (O)$_n R^{13}$, —CN, —C(O)$R^{13}$, —$NR^{10}R^{11}$, or $C_1$-$C_6$ alkyl, wherein $C_1$-$C_6$alkyl is optionally substituted from 1 to 3 times with substituents as defined in $R^{15}$.

14. The compound according to claim 12, wherein $R^4$ is phenyl, pyridyl, 2-oxo-pyridin-1(2H)-yl, pyrimidinyl, pyridazinyl, 6-oxopyridazin-1(6H)-yl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indenyl, indolyl, isoindolyl, benzofuranyl, benzothiophenyl, indolinyl, indazolyl, benzimidazolyl, benzooxazolyl, benzothiazolyl, benzoisoxazolyl, benzoisothiazolyl, benzotriazolyl, naphthyl, quinolinyl, isoquinolinyl, quinazolinyl, cinnolinyl, pthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a] pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 3,3-dimethyl-2-oxoindolinyl, benzo[c][1,2,5]oxadiazolyl, benzo[c][1,2,5]thiadiazolyl, 3,4-dihydro-2H-benzo [b][ 1,4] oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl and oxooxazolidin-3-yl, substituted from 1 to 4 times with substituents as defined in $R^{14}$.

15. The compound according to claim 1, wherein:
   X is thiophenyl, thiazolyl, pyridinyl, phenyl, naphthyl, benzo[b]thiophenyl, or benzofuranyl, substituted with from 1 to 3 substituents selected independently from the group consisting of fluoro, chloro, bromo, methoxy, hydroxyl, cyano, trifluoromethyl, difluoromethyl, trifluoromethoxy, difluoromethoxy, substituted $C_1$-$C_3$ alkyl, methanesulfonyl, carbamoyl, $C_1$-$C_3$ alkyl-substituted carbamoyl, and acetamido;
   $R^1$ is H, methyl, ethyl, isopropyl;
   $R^2$ is H or gem-dimethyl;
   $R^3$ is H, chloro or fluoro;
   $R^4$ is H, methoxy, hydroxyl, methyl, fluoro, bromo, cyano, difluoromethyl, trifluoromethyl, difluoromethoxy, trifluoromethoxy, acetyl, aminomethyl, 1-aminocyclopropyl, morpholinomethyl, 2-hydroxypropan-2-yl, morpholine-4-carbonyl, 2-morpholinoethoxy, 2-(dimethylamino)ethyl(methyl)amino, 2-hydroxyethylamino, piperidin-1-yl, pyrrolidin-1-yl, piperidin-4-ol, morpholino, piperazin-1-yl, 4-methylpiperazin-1-yl, 4-(ethylsulfonyl)piperazin-1-yl, 4-(2-(isopropylamino)-2-oxoethyl)piperazin-1-yl, 4-(pyridin-2-yl)piperazin-1-yl, 4-(pyrimidin-2-yl)piperazin-1-yl, 2-oxopyrrolidin-1-yl, 2-oxopiperidin-1-yl, 6-methylpyridazin-3-yloxy, 6-aminopyridazin-3-yloxy, pyridazin-3-yloxy, pyrazin-2-yloxy, 3-aminopyrazin-2-yloxy, 5-aminopyrazin-2-yloxy, 6-aminopyrazin-2-yloxy,1,2,4-oxadiazol-3-yl, 3,5-dimethylisoxazol-4-yl, 1H-pyrazol-4-yl, 2-cyanophenyl, 3-cyanophenyl, 4-cyanophenyl, 4-(methanesulfonyl)phenyl, 3-(methanesulfonyl)phenyl, 2-(methanesulfonyl)phenyl, carbamoylphenyl, aminopyridinyl, 6-methylpyridazin-3-yl, 6-(trifluoromethyl)pyridazin-3-yl, 6-(difluoromethyl)pyridazin-3-yl, 6-((difluoromethoxy)methyl)pyridazin-3-yl, 6-aminopyridazin-3-yl, 6-(methylamino)pyridazin-3-yl, 6-(dimethylamino)pyridazin-3-yl, 6-morpholinopyridazin-3-yl, 6-(4-hydroxypiperidin-1-yl)pyridazin-3-yl, 6-(4-methylpiperazin-1-yl)pyridazin-3-yl, 6-(hydroxymethyl)pyridazin-3-yl, 6-(methoxycarbonyl)pyridazin-3-yl, 3-aminopyrazin-2-yl, 5-aminopyrazin-2-yl, 6-aminopyrazin-2-yl, 2-oxopyridin-1(2H)-yl, 2-oxopyrrolidin-1-yl, 6-oxo-1,6-dihydropyridazin-3-yl, 6-oxopyridazin-1(6H)-yl, 3-oxo-[1,2,4]triazolo[4,3-a]pyridin-2(3H)-yl, 5,6-dihydroimidazo[1,2-a]pyrazin-7(8H)-yl, 3-(trifluoromethyl)-5,6-dihydro-[1,2,4]triazolo[4,3-a]pyrazin-7(8H)-yl, 3,3-dimethyl-2-oxoindolin-5-yl, 5,6-dihydroimidazo[1,2-a]pyrazin-7(8H)-yl, 3-methyl-[1,2,4]triazolo[4,3-b]-pyridazinyl, or oxooxazolidin-3-yl;
   $R^5$ is H, chloro or fluoro;
   $R^6$ is H, chloro or fluoro;
   $R^7$ is H;
   $R^8$ is H, fluoro, methyl, or hydroxyl; and
   $R^9$ is H or hydroxyl.

16. The compound according to claim 1, wherein the carbon atom designated * is in the R configuration.

17. The compound according to claim 1, wherein the carbon atom designated * is in the S configuration.

18. The compound according to claim 1, wherein the compound is a (+) stereoisomer.

19. The compound according to claim 1, wherein the compound is a (−) stereoisomer.

20. A pharmaceutical composition comprising a pharmaceutically acceptable carrier and a therapeutically effective amount of the compound according to claim 1.

21. A compound selected from the group consisting of:
   (+)-2-methyl-5-(naphthalen-2-yloxy)-8-(pyridazin-3-yl)-2,3,4,5-tetrahydro-1H-benzo[c]azepine;
   (+)-5-(4-chlorophenoxy)-2-methyl-8-(pyridazin-3-yl)-2,3,4,5-tetrahydro-1H-benzo[c]azepine;
   (+)-2-methyl-8-(pyridazin-3-yl)-5-(p-tolyloxy)-2,3,4,5-tetrahydro-1H-benzo[c]azepine;
   (+)-2-methyl-8-(pyridazin-3-yl)-5-(4-(trifluoromethoxy)phenoxy)-2,3,4,5-tetrahydro-1H-benzo[c]azepine;
   (+)-5-(3,5-difluorophenoxy)-2-methyl-8-(pyridazin-3-yl)-2,3,4,5-tetrahydro-1H-benzo[c]azepine;
   (+)-4-(2-Methyl-8-(pyridazin-3-yl)-2,3,4,5-tetrahydro-1H-benzo[c]azepin-5-yloxy)benzonitrile;
   (+)-5-(3,4-Dichlorophenoxy)-2-methyl-8-(pyridazin-3-yl)-2,3,4,5-tetrahydro-1H-benzo[c]azepine;
   (+)-5-(3,4-Difluorophenoxy)-2-methyl-8-(pyridazin-3-yl)-2,3,4,5-tetrahydro-1H-benzo[c]azepine;
   (+)-5-(2,4-Difluorophenoxy)-2-methyl-8-(pyridazin-3-yl)-2,3 ,4,5-tetrahydro- 1H-benzo[c]azepine;
   (−)-2-methyl-5-phenoxy-8-(pyridazin-3-yl)-2,3,4,5-tetrahydro-1H-benzo[c] azepine;
   (−)-2-methyl-8-(pyridazin-3-yl)-5-(pyridin-3-yloxy)-2,3,4,5-tetrahydro-1H-benzo[c]azepine;
   (−)-5 -(2-flurophenoxy)-2-methyl-8-(pyridazin-3-yl)-2 ,3 ,4,5-tetrahydro- 1H-benzo[c]azepine;
   (−)-5 -(3-flurophenoxy)-2-methyl-8-(pyridazin-3-yl)-2 ,3 ,4,5-tetrahydro- 1H-benzo[c]azepine;
   (−)-5 -(3,5 -difluorophenoxy)-2-methyl-8-(pyridazin-3 -yl)-2,3 ,4,5 -tetrahydro- 1H-benzo[c]azepine;
   (+)-2-Methyl-5-(naphthalen- 1 -yloxy)-8-(pyridazin-3-yl)-2,3,4,5-tetrahydro-1H-benzo[c] azepine;
   (+)-2-methyl-8-(6-methylpyridazin-3-yl)-5-phenoxy-2,3,4,5-tetrahydro-1H-benzo[c]azepine;
   (−)-2-methyl-8 -(6-methylpyridazin-3 -yl)-5 -phenoxy-2,3 ,4,5 -tetrahydro- 1H-benzo[c]azepine;
   (−)-5-(4-fluorophenoxy)-2-methyl-8-(pyridazin-3-yl)-2,3,4,5-tetrahydro-1H-benzo[c]azepine;
   (−)-5 -(4-fluorophenoxy)-2-methyl-8 -(pyridazin-3-yl)-2 ,3 ,4,5 -tetrahydro- 1H-benzo[c]azepine;
   (−)-5 -(naphthalen-2-yloxy)-2-methyl-8 -(pyridazin-3-yl)-2 ,3 ,4,5-tetrahydro- 1H-benzo[c]azepine;
   (±)-5-(4-fluorophenoxy)-2-methyl-8-(pyrimidin-5-yl)-2,3,4,5-tetrahydro-1H-benzo [c]azepine;
   (±)-5-(4-fluorophenoxy)-2-methyl- 8-(1H-pyrazol-4-yl)-2 ,3 ,4,5-tetrahydro- 1H-benzo[c] azepine;
   (±)-6-(5-(4-fluorophenoxy)-2-methyl-2,3,4,5-tetrahydro-1H-benzo [c] azepin-8 -yl)pyridazin-3-amine;
   (±)-8-(4-(ethylsulfonyl)piperazin- 1 -yl)-5 -(4-fluorophenoxy)-2-methyl-2,3 ,4,5-tetrahydro- 1H-benzo[c] azepine;
   (+)-2-methyl-5 -(4-(trifluoromethyl)phenoxy)-2 ,3 ,4,5-tetrahydro-1 H-benzo [c]azepine;
   (−)-2-methyl-5-(4-(trifluoromethyl)phenoxy)-2,3,4,5-tetrahydro-1H-benzo [c]azepine;
   (±)-5-(4-fluorophenoxy)-2-methyl-8-(pyrazin-2-yl)-2,3,4,5-tetrahydro-1H-benzo [c]azepine;
   (±)-6-(5-(4-fluorophenoxy)-2-methyl-2,3,4,5-tetrahydro-1H-benzo [c] azepin-8 -yl)pyridin-2-amine;
   (±)-6-(5-(4-fluorophenoxy)-2-methyl-2,3,4,5-tetrahydro-1H-benzo [c]azepin-8-yl)pyridazin-3(2H)-one;

(±)-5-(4-fluorophenoxy)-2-methyl- 8-(4-(methylsulfonyl)phenyl)-2,3,4,5-tetrahydro- 1H-benzo[c]azepine;
(±)-2-(5-(4-fluorophenoxy)-2-methyl-2,3,4,5-tetrahydro-1H-benzo [c] azepin-8 -yl)benzonitrile;
(±)-8-([1,2,4]triazolo [1,5-a]pyridin-6-yl)-5-(4-fluorophenoxy)-2-methyl-2,3,4,5-tetrahydro- 1H-benzo[c]azepine;
(±)-8-([1,2,4]triazolo[4,3-a]pyridin-6-yl)-5-(4-fluorophenoxy)-2-methyl-2,3,4,5-tetrahydro-1H-benzo[c]azepine;
(±)-1-(5-(4-fluorophenoxy)-2-methyl-2,3,4,5-tetrahydro-1H-benzo[c]azepin-8-yl)pyridin-2(1H)-one;
(−)-8-(6-methylpyridazin-3-yl)-5-phenoxy-2,3,4,5-tetrahydro-1H-benzo[c]azepine;
(−)-2-methyl-8-(pyridazin-3-yl)-5-(quinolin-7-yloxy)-2,3,4,5-tetrahydro-1H-benzo[c]azepine;
(−)-5-(2-chlorophenoxy)-2-methyl-8-(pyridazin-3-yl)-2,3,4,5-tetrahydro-1H-benzo[c]azepine;
(±)-2-(5-(3,5-difluorophenoxy)-2,3,4,5-tetrahydro-1H-benzo[c]azepin-8-yl)-[1,2,4]triazolo[4,3-a]pyridin-3(2H)-one;
(+)-8-([1,2,4]triazolo[1,5-a]pyridin-6-yl)-5-(3,5-difluorophenoxy)-2,3,4,5-tetrahydro-1H-benzo[c]azepine;
(−)-8-([1,2,4]triazolo[1,5-a]pyridin-6-yl)-5-(3,5-difluorophenoxy)-2,3,4,5-tetrahydro-1H-benzo[c] azepine;
(±) 8-(6-(difluoromethoxy)pyridazin-3-yl)-5-(3,5-difluorophenoxy)-2,3,4,5-tetrahydro-1H-benzo[c]azepine;
(±)-2-(5-(3,5-difluorophenoxy)-2-methyl-2,3,4,5-tetrahydro-1H-benzo[c]azepin-8-yl)pyridazin-3(2H)-one;
(±)-2-(5-(3,5-difluorophenoxy)-2,3,4,5-tetrahydro-1H-benzo[c]azepin-8-yl)pyridazin-3(2H)-one;
(+)-8-([1,2,4]triazolo[4,3-a]pyridin-6-yl)-5-(3,5-difluorophenoxy)-2-methyl-2,3,4,5-tetrahydro-1H-benzo[c]azepine;
(−)-8-([1,2,4]triazolo[4,3-a]pyridin-6-yl)-5-(3,5-difluorophenoxy)-2-methyl-2,3,4,5-tetrahydro-1H-benzo[c]azepine;
(+)-8-(6-(difluoromethoxy)pyridazin-3-yl)-5-(3,5-difluorophenoxy)-2-methyl-2,3,4,5-tetrahydro-1H-benzo[c]azepine;
(−)-8-(6-(difluoromethoxy)pyridazin-3-yl)-5-(3,5-difluorophenoxy)-2-methyl-2,3,4,5-tetrahydro-1H-benzo[c]azepine;
(+)-6-(5-(3,5-difluorophenoxy)-2-methyl-2,3,4,5-tetrahydro-1H-benzo[c]azepin-8-yl)pyridazin-3-amine;
(−)-6-(5-(3,5-difluorophenoxy)-2-methyl-2,3,4,5-tetrahydro-1H-benzo[c]azepin-8-yl)pyridazin-3-amine;
(+)-2-(5-(3,5-difluorophenoxy)-2-methyl-2,3,4,5-tetrahydro-1H-benzo[c]azepin-8-yl)-[1,2,4]triazolo[4,3-a]pyridin-3(2H)-one;
(−)-2-(5-(3,5-difluorophenoxy)-2-methyl-2,3,4,5-tetrahydro-1H-benzo[c]azepin-8-yl)-[1,2,4]triazolo[4,3-a]pyridin-3(2H)-one;
1-(5-(3,5-difluorophenoxy)-2-methyl-2,3,4,5-tetrahydro-1H-benzo[c]azepin-8-yl)pyridin-2(1H)-one (Enantiomer A);
1-(5-(3,5-difluorophenoxy)-2-methyl-2,3,4,5-tetrahydro-1H-benzo[c]azepin-8-yl)pyridin-2(1H)-one (Enantiomer B);
(+)-4-(2-methyl-5-phenoxy-2,3,4,5-tetrahydro-1H-benzo[c]azepin-8-yl)benzamide;
(−)-4-(2-methyl-5-phenoxy-2,3,4,5-tetrahydro-1H-benzo[c]azepin-8-yl)benzamide;
(+)-2-Methyl-8-(4-methylsulfonylphenyl)-5-phenoxy-2,3,4,5-tetrahydro-1H-benzo[c]azepine;
(+2-Methyl-8-(4-methylsulfonylphenyl)-5-phenoxy-2,3,4,5-tetrahydro-1H-benzo[c]azepine;
(+)-5-(3,5-difluorophenoxy)-2-methyl-8-(4-(methylsulfonyl)phenyl)-2,3,4,5-tetrahydro-1 H-benzo[c]azepine;
(−)-5-(3,5-difluorophenoxy)-2-methyl-8-(4-(methylsulfonyl)phenyl)-2,3,4,5-tetrahydro-1H-benzo [c]azepine;
(+)-4-(5-(3,5-difluorophenoxy)-2-methyl-2,3,4,5-tetrahydro-1H-benzo[c]azepin-8-yl)benzonitrile;
(−)-4-(5-(3,5-difluorophenoxy)-2-methyl-2,3,4,5-tetrahydro-1H-benzo[c]azepin-8-yl)benzonitrile;
(−)-2-Methyl-5-phenoxy-8-(pyrimidin-2-yl)- 2,3,4,5-tetrahydro-1H-benzo[c]azepine;
(+)-8-(6-aminopyridazin-3-yl)-2-methyl-5-phenoxy-2,3,4,5-tetrahydro-1H-benzo[c]azepine;
(+8-(6-aminopyridazin-3-yl)-2-methyl-5-phenoxy-2,3,4,5-tetrahydro-1H-benzo[c]azepine;
(+5-(2,3-difluorophenoxy)-2-methyl-8-(pyridazin-3-yl)-2,3,4,5-tetrahydro-1H-benzo[c]azepine;
(−)-5-(3-cyanophenoxy)-2-methyl-8-(pyridazin-3-yl)-2,3,4,5-tetrahydro-1H-benzo[c]azepine;
(−)-5-(4-cyanophenoxy)-2-methyl-8-(pyridazin-3-yl)-2,3,4,5-tetrahydro-1H-benzo[c]azepine;
(−)-5-(2,5-difluorophenoxy)-2-methyl-8-(pyridazin-3-yl)-2,3,4,5-tetrahydro-1H-benzo[c]azepine;
and (−)-5-(2,6-difluorophenoxy)-2-methyl-8-(pyridazin-3-yl)-2,3,4,5-tetrahydro-1H-benzo[c]azepine.

22. The compound according to claim 21 selected from the group consisting of:
(+)-2-methyl-5-(naphthalen-2-yloxy)-8-(pyridazin-3-yl)-2,3,4,5-tetrahydro-1H-benzo[c]azepine;
(−)-2-methyl-5-phenoxy-8-(pyridazin-3-yl)-2,3,4,5-tetrahydro-1H-benzo[c]azepine;
(−)-2-methyl-8-(pyridazin-3-yl)-5-(pyridin-3-yloxy)-2,3,4,5-tetrahydro-1H-benzo[c]azepine;
(−)-2-Methyl-5-(naphthalen-1-yloxy)-8-(pyridazin-3-yl)-2,3,4,5-tetrahydro-1H-benzo[c]azepine;
(+)-2-methyl-8-(6-methylpyridazin-3-yl)-5-phenoxy-2,3,4,5-tetrahydro-1H-benzo[c]azepine;
(−)-2-methyl-8-(6-methylpyridazin-3-yl)-5-phenoxy-2,3,4,5-tetrahydro-1H-benzo[c]azepine;
(−)-5-(naphthalen-2-yloxy)-2-methyl-8-(pyridazin-3-yl)-2,3,4,5-tetrahydro-1H-benzo[c]azepine;
(−)-8-(6-methylpyridazin-3-yl)-5-phenoxy-2,3,4,5-tetrahydro-1H-benzo[c]azepine;
(−)-2-methyl-8-(pyridazin-3-yl)-5-(quinolin-7-yloxy)-2,3,4,5-tetrahydro-1H-benzo[c]azepine;
(+)-4-(2-methyl-5-phenoxy-2,3,4,5-tetrahydro-1H-benzo[c]azepin-8-yl)benzamide;
(−)-4-(2-methyl-5-phenoxy-2,3,4,5-tetrahydro-1H-benzo[c]azepin-8-yl)benzamide;
(+)-2-Methyl-8-(4-methylsulfonylphenyl)-5-phenoxy-2,3,4,5-tetrahydro-1H-benzo[c]azepine;
(−)-2-Methyl-8-(4-methylsulfonylphenyl)-5-phenoxy-2,3,4,5-tetrahydro-1H-benzo[c]azepine;
(−)-2-Methyl-5-phenoxy-8-(pyrimidin-2-yl)- 2,3,4,5-tetrahydro-1H-benzo[c]azepine;
(+)-8-(6-aminopyridazin-3-yl)-2-methyl-5-phenoxy-2,3,4,5-tetrahydro-1H-benzo[c]azepine; and
(−)-8-(6-aminopyridazin-3-yl)-2-methyl-5-phenoxy-2,3,4,5-tetrahydro-1H-benzo[c]azepine.

* * * * *